United States Patent
Ryan et al.

(10) Patent No.: US 11,229,783 B2
(45) Date of Patent: *Jan. 25, 2022

(54) DISINFECTION CAP FOR IV NEEDLELESS CONNECTORS

(71) Applicant: Becton, Dickinson and Company, Franklin Lakes, NJ (US)

(72) Inventors: Kevin M. Ryan, Whitehouse Station, NJ (US); Nichola Charles, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 188 days.

This patent is subject to a terminal disclaimer.

(21) Appl. No.: 16/547,024

(22) Filed: Aug. 21, 2019

(65) Prior Publication Data

US 2020/0046960 A1    Feb. 13, 2020

Related U.S. Application Data

(63) Continuation of application No. 15/408,278, filed on Jan. 17, 2017, now Pat. No. 10,391,295.

(Continued)

(51) Int. Cl.
*A61M 39/16* (2006.01)
*A61M 39/20* (2006.01)
*A61M 39/10* (2006.01)

(52) U.S. Cl.
CPC .......... *A61M 39/20* (2013.01); *A61M 39/162* (2013.01); *A61M 2039/1033* (2013.01); *A61M 2039/1038* (2013.01)

(58) Field of Classification Search
CPC .. A61M 2039/1033; A61M 2039/1038; A61M 39/162; A61M 39/20; A61M 39/10
See application file for complete search history.

(56) References Cited

U.S. PATENT DOCUMENTS

| | | |
|---|---|---|
| 3,147,876 A | 9/1964 | Lepore |
| 5,006,114 A | 4/1991 | Rogers et al. |

(Continued)

FOREIGN PATENT DOCUMENTS

| | | |
|---|---|---|
| DE | 202008018277 U1 | 8/2012 |
| DE | 202015101511 U1 | 5/2015 |

(Continued)

OTHER PUBLICATIONS

3M Health Care, "3M Curos Jet Disinfecting Cap Video," YouTube, Nov. 21, 2016, 1:12, 1:21-1:34. www.youtube.com/watch?v=MiUNz7lmuK4.

*Primary Examiner* — Deanna K Hall
(74) *Attorney, Agent, or Firm* — Dickinson Wright PLLC

(57) ABSTRACT

Disinfection cap includes housing comprising closed top, essentially cylindrical sidewall, and open bottom formed by the sidewall with opening to inner cavity within the housing for receiving mating feature of needleless connector. Disinfection sponge can be configured within inner cavity, with removable cover sealing opening to inner cavity to seal sponge within inner cavity prior to cap use. Inner cavity includes threads on inner surface of its sidewall that do not correspond to the mating feature of needleless connector. One thread engages with mating feature of needleless connector. Plurality of disinfection caps can be disposed on strip of IV pole hanging device such that each cap can be peeled off the strip unsealed for immediate use, or separated from the strip sealed for later use.

14 Claims, 37 Drawing Sheets

Related U.S. Application Data

(60) Provisional application No. 62/279,986, filed on Jan. 18, 2016, provisional application No. 62/300,247, filed on Feb. 26, 2016.

(56) References Cited

U.S. PATENT DOCUMENTS

| | | |
|---|---|---|
| 5,197,620 A | 3/1993 | Gregory |
| 5,353,969 A | 10/1994 | Balderrama |
| D410,081 S | 5/1999 | Sweeney et al. |
| 5,954,957 A | 9/1999 | Chin-Loy et al. |
| 6,074,366 A | 6/2000 | Rogers et al. |
| 6,146,360 A | 11/2000 | Rogers et al. |
| 6,416,496 B1 | 7/2002 | Rogers et al. |
| 6,482,188 B1 | 11/2002 | Rogers et al. |
| 6,664,893 B1 | 12/2003 | Eveland et al. |
| 6,665,385 B2 | 12/2003 | Rogers et al. |
| 6,957,107 B2 | 10/2005 | Rogers et al. |
| 6,979,323 B2 | 12/2005 | Rogers et al. |
| 7,002,468 B2 | 2/2006 | Eveland et al. |
| 7,130,396 B2 | 10/2006 | Rogers et al. |
| D607,325 S | 1/2010 | Rogers et al. |
| 7,704,002 B2 | 4/2010 | Fisher et al. |
| 7,780,794 B2 | 8/2010 | Rogers et al. |
| 7,857,793 B2 | 12/2010 | Raulerson et al. |
| 7,922,701 B2 | 4/2011 | Buchman |
| 7,985,302 B2 | 7/2011 | Rogers et al. |
| 7,993,309 B2 | 8/2011 | Schweikert |
| 8,065,773 B2 | 11/2011 | Vaillancourt et al. |
| 8,069,523 B2 | 12/2011 | Vaillancourt et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,273,303 B2 | 9/2012 | Ferlic et al. |
| 8,290,129 B2 | 10/2012 | Rogers et al. |
| 8,328,767 B2 | 12/2012 | Solomon et al. |
| 8,336,151 B2 | 12/2012 | Kerr et al. |
| 8,336,152 B2 | 12/2012 | Vaillancourt et al. |
| 8,343,112 B2 | 1/2013 | Solomon et al. |
| 8,388,894 B2 | 3/2013 | Colantonio et al. |
| 8,506,538 B2 | 8/2013 | Chelak |
| 8,523,830 B2 | 9/2013 | Solomon et al. |
| 8,523,831 B2 | 9/2013 | Solomon et al. |
| 8,627,483 B2 | 1/2014 | Rachlin et al. |
| 8,628,501 B2 | 1/2014 | Hadden |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,671,496 B2 | 3/2014 | Vaillancourt et al. |
| 8,696,820 B2 | 4/2014 | Vaillancourt et al. |
| 8,721,627 B2 | 5/2014 | Alpert |
| 8,777,504 B2 | 7/2014 | Shaw et al. |
| 8,808,637 B2 | 8/2014 | Ferlic |
| 8,828,327 B2 | 9/2014 | Colantonio et al. |
| 8,832,894 B2 | 9/2014 | Rogers et al. |
| 8,834,650 B2 | 9/2014 | Rogers et al. |
| 8,845,593 B2 | 9/2014 | Anderson et al. |
| 8,961,475 B2 | 2/2015 | Solomon et al. |
| 8,968,268 B2 | 3/2015 | Anderson et al. |
| 9,259,535 B2 | 2/2016 | Anderson et al. |
| 10,391,295 B2 * | 8/2019 | Ryan ............... A61M 39/162 |
| 2003/0040708 A1 | 2/2003 | Rogers et al. |
| 2004/0073171 A1 | 4/2004 | Rogers et al. |
| 2005/0165351 A1 | 7/2005 | Tamagni, Jr. |
| 2005/0242578 A1 | 11/2005 | Evans et al. |
| 2009/0165351 A1 | 1/2009 | Ryan |
| 2009/0149819 A1 | 6/2009 | Chelak |
| 2010/0003067 A1 | 1/2010 | Shaw et al. |
| 2010/0292673 A1 | 11/2010 | Korogi et al. |
| 2010/0306938 A1 | 12/2010 | Rogers et al. |
| 2011/0044850 A1 | 2/2011 | Solomon et al. |
| 2011/0232020 A1 | 9/2011 | Rogers et al. |
| 2011/0265825 A1 | 11/2011 | Rogers et al. |
| 2011/0314619 A1 | 12/2011 | Schweikert |
| 2012/0078203 A1 | 3/2012 | Gaube et al. |
| 2012/0111368 A1 | 5/2012 | Rahimy et al. |
| 2012/0135201 A1 | 5/2012 | Chang et al. |
| 2012/0216359 A1 | 8/2012 | Rogers et al. |
| 2012/0216360 A1 | 8/2012 | Rogers et al. |
| 2012/0302997 A1 | 11/2012 | Gardner et al. |
| 2013/0030414 A1 | 1/2013 | Gardner et al. |
| 2013/0072909 A1 | 3/2013 | Solomon et al. |
| 2013/0136801 A1 | 5/2013 | Tennican |
| 2013/0138083 A1 | 5/2013 | Tennican |
| 2013/0138085 A1 | 5/2013 | Tennican |
| 2013/0171030 A1 | 7/2013 | Ferlic et al. |
| 2013/0335195 A1 | 12/2013 | Rogers |
| 2013/0338644 A1 | 12/2013 | Solomon et al. |
| 2013/0345645 A1 | 12/2013 | Chelak |
| 2014/0135739 A1 | 5/2014 | Solomon et al. |
| 2014/0150832 A1 | 6/2014 | Rogers et al. |
| 2014/0182623 A1 | 7/2014 | Vaillancourt et al. |
| 2014/0188089 A1 | 7/2014 | Midgette et al. |
| 2014/0248181 A1 | 9/2014 | Solomon et al. |
| 2014/0248182 A1 | 9/2014 | Solomon et al. |
| 2014/0261558 A1 | 9/2014 | Rogers et al. |
| 2014/0261581 A1 | 9/2014 | Rogers |
| 2014/0339812 A1 | 11/2014 | Carney et al. |
| 2014/0366914 A1 | 12/2014 | Kerr et al. |
| 2015/0086441 A1 | 3/2015 | She et al. |
| 2015/0273199 A1 | 10/2015 | Adams et al. |
| 2015/0314119 A1 | 11/2015 | Anderson et al. |
| 2015/0314120 A1 | 11/2015 | Gardner |
| 2016/0015959 A1 | 1/2016 | Solomon et al. |
| 2016/0045629 A1 | 2/2016 | Gardner et al. |
| 2016/0074648 A1 | 3/2016 | Kerr et al. |
| 2016/0185514 A1 | 6/2016 | Tennican |
| 2016/0325089 A1 | 11/2016 | Burkholz |
| 2016/0354288 A1 | 12/2016 | Uehara et al. |
| 2017/9959913 | 2/2017 | Bedoe et al. |

FOREIGN PATENT DOCUMENTS

| | | |
|---|---|---|
| EP | 2444117 A1 | 4/2012 |
| EP | 2474337 A1 | 7/2012 |
| EP | 2554203 A1 | 2/2013 |
| EP | 2606930 A1 | 6/2013 |
| JP | H08317994 A | 12/1996 |
| JP | 2009136681 A | 6/2009 |
| JP | 2012528689 A | 11/2012 |
| JP | 2013523222 A | 6/2013 |
| JP | 2014513569 A | 6/2014 |
| WO | 9846278 A1 | 10/1998 |
| WO | 03006077 A1 | 1/2003 |
| WO | 03068293 A1 | 8/2003 |
| WO | 2005055919 A1 | 6/2005 |
| WO | 2006083333 A1 | 8/2006 |
| WO | 2008009946 A1 | 1/2008 |
| WO | 2008009948 A1 | 1/2008 |
| WO | 2008089196 A1 | 7/2008 |
| WO | 2008100950 A1 | 8/2008 |
| WO | 2008144298 A1 | 11/2008 |
| WO | 2009002474 A1 | 12/2008 |
| WO | 2009002887 A1 | 12/2008 |
| WO | 2010002757 A1 | 1/2010 |
| WO | 2010141508 A1 | 12/2010 |
| WO | 2011028722 A1 | 3/2011 |
| WO | 2011053924 A1 | 5/2011 |
| WO | 2011066586 A1 | 6/2011 |
| WO | 2011120017 A1 | 9/2011 |
| WO | 2012052467 A2 | 4/2012 |
| WO | 201206///8 | 5/2012 |
| WO | 2012083140 A1 | 6/2012 |
| WO | 2012112815 A1 | 8/2012 |
| WO | 2012162259 A1 | 11/2012 |
| WO | 2013066285 A1 | 5/2013 |
| WO | 2013076742 A1 | 5/2013 |
| WO | 2013082174 A1 | 6/2013 |
| WO | 2013082180 A1 | 6/2013 |
| WO | 2013082187 A1 | 6/2013 |
| WO | 2013083279 A1 | 6/2013 |
| WO | 2013090503 A1 | 6/2013 |

(56) References Cited

FOREIGN PATENT DOCUMENTS

| WO | 2013119504 A1 | 8/2013 |
| WO | 2013119505 A1 | 8/2013 |
| WO | 2013119508 A1 | 8/2013 |
| WO | 2013119509 A1 | 8/2013 |
| WO | 2013123202 A2 | 8/2013 |
| WO | 2013184716 A1 | 12/2013 |
| WO | 2013192574 A1 | 12/2013 |
| WO | 2014022353 A1 | 2/2014 |
| WO | 2014074419 A1 | 5/2014 |
| WO | 2014077906 A1 | 5/2014 |
| WO | 2014086437 A1 | 6/2014 |
| WO | 2014106047 A1 | 7/2014 |
| WO | 2014116883 A1 | 7/2014 |
| WO | 2014133826 A1 | 9/2014 |
| WO | 2014151949 A1 | 9/2014 |
| WO | 2014159346 A1 | 10/2014 |
| WO | 2014160154 A1 | 10/2014 |
| WO | 2014169352 A1 | 10/2014 |
| WO | 2014186701 A2 | 11/2014 |
| WO | 2015044904 A1 | 4/2015 |
| WO | 2015087880 A1 | 6/2015 |
| WO | 2015120336 A1 | 8/2015 |
| WO | 2015128310 A1 | 9/2015 |
| WO | 2015128325 A1 | 9/2015 |
| WO | 2015164129 A2 | 10/2015 |
| WO | 2015168677 A1 | 11/2015 |
| WO | 2015174953 A1 | 11/2015 |
| WO | 2015184189 A1 | 12/2015 |
| WO | 2016044821 A1 | 3/2016 |

* cited by examiner

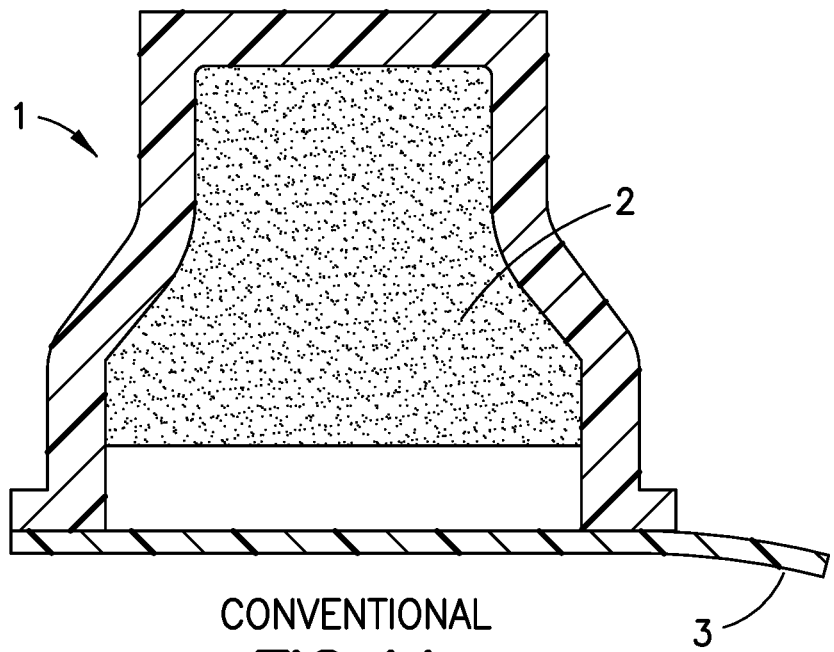
CONVENTIONAL
FIG.1A
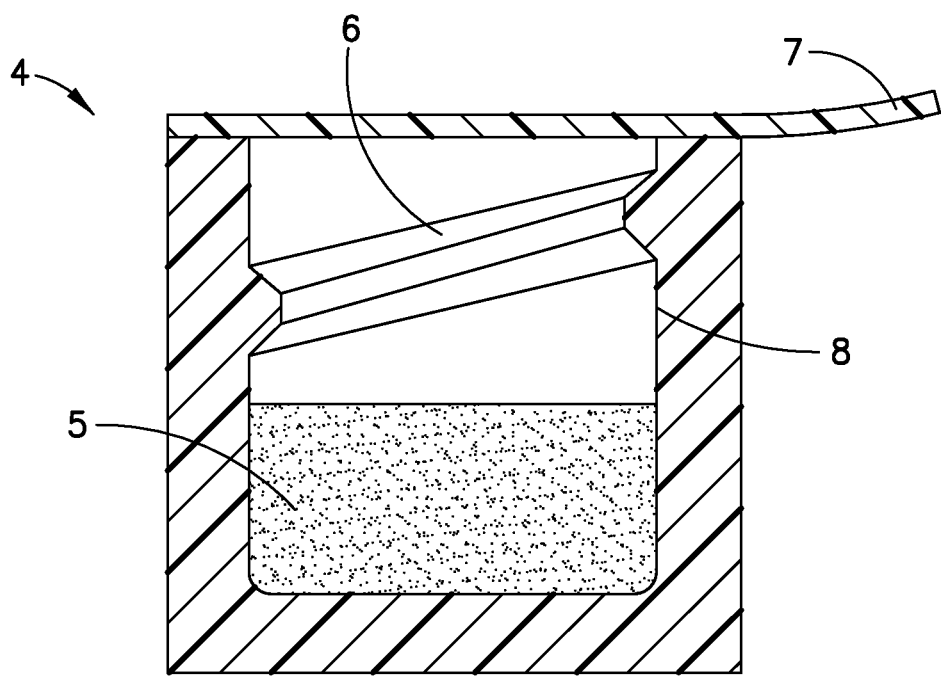
CONVENTIONAL
FIG.1B

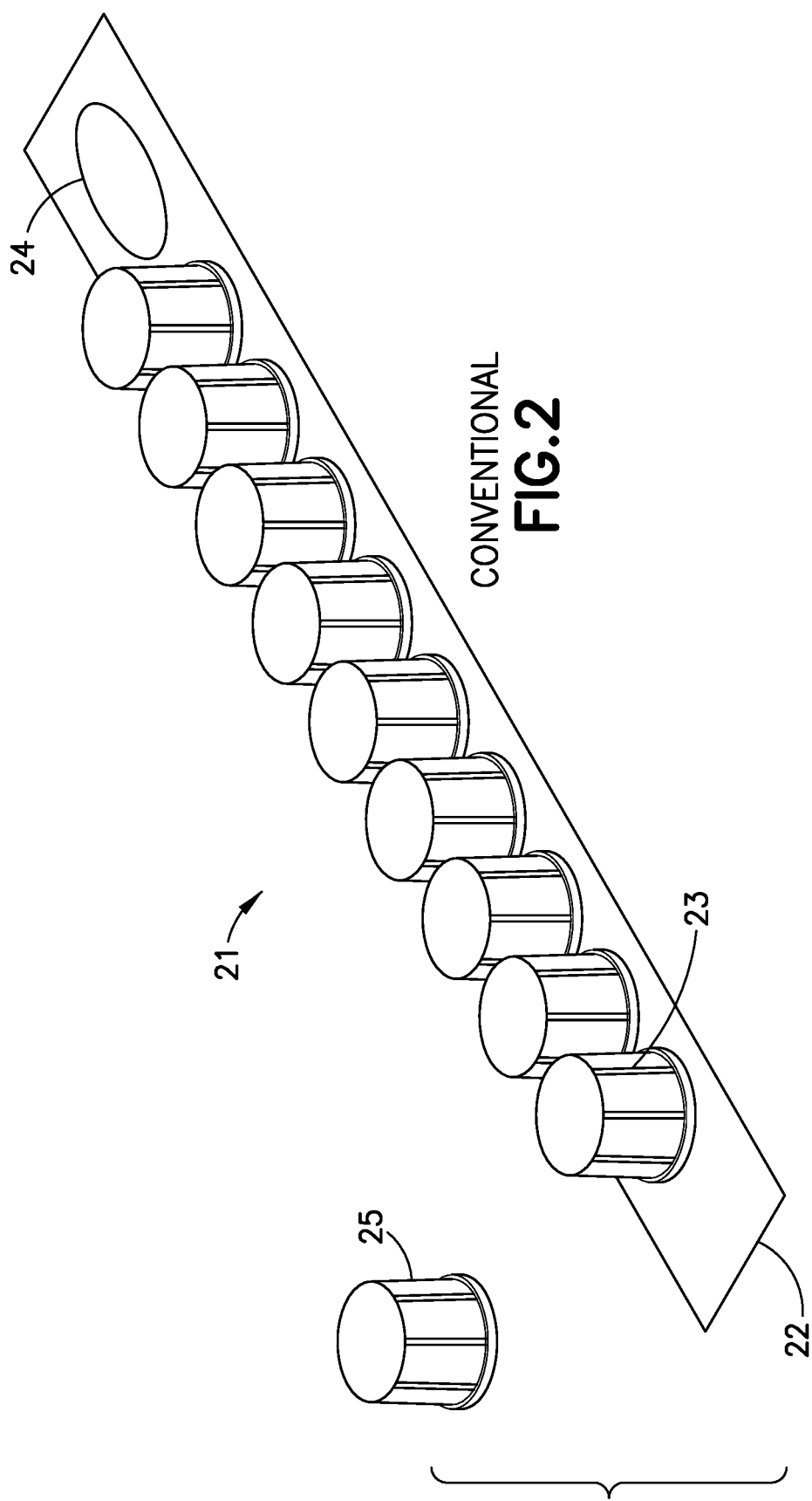
CONVENTIONAL
FIG.2

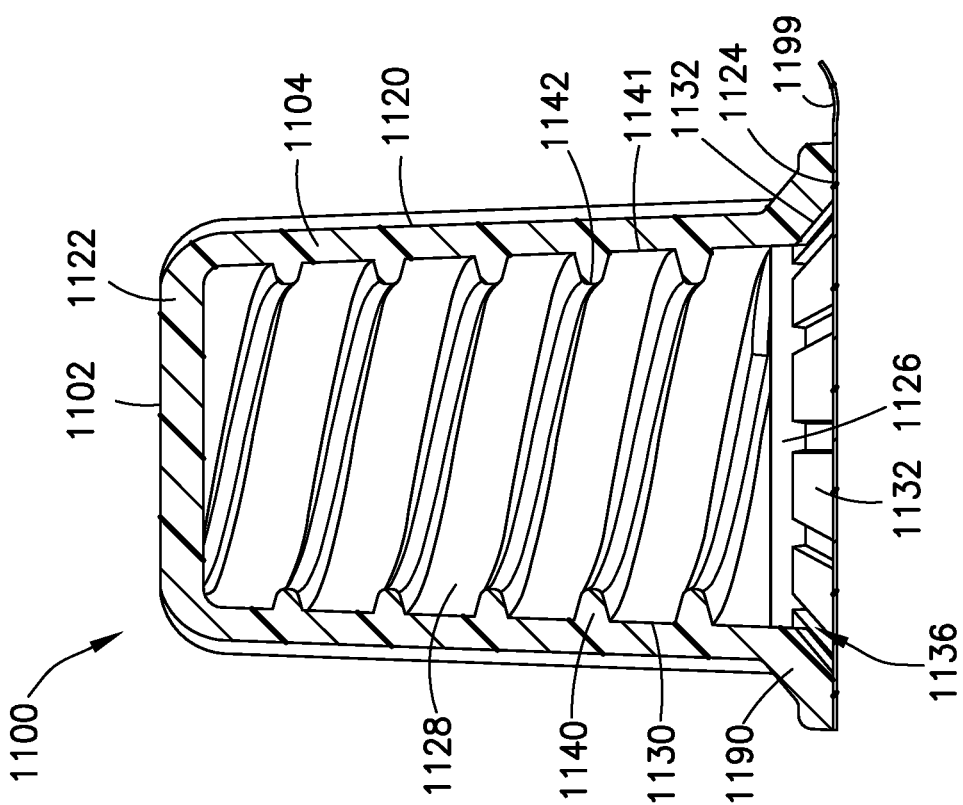
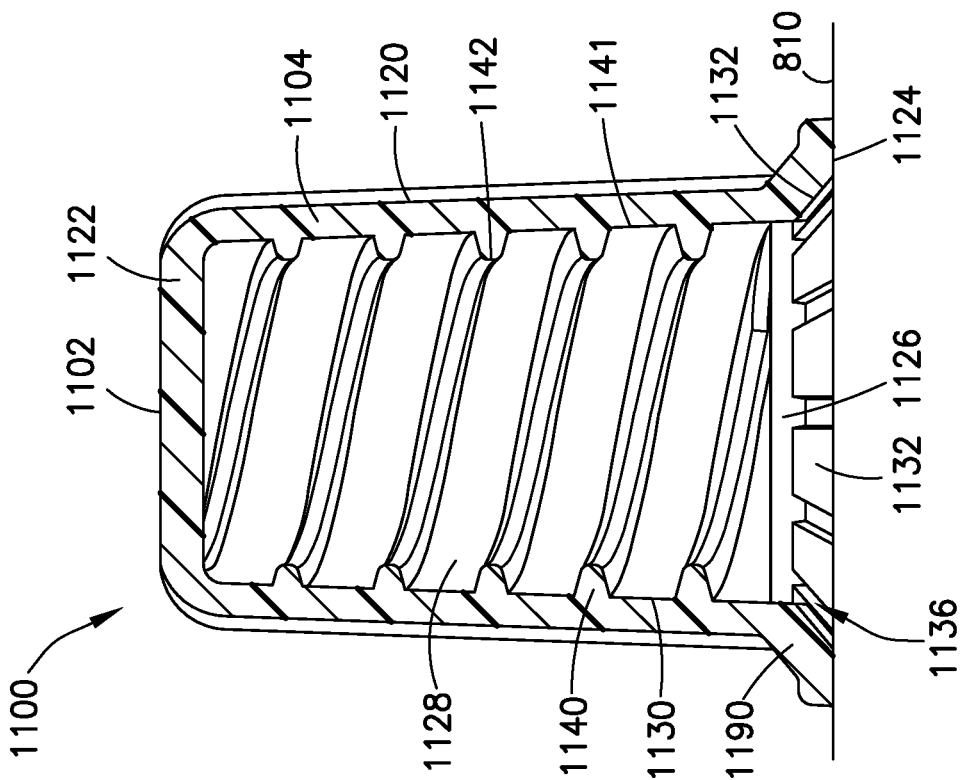

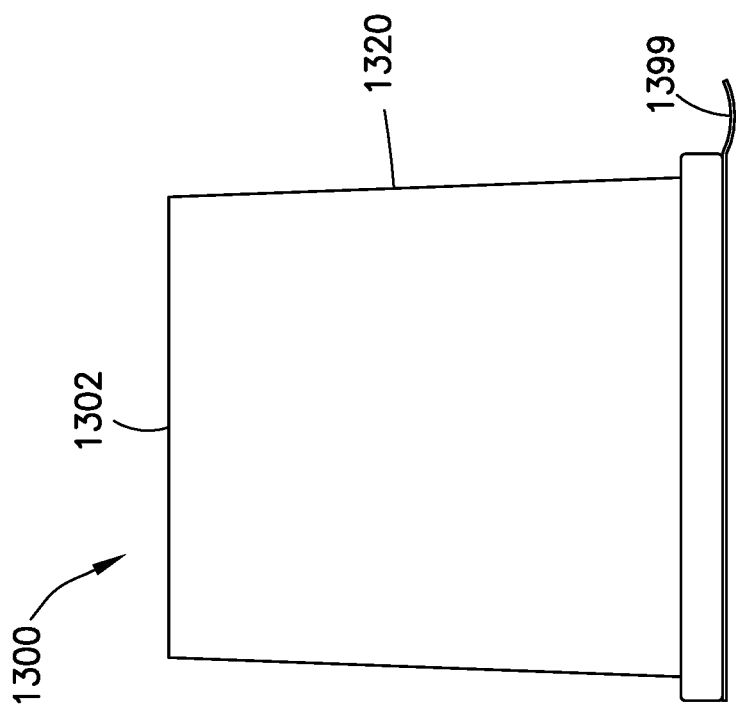
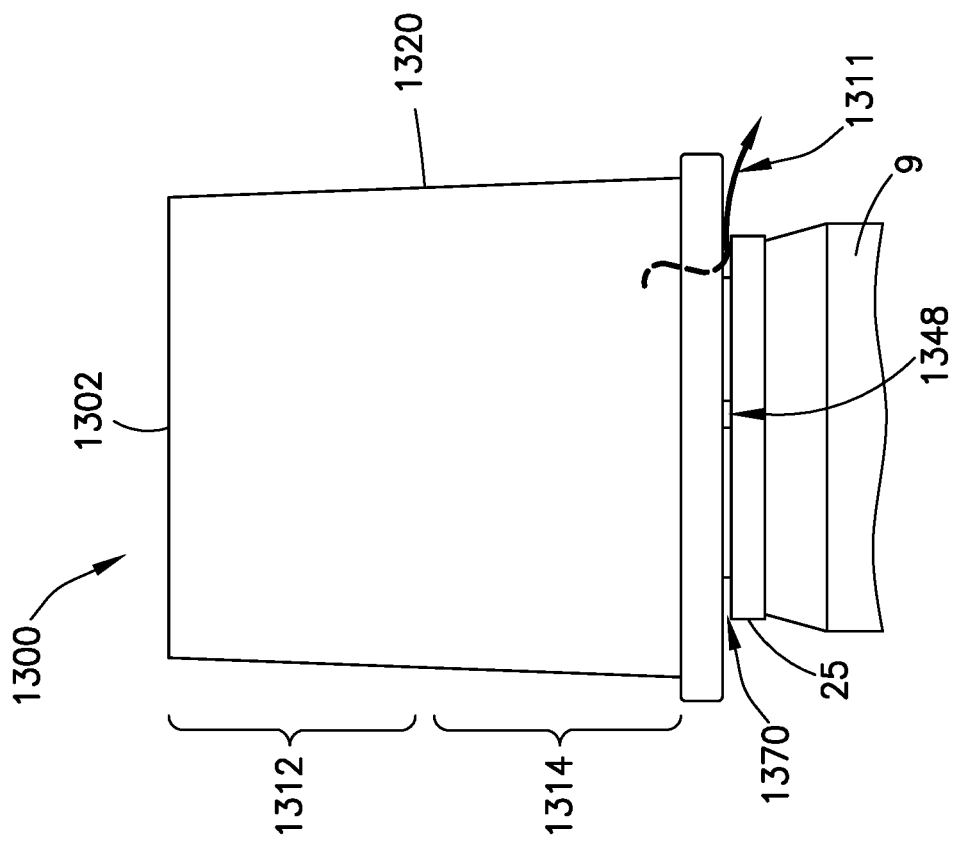

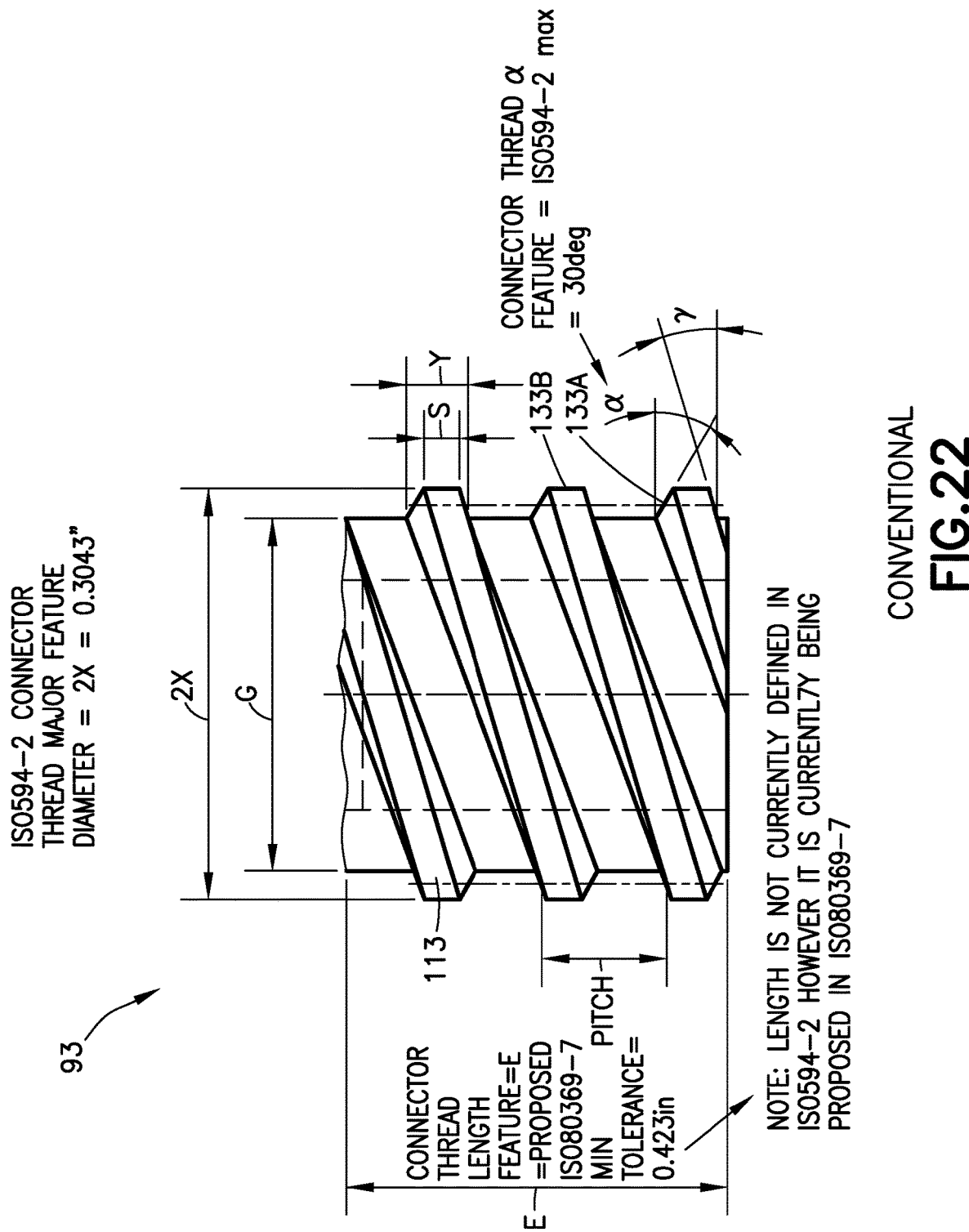
CONVENTIONAL
FIG.22

SECTION AC-AC

SECTION E-E

DETAIL A

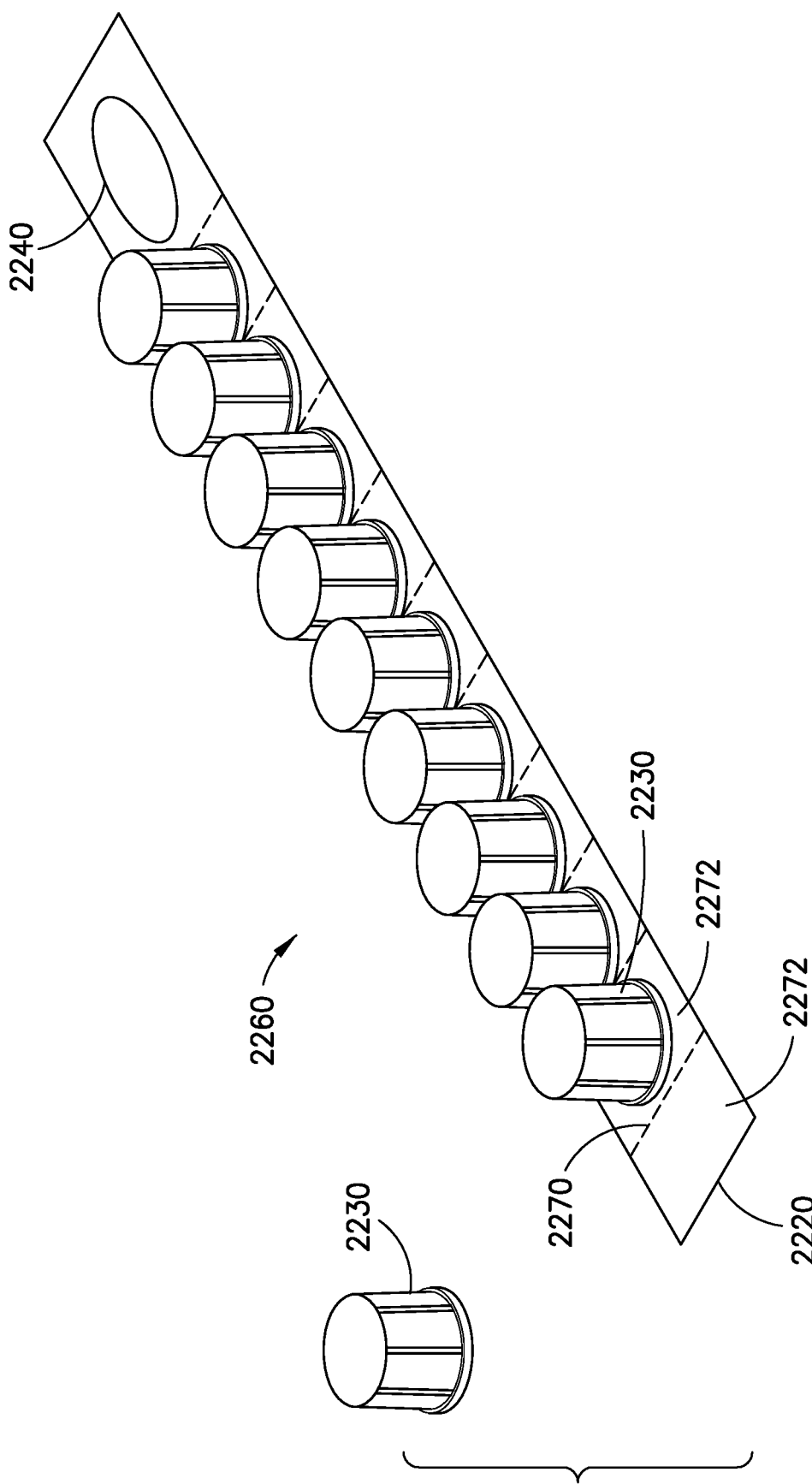

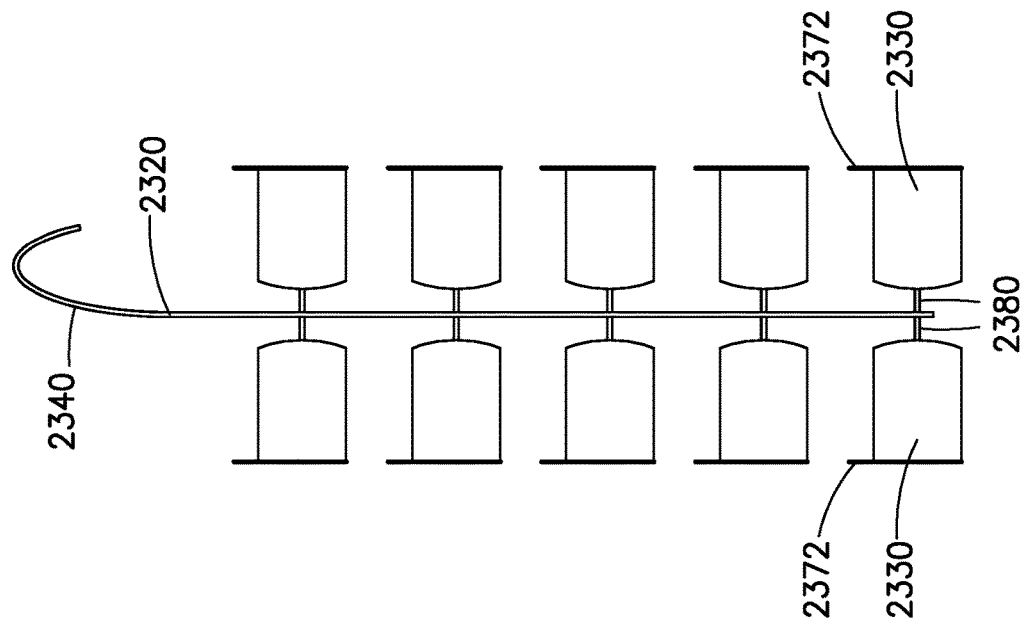
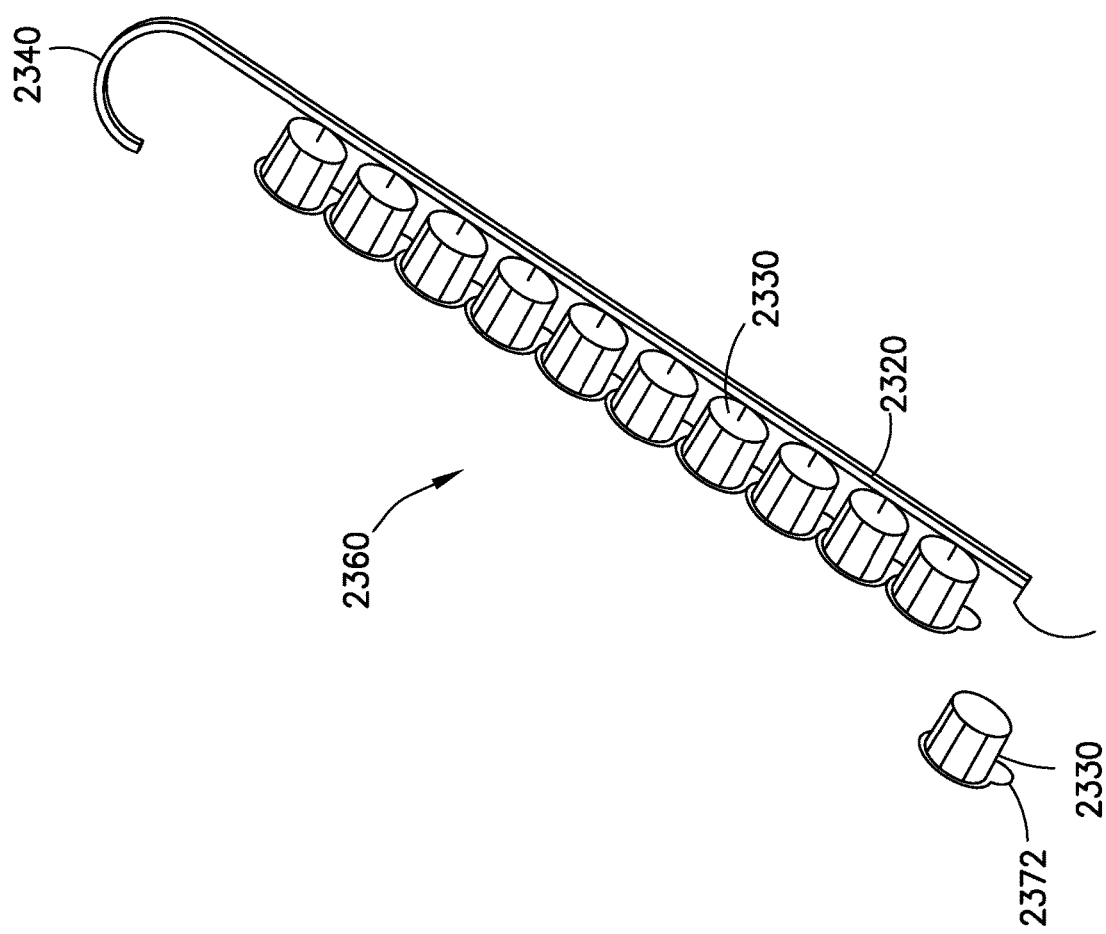

DISINFECTION CAP FOR IV NEEDLELESS CONNECTORS

CROSS-REFERENCE TO RELATED APPLICATIONS

This application is a continuation of U.S. patent application Ser. No. 15/408,278 filed on Jan. 17, 2017, which claim priority under 35 USC § 119(e) from U.S. Provisional Patent Applications No. 62/279,986 filed on Jan. 18, 2016 and 62/300,247 filed on Feb. 26, 2016, the contents of which (including all attachments filed therewith) are hereby incorporated by reference in their entirety.

FIELD OF THE INVENTION

Generally, exemplary embodiments of the present invention relate to the fields of medical disinfection caps, and in particular disinfection caps for uses with IV needleless connectors.

BACKGROUND OF THE INVENTION

In order to decrease Catheter-related bloodstream infection (CRBSI) cases, which are high impact events with high costs and high associated mortality, needleless connector disinfection Cap space continues to grow at a rapid pace since disinfection caps were originally disclosed in U.S. Patent Publication No. 2007/011233 which issued as U.S. Pat. No. 8,740,864 (entire disclosures of both of which are incorporated herein by reference), and introduced on the market. Disinfection caps such as those disclosed in the U.S. Pat. No. 8,740,864 are illustrated in FIGS. 1A and 1B, where cap 1 includes a disinfecting pad 2 and a lid 3, and cap 4 includes a disinfecting pad 5 and lid 7, as well as threads 6 on its inner circumference 8 to interlock with needleless connector hub. As illustrated in FIG. 2, a plurality of disinfection caps 23, such as cap 1 and/or cap 7 of FIGS. 1A and 1B, can be disposed on a strip 22, which includes an opening 24 for hanging strip 22 on an IV pole. In an IV pole hanging device 21, strip 22 can serve as a common lid, for example having the same function as lid 3 and/or 7, for caps 23 disposed thereon, such that removed cap 25 is ready for immediate placement on a needleless connector.

Disinfection caps have been added to the Society for Healthcare Epidemiology of America (SHEA) guidelines and early indications are that caps will also be incorporated into the 2016 Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including the CRBSI events described before. Nurses will typically utilize a 70% IPA alcohol pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Cap technology presents significant challenges associated with needleless connectors. All of the disinfection caps currently on the market contain 70% isopropyl alcohol as the active disinfection ingredient. However, many of the needleless connector designs use Acrylic or similar material for the main housing. Acrylic has mild to poor chemical stability resistance to isopropyl alcohol over prolonged exposure times. Hence the isopropyl alcohol can cause chemical breakdown damage of Acrylic in the form of discoloration and/or cracking of the needleless connector material. In addition, nearly all of the needleless connectors on the market use silicone material for the fluid path valve designs. Silicone materials have a mild to poor chemical stability resistance to isopropyl alcohol over prolonged exposure times. This can lead to swelling of the silicone parts which can then cause the needleless connector valve to stick closed and/or fail to close (causing blood leakage). Additionally, increased silicone swelling could increase stress on the connector housing which could amplify the outer Acrylic needleless connector housing cracking issues.

Conventionally, in order to address the issue of isopropyl alcohol chemical incompatibility with needleless connector materials, disinfection cap having alcohol vents (such as those described in U.S. Pat. Nos. 8,206,514; 7,985,302; and 7,780, 794) have been developed. Such vents allow a cap to vent the disinfecting alcohol away from the needleless connectors faster in comparison to caps currently on the market which do not have such vents. Hence, alcohol venting can reduce chemical damage to the needleless connector materials.

However, such conventional vent features have some significant drawbacks. One drawback is that the venting feature can require forming dedicated venting holes in the cap, or be dependent on a significant undercut reign and/or an assembly of two molded parts, main cap housing and a thread ring, as described for example in U.S. Pat. No. 8,206,514. Such conventional venting feature drives a cap design to require separate molding of the parts. These separate parts must then be assembled, then welded or adhesively bonded together. Accordingly, such a design has inherently higher tooling costs, manufacturing complexity, and production costs in comparison to for example a single shot molded cap housing design.

Hence if a disinfection cap could be developed with a venting feature that avoids undercuts it would eliminate the costly assembly and welding steps. In addition, if a disinfection cap could be developed with increased venting performance, it may further reduce needleless connector failures.

SUMMARY OF THE INVENTION

In accordance with an aspect of the present invention, a disinfection cap comprises a housing including a closed top, an essentially cylindrical sidewall, and an open bottom formed by said sidewall with an opening to an inner cavity within said housing for receiving a tip including a mating feature of said needleless connector. A disinfection sponge can be configured within the inner cavity, with a removable cover sealing the opening to the inner cavity to seal the sponge within the inner cavity prior to use of the cap. The inner cavity comprises at least one thread on an inner sidewall surface of the sidewall. The cap thread is sufficient to interlock with the mating feature of the needleless connector, the cap thread does not correspond to the mating feature of the needleless connector.

In accordance with another aspect of the present invention, at least one of a major diameter, a minor diameter, a pitch, a thread section profile, and a number of threads of the cap thread does not correspond to the mating feature of the needleless connector.

In accordance with another aspect of the present invention, a portion of the side wall forming the open bottom comprises an inner sidewall surface forming the opening to the inner cavity such that the open bottom does not form an airtight seal with an outer surface of the needleless connector when the needleless connector is securely engaged with the housing.

In accordance with another aspect of the present invention, the open bottom formed by said sidewall of the housing is not flat such that an exit space exists between a flat surface and the bottom of the housing, whereby venting of the disinfection sponge occurs through the opening to the inner cavity, essentially around an outside of the mating feature of the needleless connector and via the exit space to an outside of the cap housing.

In accordance with another aspect of the present invention, the open bottom formed by the sidewall of the housing includes an irregular bottom inner sidewall surface with one or more divots configured such that the opening to the inner cavity does not form an airtight seal with an outer surface of the needleless connector, whereby venting of the disinfection sponge occurs through the opening to the inner cavity, essentially around an outside of the mating feature of the needleless connector and via at least one of the divots to an outside of the cap housing.

In accordance with another aspect of the present invention, the housing comprises a flared lower portion formed at the open bottom comprising one or more divots regularly or randomly spaced along bottom inner sidewall surface defining the opening to the inner cavity.

In accordance with another aspect of the present invention, the cap thread comprises an extended portion extending below the open bottom formed by the sidewall such that an escape space exists between a surface of top portion of the needleless connector and the open bottom when the cap thread interlocks with the needleless connector such that the extended portion contacts top portion of the needleless connector, whereby venting of the disinfection sponge occurs through the opening to the inner cavity, essentially around an outside of the mating feature of the needleless connector and via the escape space to an outside of the cap housing.

In accordance with another aspect of the present invention, a portion of the side wall forming the open bottom comprises a flared bottom portion having an inner sidewall surface forming the opening to the inner cavity such that the open bottom does not form an airtight seal with an outer surface of the needleless connector when the needleless connector is securely engaged with the housing, whereby venting of the disinfection sponge occurs through the opening to the inner cavity, essentially around an outside of the mating feature of the needleless connector, and between the inner wall surface of the flared bottom portion and the outer surface of the needleless connector to an outside of the cap housing.

In accordance with another aspect of the present invention, the open bottom formed by the sidewall of said housing is essentially flat.

In accordance with another aspect of the present invention, the open bottom formed by said sidewall of the housing is not flat such that an exit space exists between a flat surface and the bottom of said housing.

In accordance with another aspect of the present invention, the inner cavity comprises an upper region terminating in a closed top, and a lower region terminating in an opening to the inner cavity, the lower region comprises the cap thread, and the upper region comprises protrusions into the inner cavity configured to contact and/or engage the sponge.

In accordance with another aspect of the present invention, the sidewall comprises an inner sidewall surface including a plurality of sections between the cap thread, each of the sections having a slope with respect to the longitudinal axis of the housing of the cap. At least one of the sections forming the open bottom expands away from the longitudinal axis to form the flared bottom portion.

In accordance with another aspect of the present invention, the inner cavity comprises an upper region terminating in a closed top, and a lower region terminating in the opening to the inner cavity. The inner sidewall surface comprises a transition section having a linear or curved surface where the inner sidewall surface transitions from the lower region to the upper region such that cross sectional area at bottom of the transition section in the lower region is greater than cross sectional area at top of the transition section in the upper region.

In accordance with another aspect of the present invention, the sponge is secured from being displaced into the upper region when the cap thread interlocks with the mating feature of the needleless connector, such that the sponge maintains contact with the needleless connector and remains away from an inner surface of the closed top.

In accordance with another aspect of the present invention, the opening to the inner cavity formed by the inner sidewall surface of the bottom portion is essentially circular and comprises an opening diameter, and the opening diameter is larger than a flange diameter of the needleless connector, such that said opening diameter causes a venting gap between the inner sidewall surface of the housing and the needleless connector, whereby the opening to the inner cavity comprises the venting gap and the venting of the disinfection sponge occurs through the opening to the inner cavity, essentially around the outside of the mating feature of the needleless connector and via the venting gap, to the outside of the cap housing.

In accordance with another aspect of the present invention, the sidewall comprises the inner sidewall surface in the lower region including a plurality of sections between the cap thread, each of the sections having essentially the same slope with respect to the longitudinal axis of the housing of the cap, and at least one of the sections forming the open bottom, the at least one of the sections expanding away from the longitudinal axis to form the flared bottom portion.

In accordance with another aspect of the present invention, at least one cap thread on the inner sidewall surface of the sidewall comprises a protrusion formed on a least a portion of the cap thread to facilitate the interlocking with the mating feature of the needleless connector.

In accordance with another aspect of the present invention, at least a portion of at least one cap thread comprises a non-engaging portion that does not engage the mating feature of the needleless connector.

In accordance with another aspect of the present invention, the cap thread comprises at least one interlocking portion formed on a least a portion of the cap thread to facilitate interlocking with the mating feature of the needleless connector, and at least one non-engaging portions that does not engage the mating feature of the needleless connector.

In accordance with another aspect of the present invention, a device comprising a strip, and a plurality of disinfection caps according to exemplary embodiments of the present invention disposed on said strip.

In accordance with an exemplary implementation of the present invention, the strip of the device is essentially flat and comprises a plurality of sections separated by perforations in the strip, each of the sections comprising at least one of the plurality of the disinfection caps disposed thereon, whereby the perforations facilitate detachment at the perforations of at least one of said sections with the at least one disinfection cap disposed thereon.

In accordance with another exemplary implementation of the present invention, the strip comprises the removable cover for the plurality of the disinfection caps disposed thereon, whereby each cap of the plurality of caps is attached to the strip at the bottom of the cap and is peelable off the strip uncovering the opening to the inner cavity of the cap when peeled off said strip.

In accordance with yet another exemplary implementation of the present invention, the strip is double-sided comprising opposing sides each having a plurality of disinfection caps disposed thereon.

In accordance with an alternative exemplary implementation of the present invention, the strip comprises a plurality of prongs attached to, and extending away from, the surface of the strip, whereby each cap of said plurality of caps is removably attached to the strip by one of the prongs connected to exterior surface of the closed top of the cap.

In accordance with yet another exemplary implementation of the present invention, the device comprises an attachment portion for selectively placing the strip having the caps attached thereto on an IV pole.

In accordance with an exemplary embodiment of the present invention, a multiple start thread pattern for use in a medical device connector comprises: a first start thread path wherein the first start thread path has a major profile, a minor profile, a pitch, and a first thread section profile; at least a second start thread path wherein the second start thread path has a major profile, a minor profile, a pitch, and a second thread section profile. The first thread section profile and the second thread section profile are different.

In accordance an exemplary implementation of the present invention, first and second start thread paths have equivalent pitches and are configured to interface with a complimentary thread of a secondary medical device connector having a major profile and a substantially equivalent pitch to the pitches of the first and second start thread paths.

In accordance with another exemplary implementation of the present invention when the complimentary thread is engaged to the first and second start thread paths a first helical void is formed by the space enclosed by the complimentary thread and the first start thread path and a second helical void is formed by the space enclosed by the complimentary thread and the second start thread path. The second helical void is larger than the first helical void.

In accordance with yet another exemplary implementation of the present invention, the first start thread path and said second start thread path further comprise respective root section profiles and respective crest section profiles. The respective root section profiles are substantially similar and the respective crest section profiles are substantially different.

In accordance with yet another exemplary implementation of the present invention, the first start thread path and the second start thread path form a female thread pattern and the complimentary thread of the secondary medical device connector has a male thread pattern.

In accordance with yet another exemplary implementation of the present invention, the first start thread path and the second start path form a male thread pattern and the complimentary thread of the secondary medical device connector has a female thread pattern.

In accordance with yet another exemplary implementation of the present invention, the second start thread path interfaces with the complimentary thread substantially tangentially.

In accordance with yet another exemplary implementation of the present invention, the first start thread path interfaces with the complimentary thread to substantially engage the complimentary thread.

In accordance with yet another exemplary implementation of the present invention, the first and second start thread paths have substantially equivalent pitches.

In accordance with an exemplary embodiment of the present invention, a cap which incorporates the multiple start thread pattern comprises an inner cavity and an airflow path from a proximal end of the cap to the inner cavity is formed by the first and second helical voids when the complimentary thread is engaged to the multiple start thread pattern.

In accordance with an exemplary implementation of the present invention, the cap further comprises a disinfection agent retention member retained in the inner cavity essentially at a distal end of the cap.

In accordance with another exemplary implementation of the present invention, the cap further comprises an inner surface having the first and second start thread paths and receiving the secondary medical device connector.

In accordance with yet another exemplary implementation of the present invention, the inner surface of the cap forms an essentially frustoconical inner cavity having a larger cross section at the proximal end of the cap.

In accordance with yet another exemplary implementation of the present invention, the inner surface of the cap forms an essentially cylindrical inner cavity having a cross section greater than the major profile of the complimentary thread of the secondary medical device connector.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which:

FIGS. 1A and 1B are cross sectional views of conventional caps for needleless connectors.

FIG. 2 is an illustration of a conventional device for hanging caps on an IV pole.

FIG. 11A is a cross-sectional view of a cap according to yet another exemplary embodiment of the present invention.

FIG. 11B illustrates another view of a cap according to yet another exemplary embodiment of the present invention.

FIG. 14A is an illustration of venting in a cap according to a further exemplary embodiment of the present invention disposed on a medical implement such as a needleless connector.

FIG. 14B illustrates another view of a cap according to a further exemplary embodiment of the present invention.

FIG. 22 is a cross sectional drawing of a conventional female (Luer) lock conical fitting.

FIGS. 25A and 25B illustrate a device according to an exemplary embodiment of the present invention for hanging a plurality of caps on an IV pole.

FIG. 26A illustrates a device according to a further exemplary embodiment of the present invention for hanging a plurality of caps on an IV pole.

FIG. 26B illustrates a device according to still further exemplary embodiment of the present invention for hanging a plurality of caps on an IV pole.

Throughout the drawings, like reference numbers will be understood to refer to like parts, components and structures.

DETAILED DESCRIPTION OF THE EXEMPLARY EMBODIMENTS

Figure 3A:
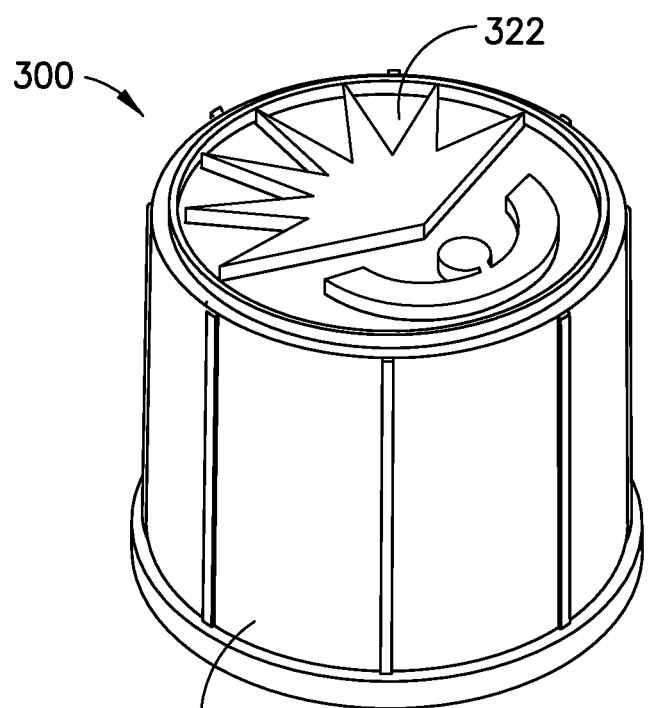
FIGS. 3A and 3B are three-dimensional views of a cap according to an exemplary embodiment of the present invention.
Figure 3B:
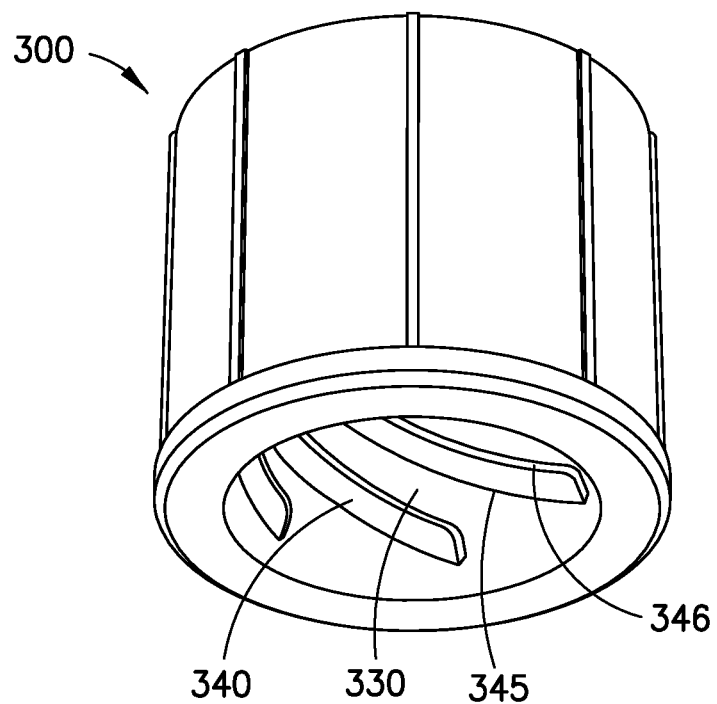
Figure 4A:
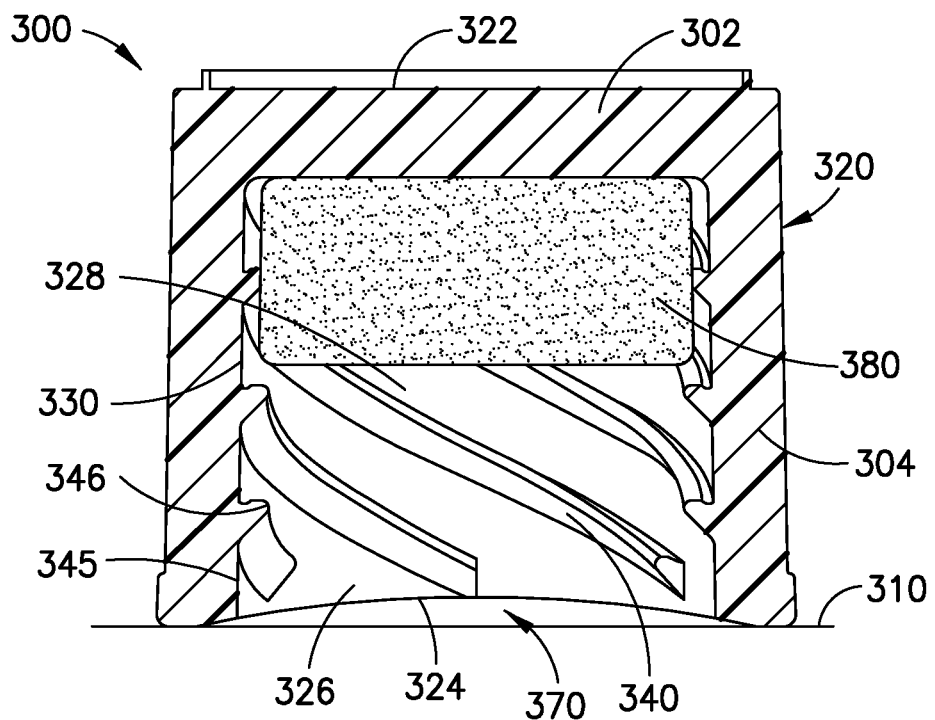
FIG. 4A is a cross sectional view of a cap according to an exemplary embodiment of the present invention.
Figure 4B:
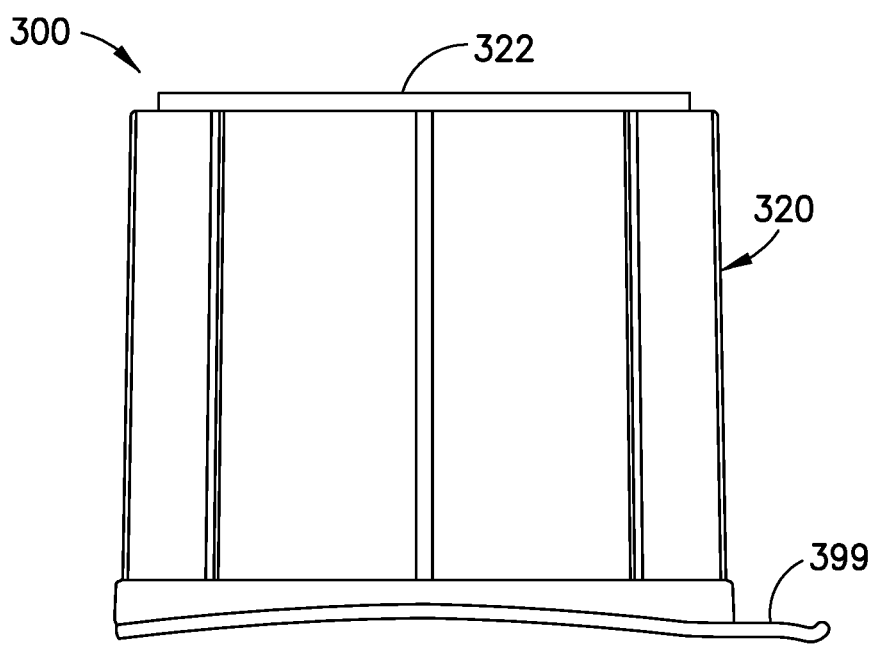
FIG. 4B illustrates another view of a cap according to an exemplary embodiment of the present invention.
Figure 5:
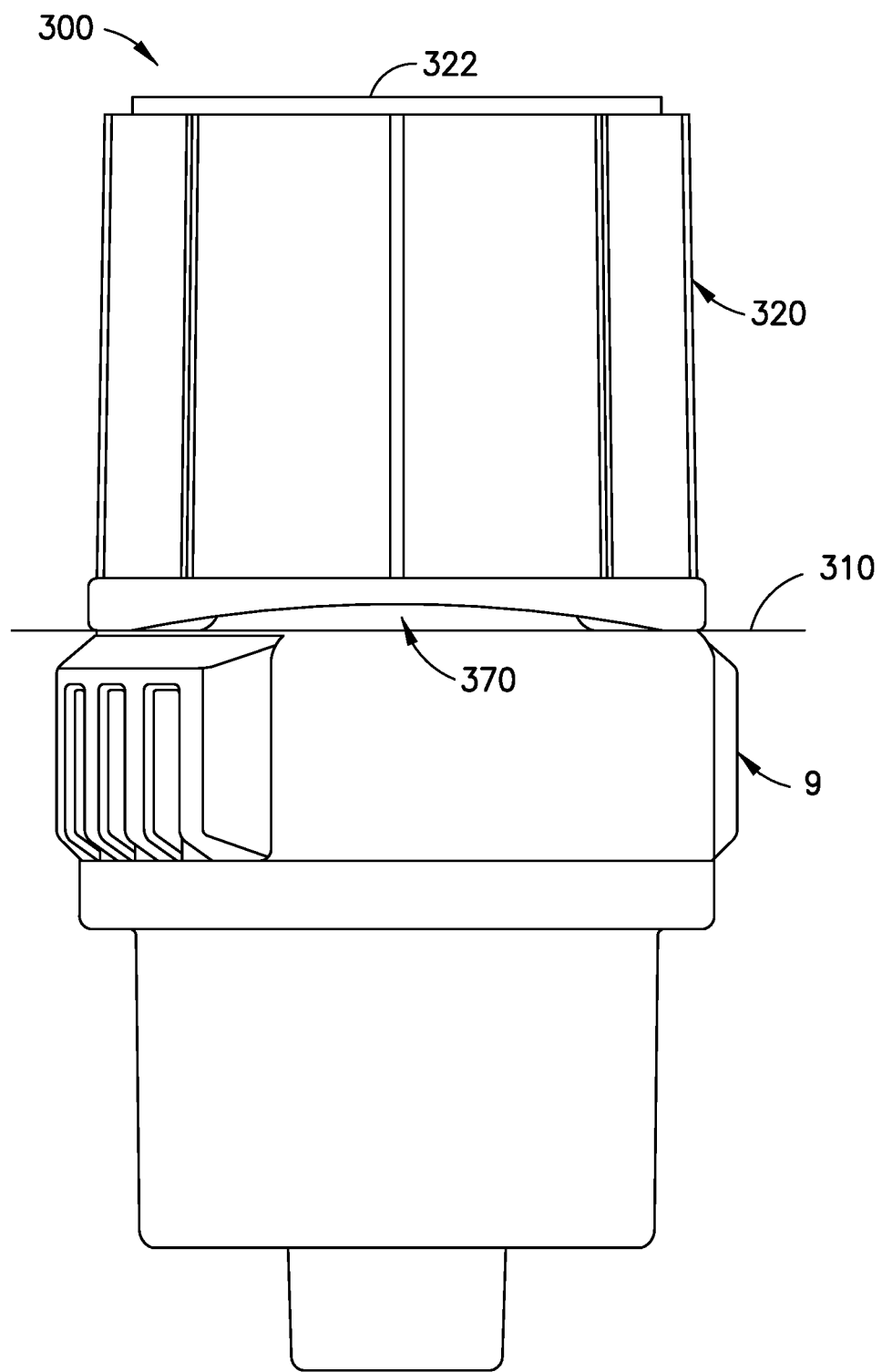
FIG. 5 is an illustration of a cap according to an exemplary embodiment of the present invention disposed on a medical implement such as a needleless connector.

The matters exemplified in this description are provided to assist in a comprehensive understanding of exemplary embodiments of the invention. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

Exemplary embodiments of the present invention provide a disinfection cap that can have an increased venting performance, while using a novel single shot moldable cap design features where disinfection fluid venting can be accomplished by incorporating cap features for (thread major diameter, thread minor diameter, thread pitch, thread section profile and number of threads features) that do not correspond to the mating features on the IV catheter needleless connector hub. The cap's thread minor features grip the needleless connector thread major features causing an interference friction fit between the two parts. These non-corresponding thread features result in significant spiral venting paths around the outside of the needleless connector thread major sections between the cap and IV hub. These paths lead from the alcohol soaked disinfection sponge in the upper section of the cap, spirally down the inner diameter of the cap and vent out of the bottom of the cap to atmosphere.

As would be readily appreciated by skilled artisans in the relevant art, in the description that follows, definition of "a feature that does not correspond to the mating feature" is: a feature that is not identical to the mating feature in all essentials or respects. Definition of "identical" is: outside of industry average tolerance ranges for injection moldable plastic parts and injection moldable plastic parts assemblies. Also, it is to be noted that, while descriptive terms such as "tip", "hub", "thread", "sponge", "protrusion", "slope", and others are used throughout this specification to facilitate understanding, it is not intended to limit any components that can be used in combinations or individually to implement various aspects of the embodiments of the present invention.

Furthermore, the cap thread feature sizing can be optimized in relation to the needleless connector thread or mating features as to maximize the cap's venting rate performance while still meeting other product requirements. Manufacturing injection demolding can be accomplished via spiral ejection of the parts or rotating mold core. Thus, two shot injection and/or plastic parts assembly is not required with design concepts according to exemplary embodiments of the present invention.

Referring now to the drawings, wherein like reference numerals designate identical or corresponding parts throughout the several views, embodiments of the present invention are described as follows.

According to an exemplary implementation of the embodiments of the present invention as illustrated in FIGS. 3A, 3B, and 4-7, a cross thread disinfection cap 300 can fit onto a tip or hub 12 of needleless connector 9 and comprises housing 302 comprising: a closed top 322; an essentially cylindrical sidewall 304 with an outer sidewall surface 320; and an open bottom 324 with an opening 326 to an inner cavity 328 within housing 302 for receiving tip of a needleless connector 9. The bottom 324 formed by sidewall 304 of housing 302 is not flat such that space 370 exists between a flat surface 310 and bottom 324 of cap 300. The inner cavity 328 accommodates an alcohol soaked disinfection sponge 380 and has threads (or mating feature) 340 on inner sidewall surface 330 of sidewall 304. The diameter (major diameter 345 and/or minor diameter 346) of threads 340 of the cap 300 does not correspond to the thread (or mating feature) 13 of the needleless connector 9. A removable cover 399 can be attached to bottom 324 of cap 300 to seal inner cavity 328 including disinfection sponge 380.

Figure 6:
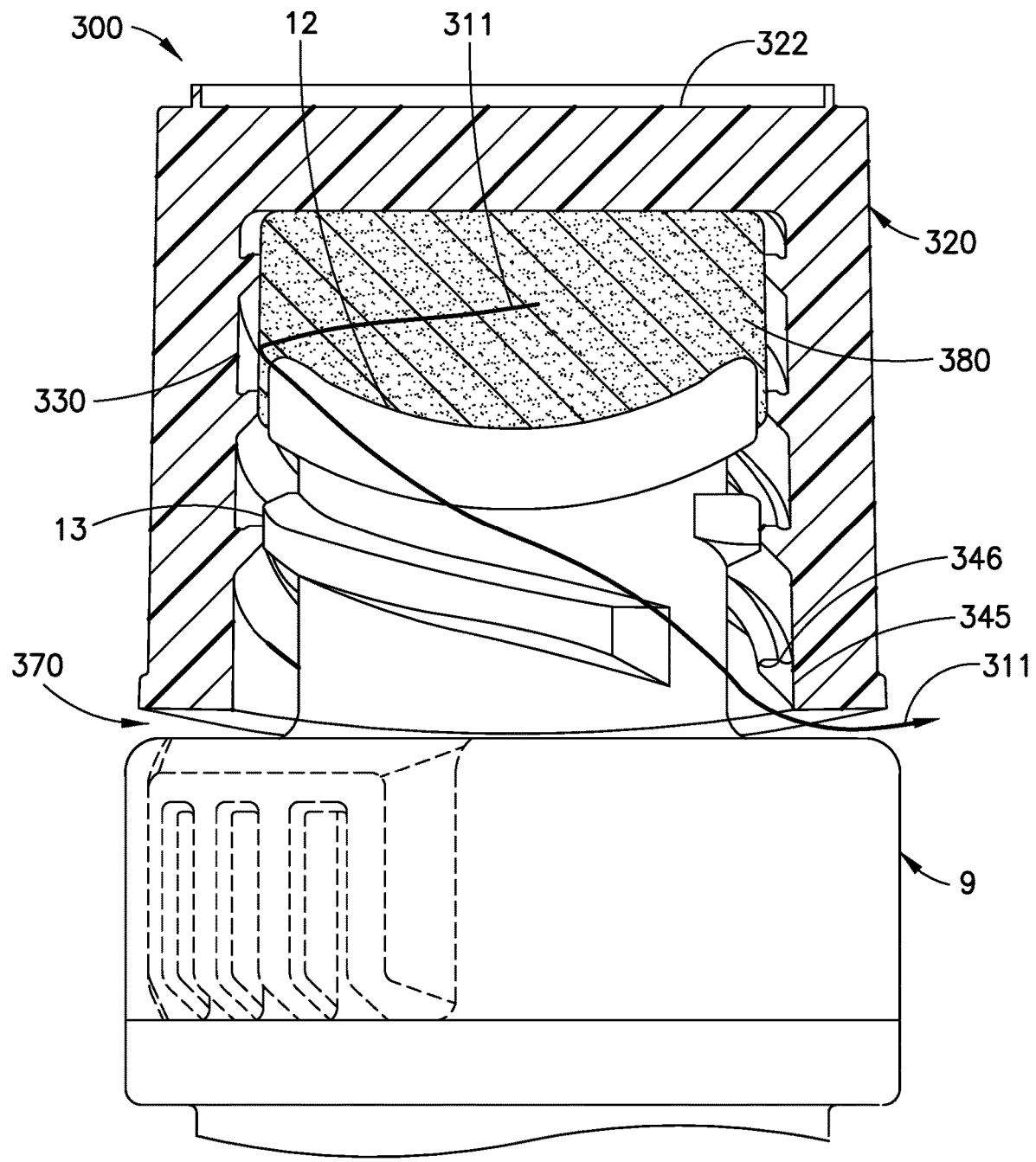
FIG. 6 is an illustration showing a cross-sectional view of a cap according to an exemplary embodiment of the present invention disposed on a medical implement such as a needleless connector.
Figure 7:
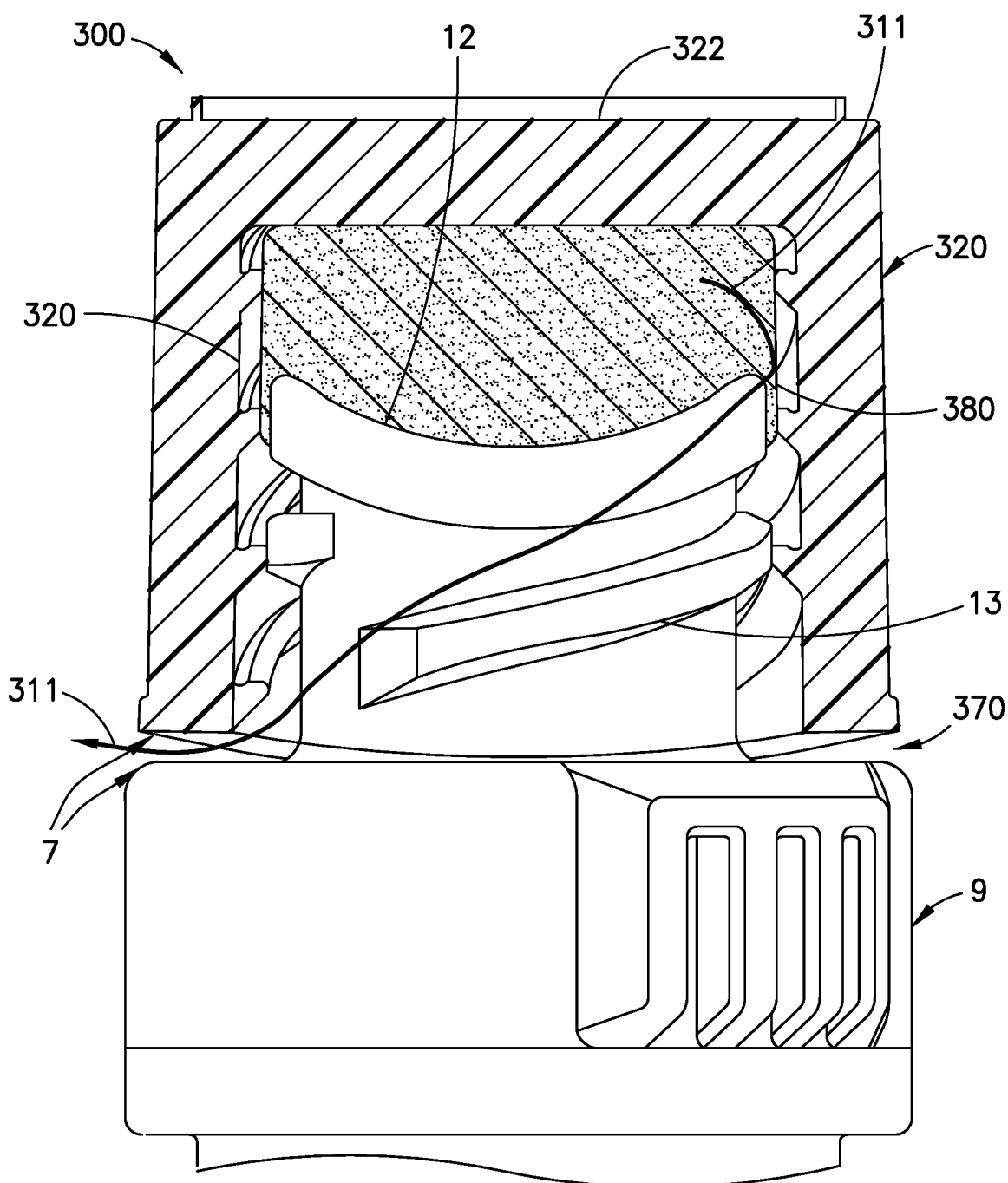
FIG. 7 is an illustration of venting in a cap according to an exemplary embodiment of the present invention when disposed on a medical implement such as a needleless connector.
Figure 8A:
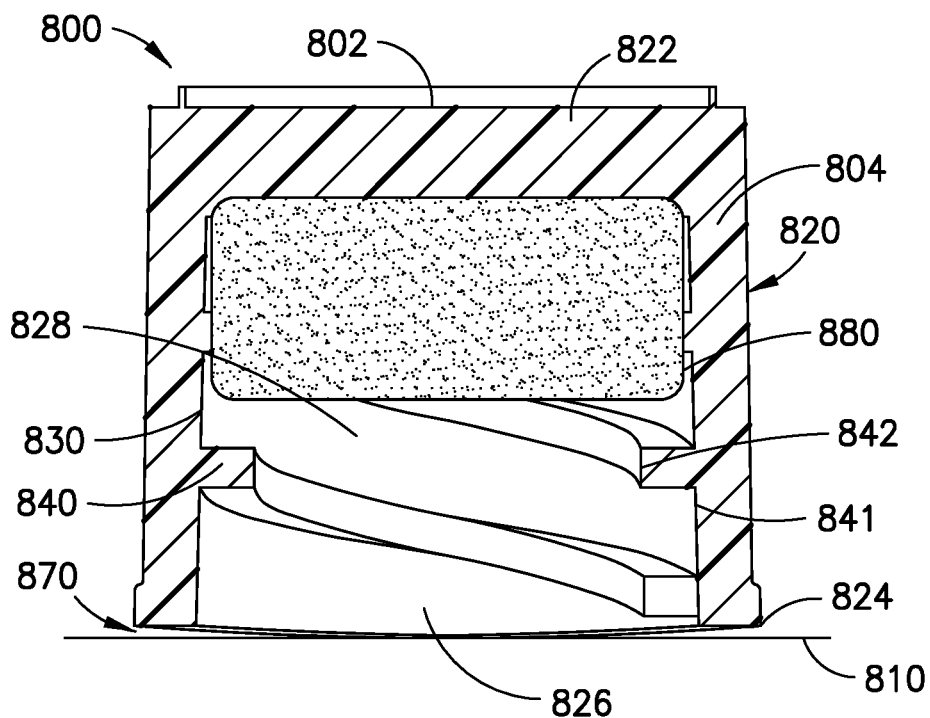
FIG. 8A is a cross sectional view of a cap according to another exemplary embodiment of the present invention.
Figure 8B:
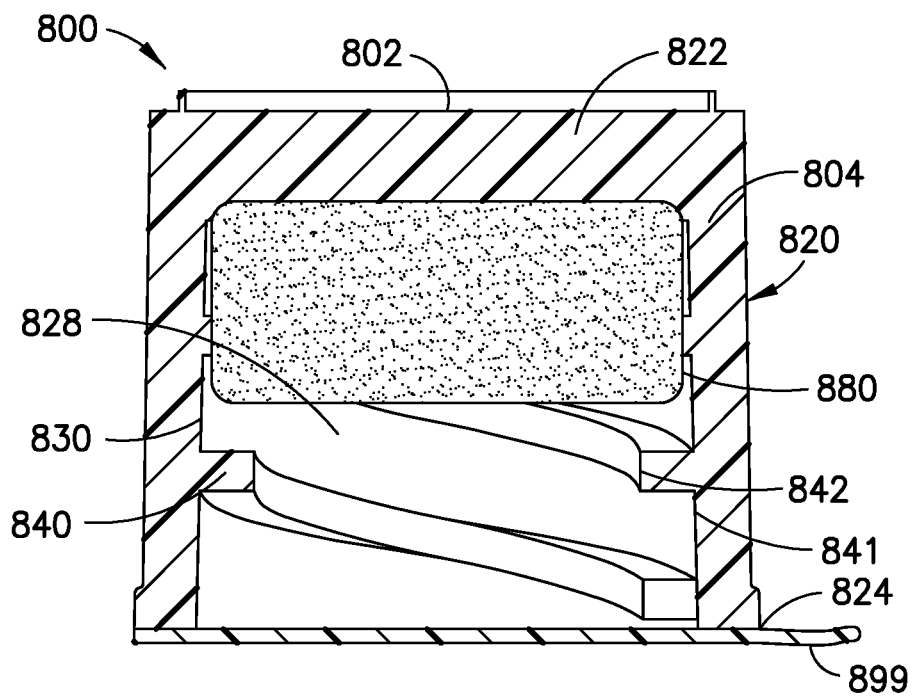
FIG. 8B illustrates another view of a cap according to another exemplary embodiment of the present invention.
Figure 9:
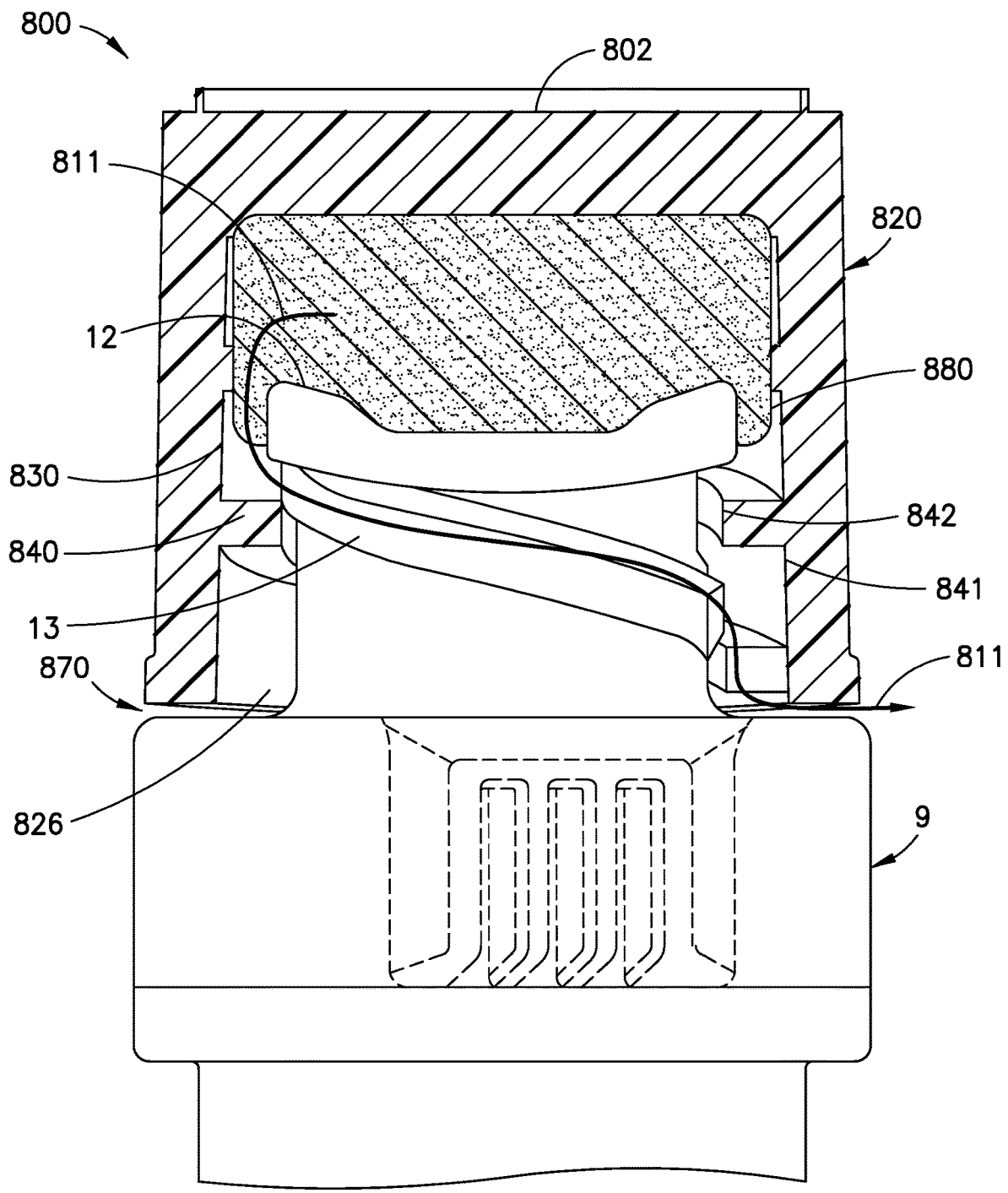
FIG. 9 is an illustration of venting in a cap according to another exemplary embodiment of the present invention disposed on a medical implement such as a needleless connector.

In addition, as further illustrated in FIGS. 6 and 7, according to an exemplary implementation, thread pitch, thread section profile, and/or number-of-threads of cap 300 do not correspond to the thread 13 of the needleless connector 9. Since the threads 340 of the cap 300 do not correspond to the thread 13 of the needleless connector 9, venting 311 of the alcohol soaked disinfection sponge 380 occurs through the one opening 326 to the inner cavity 328, essentially around the outside of threads 13 of the needleless connector 9 and via space 370 to the outside (atmosphere) of the cap housing 302.

According to another exemplary implementation of the embodiments of the present invention as illustrated in FIGS. 8A-10, a thread major gap disinfection cap 800 can fit onto a tip 12 of needleless connector 9 and comprises housing 802 comprising: a closed top 822; an essentially cylindrical sidewall 804 with an outer sidewall surface 820; and an open bottom 824 with an opening 826 to an inner cavity 828 within housing 802 for receiving tip of a needleless connector 9. The bottom 824 formed by sidewall 804 of housing 802 is not flat such that space 870 exists between a flat surface 810 and bottom 824 of cap 800. The inner cavity 828 accommodates an alcohol soaked disinfection sponge 880 and has threads 840 on inner sidewall surface 830 of sidewall 804. A removable cover 899 can be attached to bottom 824 of cap 800 to seal inner cavity 828 including disinfection sponge 880

The pitch of threads 840 corresponds to the pitch of thread 13 of needleless connector 9. However, the profile (major profile 841 and/or minor profile 842) of threads 840 of the cap 800 does not correspond to the thread 13 of the needleless connector 9. Since the threads 840 of the cap 800 do not correspond to the thread 13 of the needleless connector 9, venting 811 of the alcohol soaked disinfection sponge 880 occurs through the one opening 826 to the inner cavity 828, essentially around the outside of threads 13 of the needleless connector 9 and via space 870 to the outside (atmosphere) of the cap housing 802.

Figure 12:
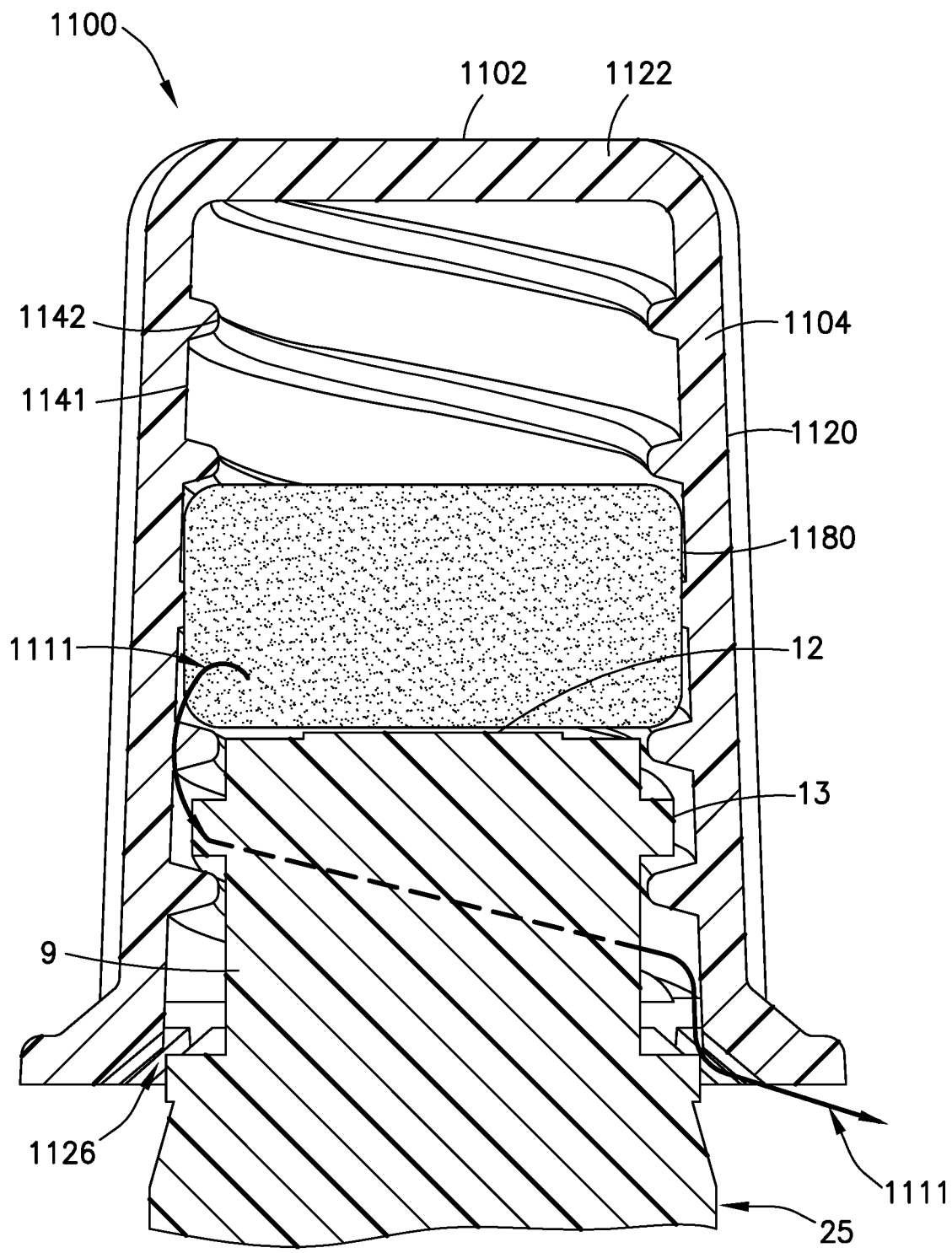
FIG. 12 is an illustration showing a cross-sectional view of a cap according to yet another exemplary embodiment of the present invention disposed on a medical implement such as a needleless connector.

According to yet another exemplary implementation of the embodiments of the present invention illustrated in FIGS. 11A, 11B, and 12, a thread-castellartions-design disinfection cap 1100 can fit onto a tip 12 of needleless connector 9 and comprises housing 1102 comprising: a closed top 1122; an essentially cylindrical sidewall 1104 with an outer sidewall surface 1120; and an open bottom 1124 with an opening 1126 to an inner cavity 1128 within housing 1102 for receiving tip 12 of a needleless connector 9. The bottom 1124 formed by sidewall 1104 of housing 1102 includes an irregular bottom inner sidewall surface 1132 with divots 1136 such that the opening 1126 does not form an airtight seal with outer surface 25 of needleless connector 9.

In an exemplary implementation, housing 1102 comprises a flared lower portion 1190 formed at bottom 1124, which includes divots 1136. Any number, one or more, of divots 1136 can be regularly or randomly spaced along bottom inner sidewall surface 1132. The inner cavity 1128 accommodates an alcohol soaked disinfection sponge 1180, similarly to an example of FIG. 10, such that sponge 1180 contact and disinfects at least tip 12 of needleless connector 9. Inner cavity 1128 comprises threads 1140 on inner sidewall surface 1130 of sidewall 1104.

The pitch of threads 1140 corresponds to the pitch of thread 13 of needleless connector 9. However, the profile (major profile 1141 and/or minor profile 1142) of threads 1140 of the cap 1100 does not correspond to the thread 13 of the needleless connector 9. Since the threads 1140 of the cap 1100 do not correspond to the thread 13 of the needleless connector 9, venting 1111 of the alcohol soaked disinfection sponge 1180 occurs essentially around the outside of threads 13 of the needleless connector 9, and through one or more divots 1136 of opening 1126 to the inner cavity 1128, to the outside (atmosphere) of the cap housing 1102. The bottom 1124 formed by sidewall 1104 of housing 1102 can be, but does not have to be, essentially flat (in contrast to exemplary embodiment of FIG. 10 where space 870 exists between a flat surface 810 and bottom 824 of cap 800). A removable cover 1199 can be attached to bottom 1124 of cap 1100 to seal inner cavity 1128 including disinfection sponge 1180.

Figure 13:
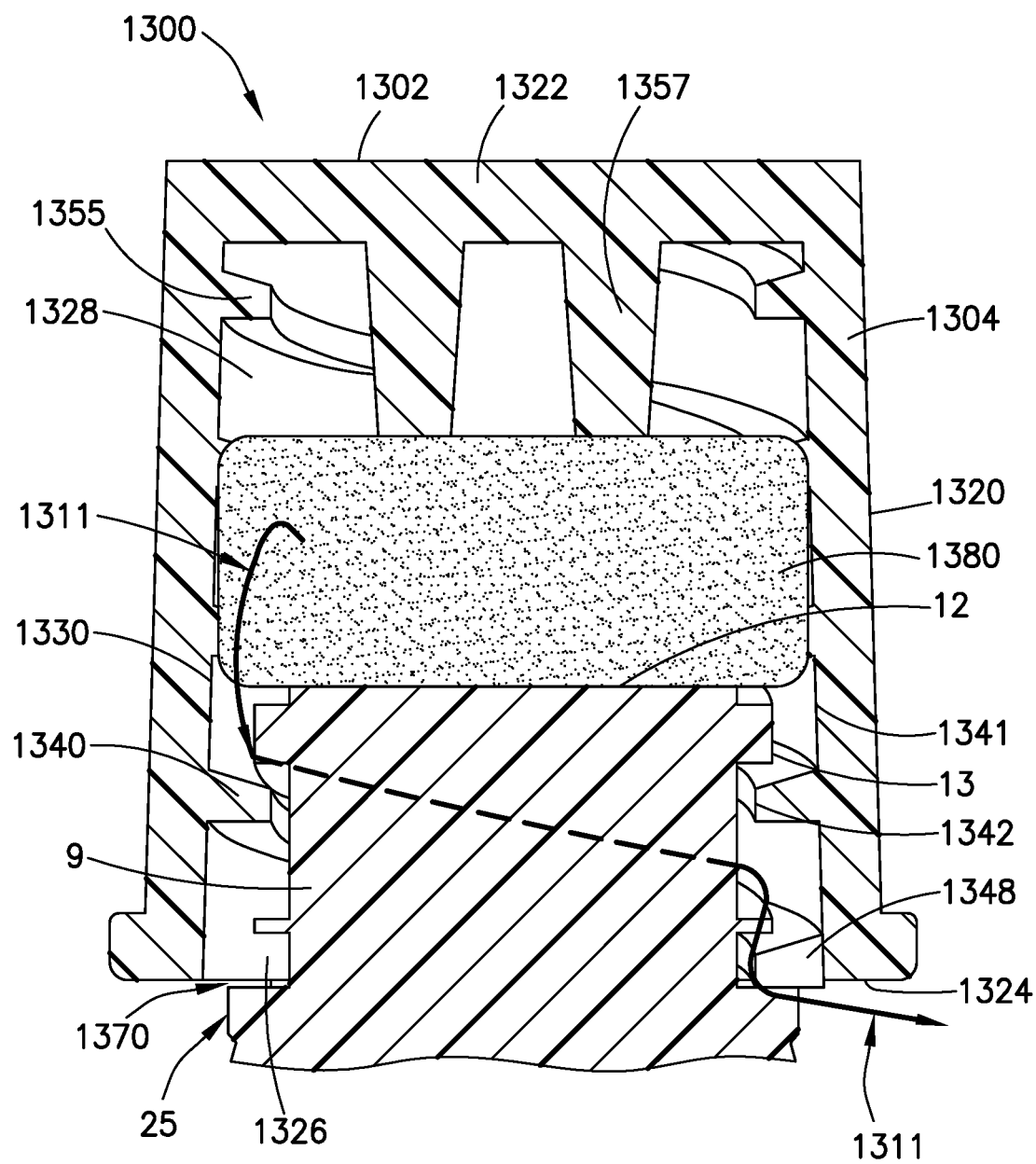
FIG. 13 is an illustration showing a cross-sectional view of a cap according to a further exemplary embodiment of the present invention disposed on a medical implement such as a needleless connector.
Figure 15:
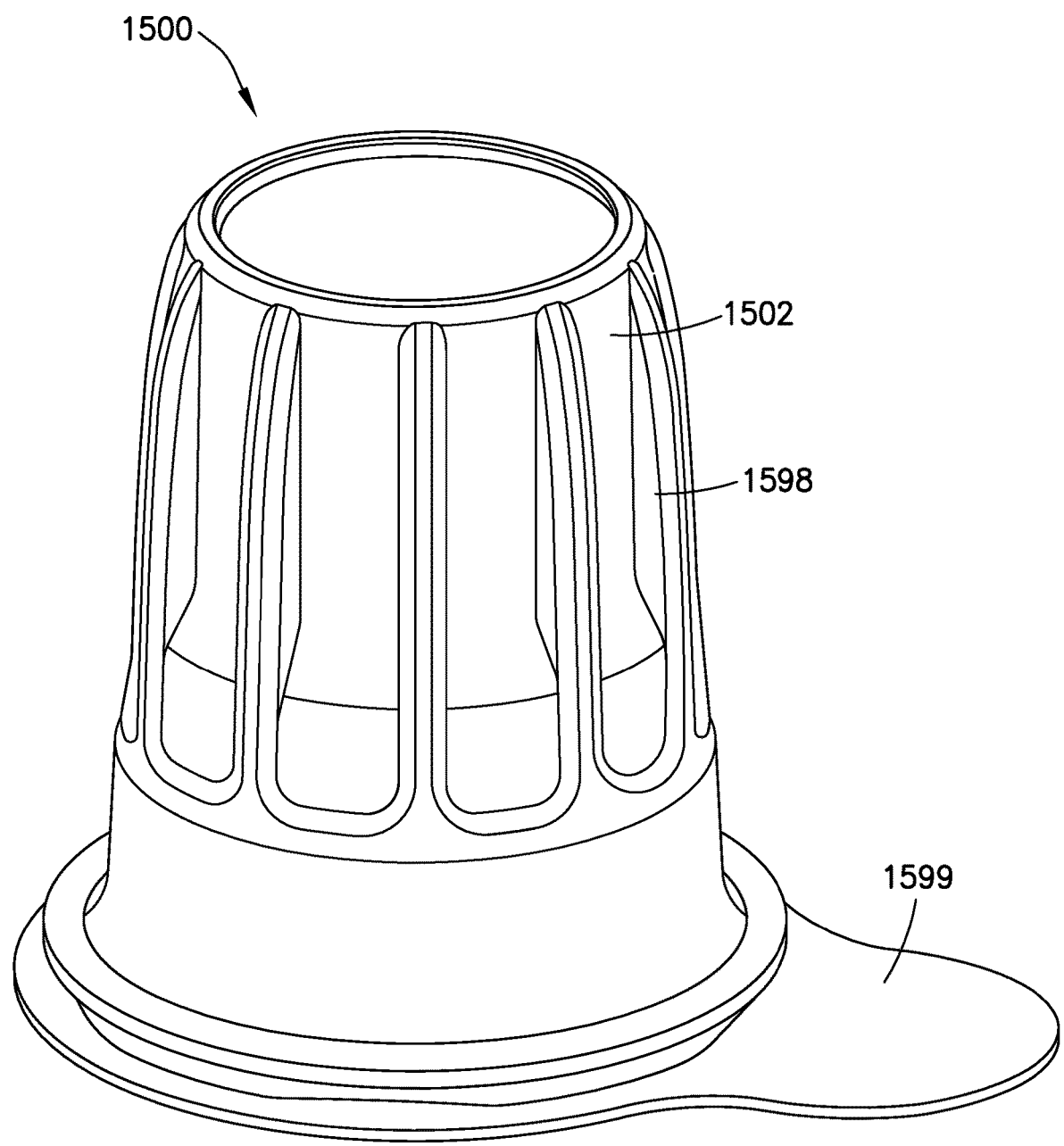
FIG. 15 is a three-dimensional view of a cap according to still further exemplary embodiment of the present invention.

According to yet further exemplary implementation of the embodiments of the present invention as illustrated in FIGS. 13, 14A and 14B, an extended-thread-design gap disinfection cap 1300 can fit onto a tip 12 of needleless connector 9 and comprises housing 1302 comprising: a closed top 1322; an essentially cylindrical sidewall 1304 with an outer sidewall surface 1320; and an open bottom 1324 with an opening 1326 to an inner cavity 1328 within housing 1302 for receiving tip of a needleless connector 9. The inner cavity 1328 comprises an upper region 1312 and a lower region 1314, and accommodates an alcohol soaked disinfection sponge 1380. Lower region 1334 comprises engaging threads 1340 on inner sidewall surface 1330 of sidewall 1304 for engaging thread 13 of needleless connector 9. Threads 1340 include an extended portion 1348, which extends below bottom 1324 formed by sidewall 1304 of housing 1302 such that space 1370 exists between a surface 1310 of top portion 25 of needleless connector 9 and bottom 1324 of cap 1300 when cap 1300 is installed onto connector 9 such that extended portion 1348 contacts top portion 25 of needleless connector 9.

In an exemplary implementation, upper region 1312 can comprise protrusions 1355 from inner sidewall surface 1330, and/or protrusions 1357 from inner surface of top 1322, engaging or contacting disinfection sponge 1380. The pitch of engaging threads 1340 corresponds to the pitch of thread 13 of needleless connector 9. However, the profile (major profile 1341 and/or minor profile 1342) of engaging threads 1340 of the cap 1300 does not correspond to the thread 13 of the needleless connector 9. Since engaging threads 1340 of cap 1300 do not correspond to the thread 13 of the needleless connector 9, venting 1311 of the alcohol soaked disinfection sponge 1380 occurs through the one opening 1326 to the inner cavity 1328, essentially around the outside of threads 13 of the needleless connector 9 and via space 1370 to the outside (atmosphere) of the cap housing 1302. In an exemplary implementation, bottom 1324 formed by sidewall 1304 of housing 1302 can be, but does not have to be, essentially flat (in contrast to exemplary embodiment of FIG. 10 where space 870 exists between a flat surface 810 and bottom 824 of cap 800). A removable cover 1399 can be attached to bottom 1324 of cap 1300 to seal inner cavity 1328 including disinfection sponge 1380.

According to still further exemplary implementation of the embodiments of the present invention as illustrated in FIGS. 15-19, a disinfection cap 1500 can fit onto a tip 12 of needleless connector 9 and comprises housing 1502 comprising: a closed top 1522; sidewall 1504 with an outer sidewall surface 1520; and an open bottom 1524 with an opening 1526 to an inner cavity 1528 within housing 1502 for receiving tip of a needleless connector 9. The inner cavity 1528 comprises an upper region 1512 and a lower region 1514, and accommodates an alcohol soaked disinfection sponge 1580. The bottom 1524 formed by sidewall 1504 of housing 1502 includes a flared bottom portion 1590 having an inner sidewall surface 1532 such that the opening 1526 does not form an airtight seal with outer surface 25 of needleless connector 9 when tip of connector 9 is securely engaged at least within lower region 1514 of cavity 1528. A removable cover 1599 can be attached to bottom 1524 of cap 1500 to seal inner cavity 1528 including disinfection sponge 1580.

In an exemplary implementation, opening 1526 to inner cavity 1528 formed by inner sidewall surface 1532 is essentially circular and has an opening diameter 26, which is larger than a flange diameter 1533 of outer surface 25 of needleless connector 9, such that opening diameter 26 causes a venting gap 1527 between inner sidewall surface 1532 and outer surface 25 needleless connector 9.

Lower region 1514 comprises threads 1540 on inner sidewall surface 1530 of sidewall 1504 for engaging thread 13 of needleless connector 9. In an exemplary implementation, upper region 1512 can comprise protrusions 1555 on inner sidewall surface 1530 and/or protrusions (not shown) on inner surface of top 1522 (such as protrusions 1357 illustrated in example of FIG. 13) engaging or contacting disinfection sponge 1580.

The pitch of threads 1540 corresponds to the pitch of thread 13 of needleless connector 9. However, the profile (major profile 1541 and/or minor profile 1542) of threads 1540 of the cap 1500 does not correspond to the thread 13 of the needleless connector 9. Since engaging threads 1540 of cap 1500 do not correspond to the thread 13 of the needleless connector 9, venting 1511 of the alcohol soaked disinfection sponge 1580 occurs essentially around the outside of threads 13 of the needleless connector 9 and through opening 1526 to the inner cavity 1528 to the outside (atmosphere) of the cap housing 1502. In an exemplary implementation, venting 1511 occurs through opening 1526 via venting gap 1527.

Figure 10:
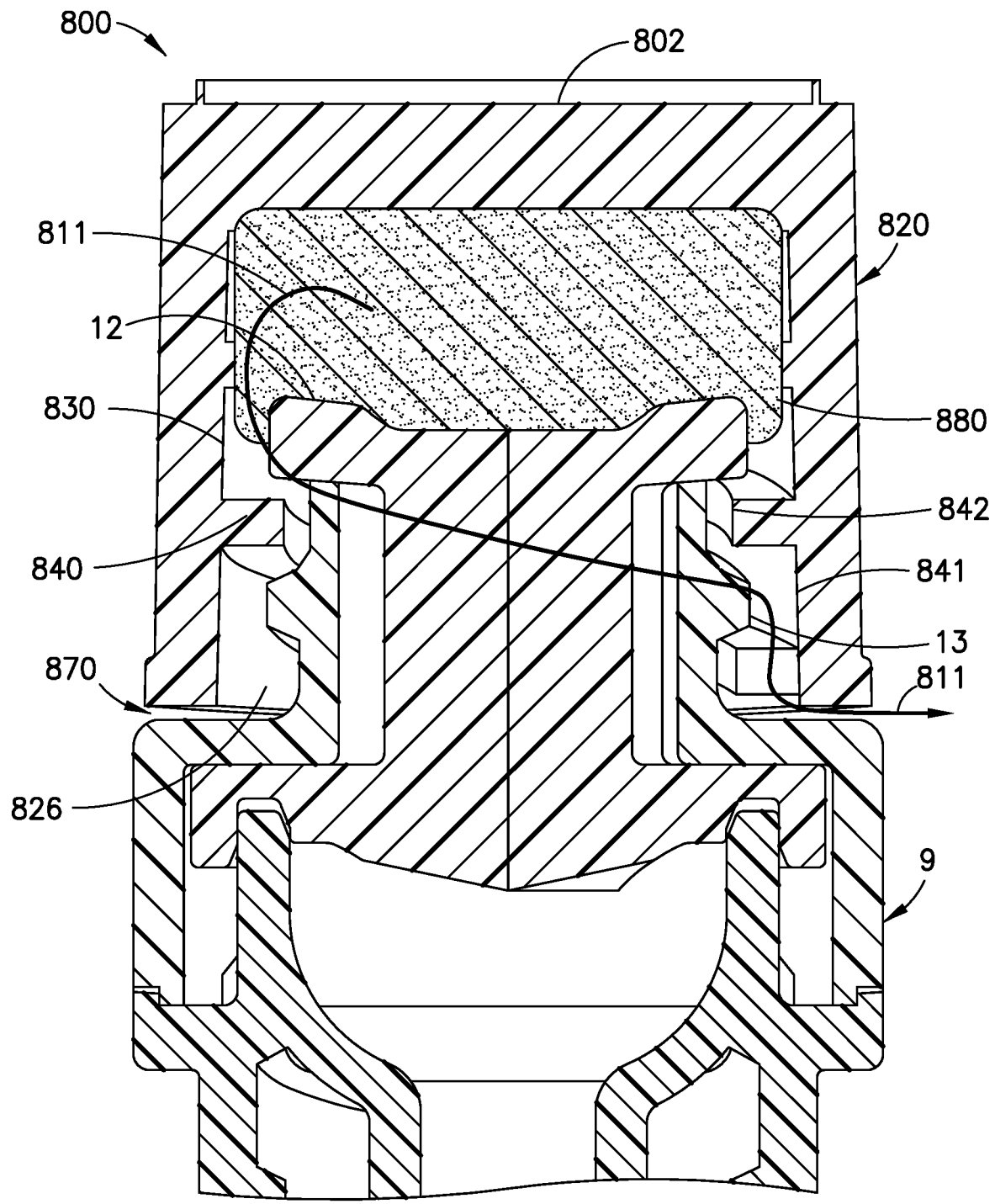
FIG. 10 is an illustration showing a cross-sectional view of a cap according to another exemplary embodiment of the present invention disposed on a medical implement such as a needleless connector.

The bottom 1524 formed by sidewall 1504 of housing 1502 can be, but does not have to be, essentially flat (in contrast to exemplary embodiment of FIG. 10 where space 870 exists between a flat surface 810 and bottom 824 of cap 800).

Figure 16:
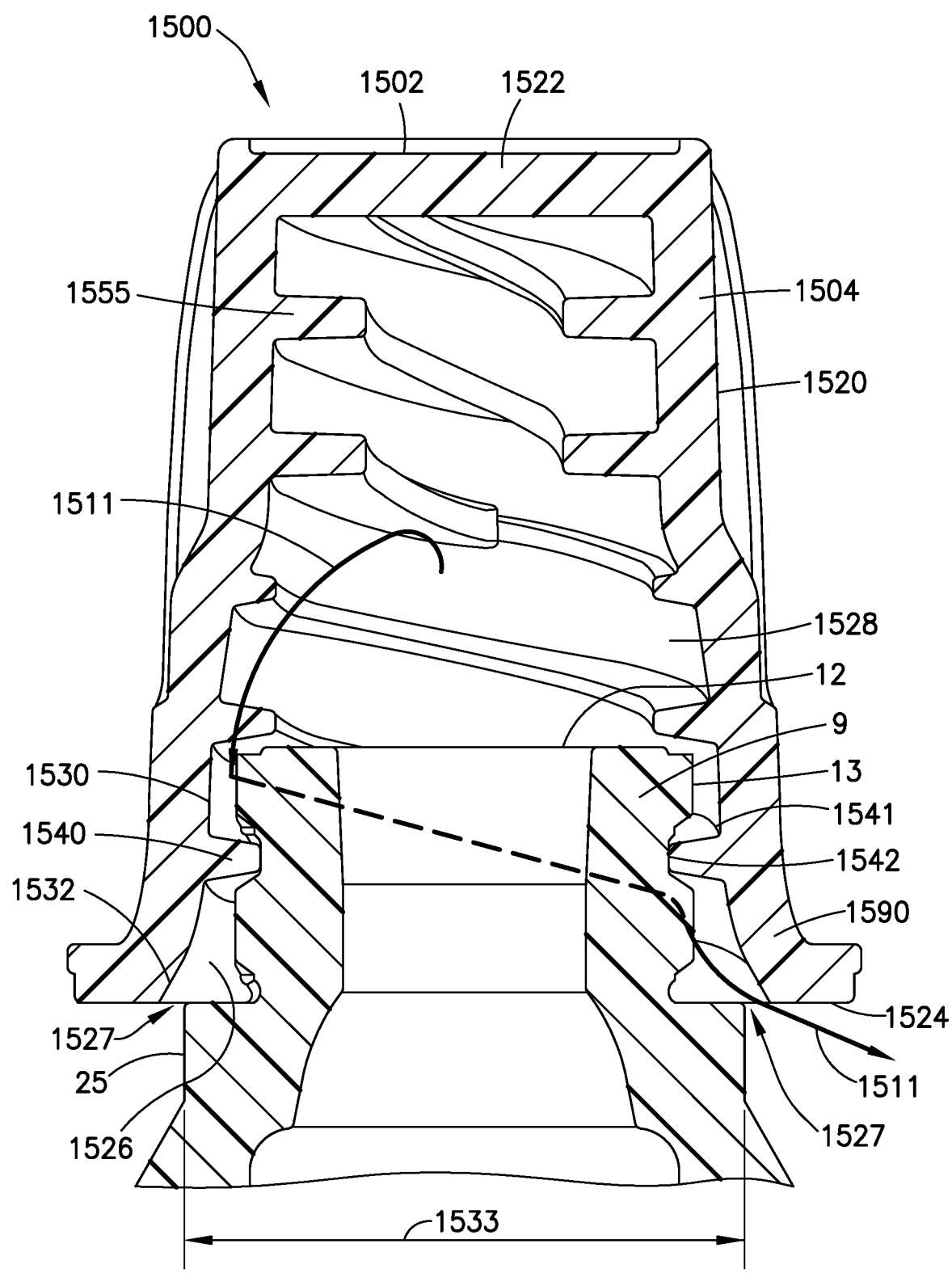
FIG. 16 is an illustration showing a cross-sectional view of a cap according to still further exemplary embodiment of the present invention disposed on a medical implement such as a needleless connector.
Figure 17A:
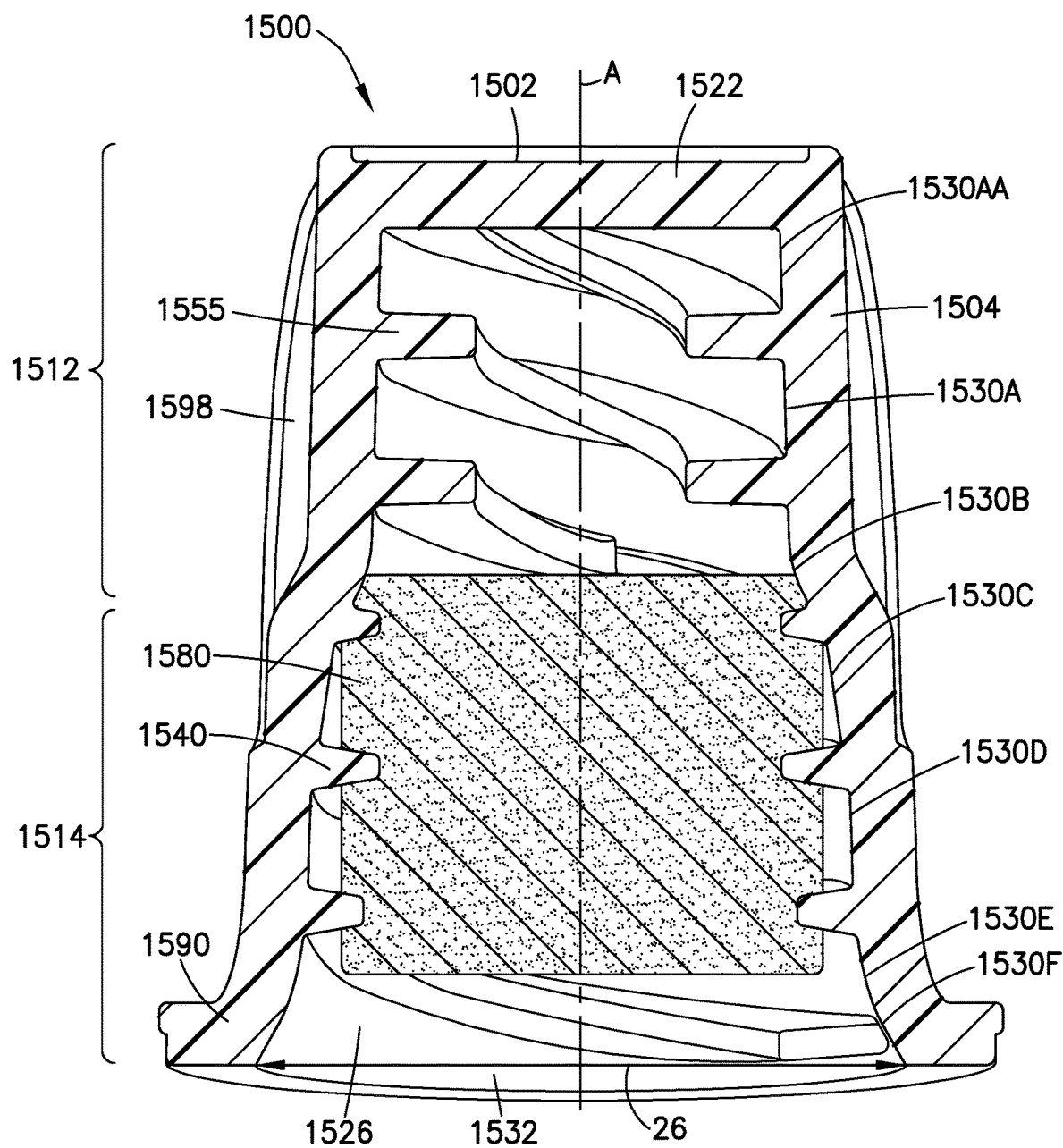
FIG. 17A is a cross-sectional view of a cap according to yet further exemplary embodiment of the present invention.
Figure 17B:
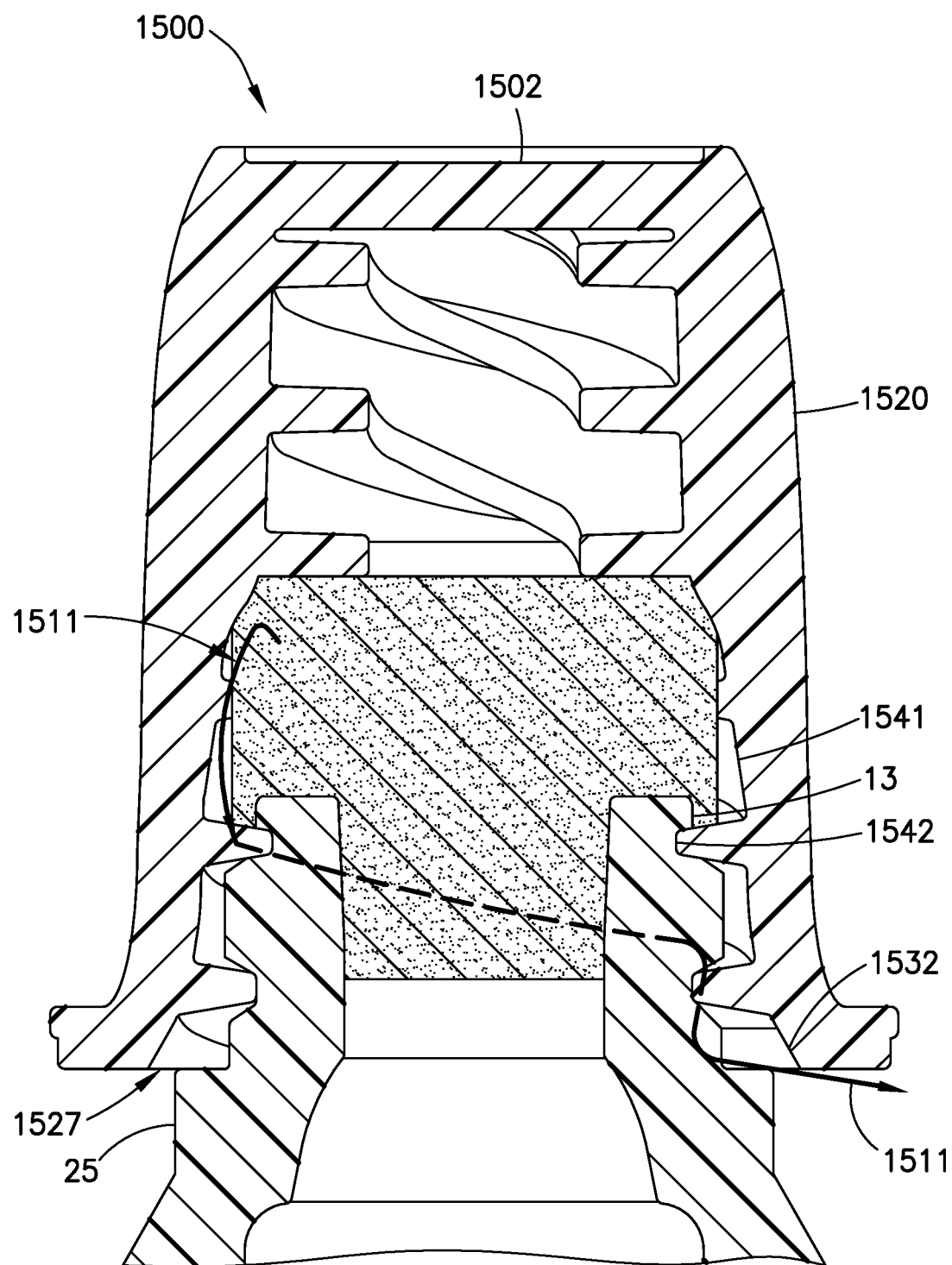
FIG. 17B is an illustration showing a cross-sectional view of a cap according to yet further exemplary embodiment of the present invention disposed on a medical implement such as a needleless connector.
Figure 17C:
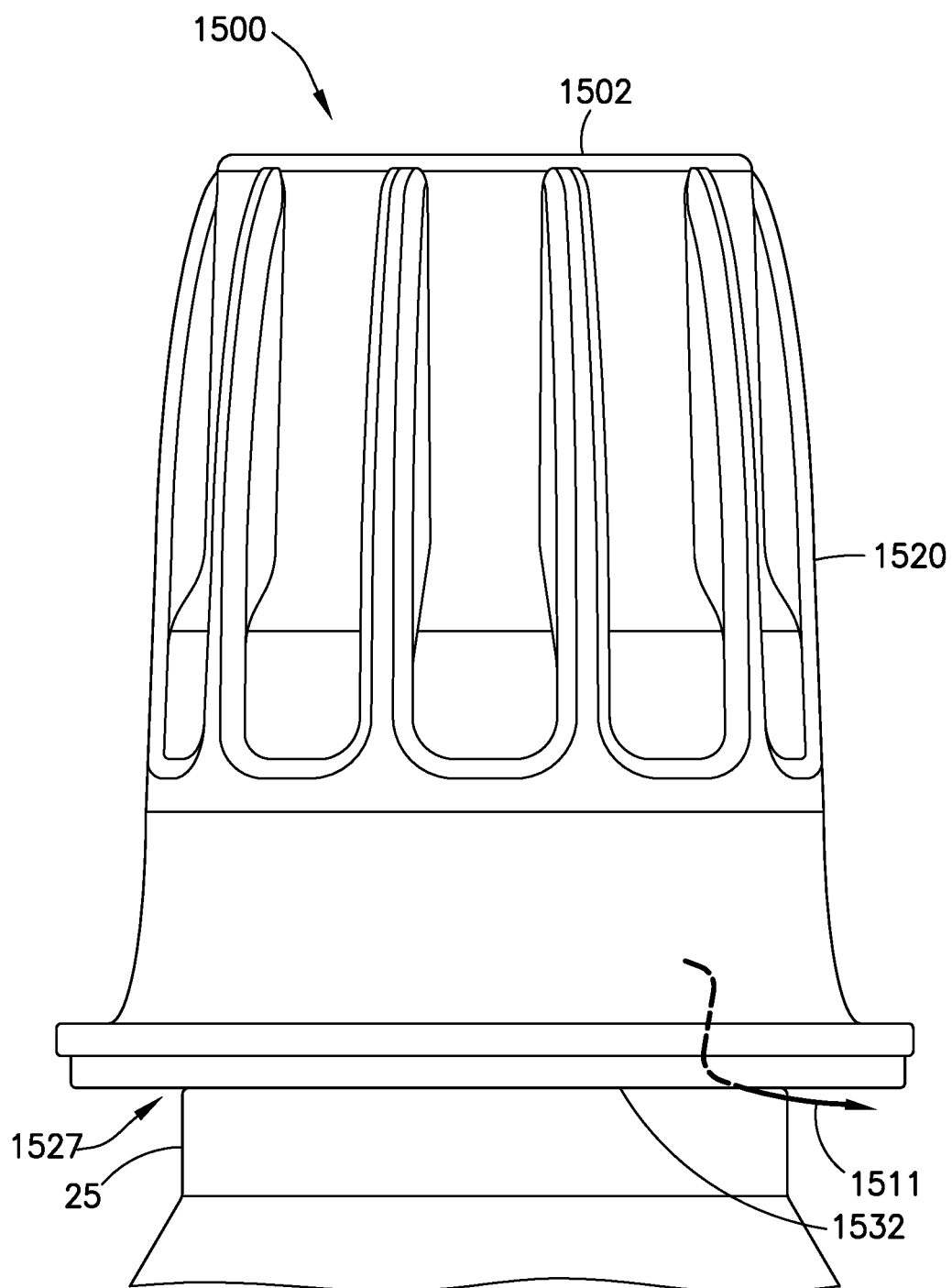
FIG. 17C is an illustration of venting in a cap according to yet further exemplary embodiment of the present invention disposed on a medical implement such as a needleless connector.

According to an exemplary implementation of an embodiment of the invention as illustrated in FIGS. 17A, 17B and 17C, inner sidewall surface 1530 in lower region 1514 of cap 1500 can include sections 1530C, 1530D, 1530E, and 1530F essentially between threads 1540, each section having a slope with respect to the longitudinal axis A. In a further exemplary implementation, inner sidewall surface 1530 in sections 1530E and 1530F expands away from longitudinal axis A forming a flared out opening 1526. In yet further exemplary implementation inner cross sectional area at top of section 1530C can be smaller than cross sectional area at bottom of section 1530F, which forms opening 1526. In a still further exemplary implementation, cross sectional area at top of section 1530D can be configured to impede further insertion of needleless connector 9 into cavity 1528 such that tip 12 of needleless connector 9 stops essentially at top of section 1530D as illustrated in the example of FIG. 16.

In yet further exemplary implementation, inner sidewall surface 1530 in upper region 1512 of cap 1500 can include sections 1530AA and 1530A, essentially between protrusions 1555, each section having a slope with respect to the longitudinal axis A. In still further exemplary implementation, inner sidewall surface 1530 can include a transition section 1530B have a linear (see example of FIG. 19) or a curved (see example of FIGS. 17A, 17B, 17C and 18) surface where inner sidewall surface 1530 transitions from lower region 1514 to upper region 1512 such that cross sectional area at bottom of section 1530B in region 1514 is greater than cross sectional area at top of section 1530B in region 1512. Protrusions 1555 and/or smaller cross sectional area at top of section 1530B can prevent sponge 1580 from being displaced into upper region 1512 when cap 1500 engages needleless connector 9, such that sponge 1580 can be compressed and/or retained in within a certain region of cavity 1528, for example essentially within sections 1530B and 1530C, when tip 12 of connector 9 is secured within cavity 1528 of cap 1500.

Figure 18:
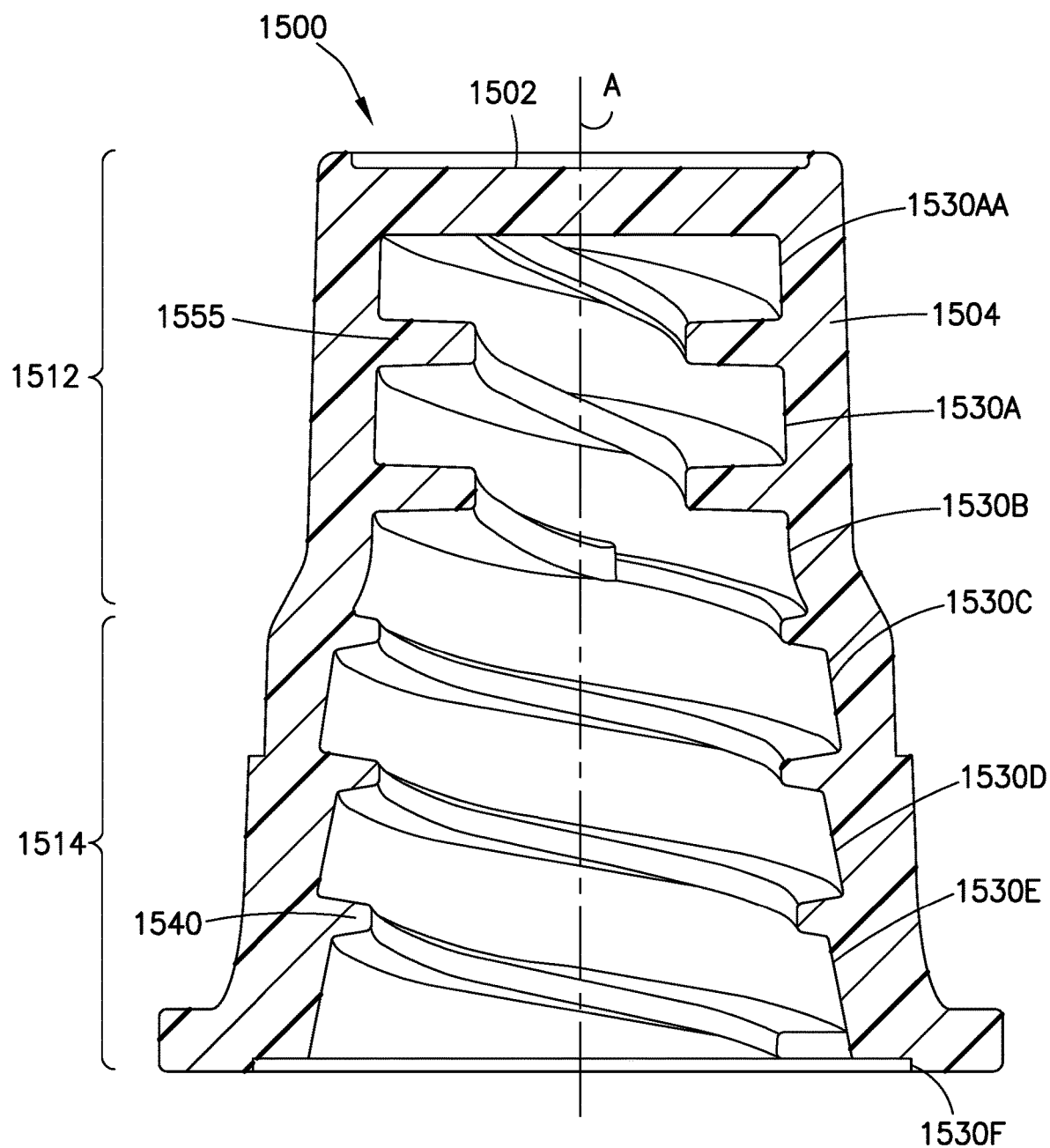
FIG. 18 is a cross-sectional view of a cap according to yet another further exemplary embodiment of the present invention.

In yet further exemplary implementation of an embodiment of the invention as illustrated in FIG. 18, inner sidewall surface 1530 in lower region 1514 of cap 1500 can include sections 1530C, 1530D, and 1530E essentially between threads 1540, and section 1530F as the bottom most section, or an aperture step, below section 1530F. All sections have essentially the same slope or angle with respect to the longitudinal axis A. However, unlike an exemplary implementation illustrated in FIG. 19, sections 1530C, 1530D, 1530E, and/or 1530F are not collinear.

Figure 19:
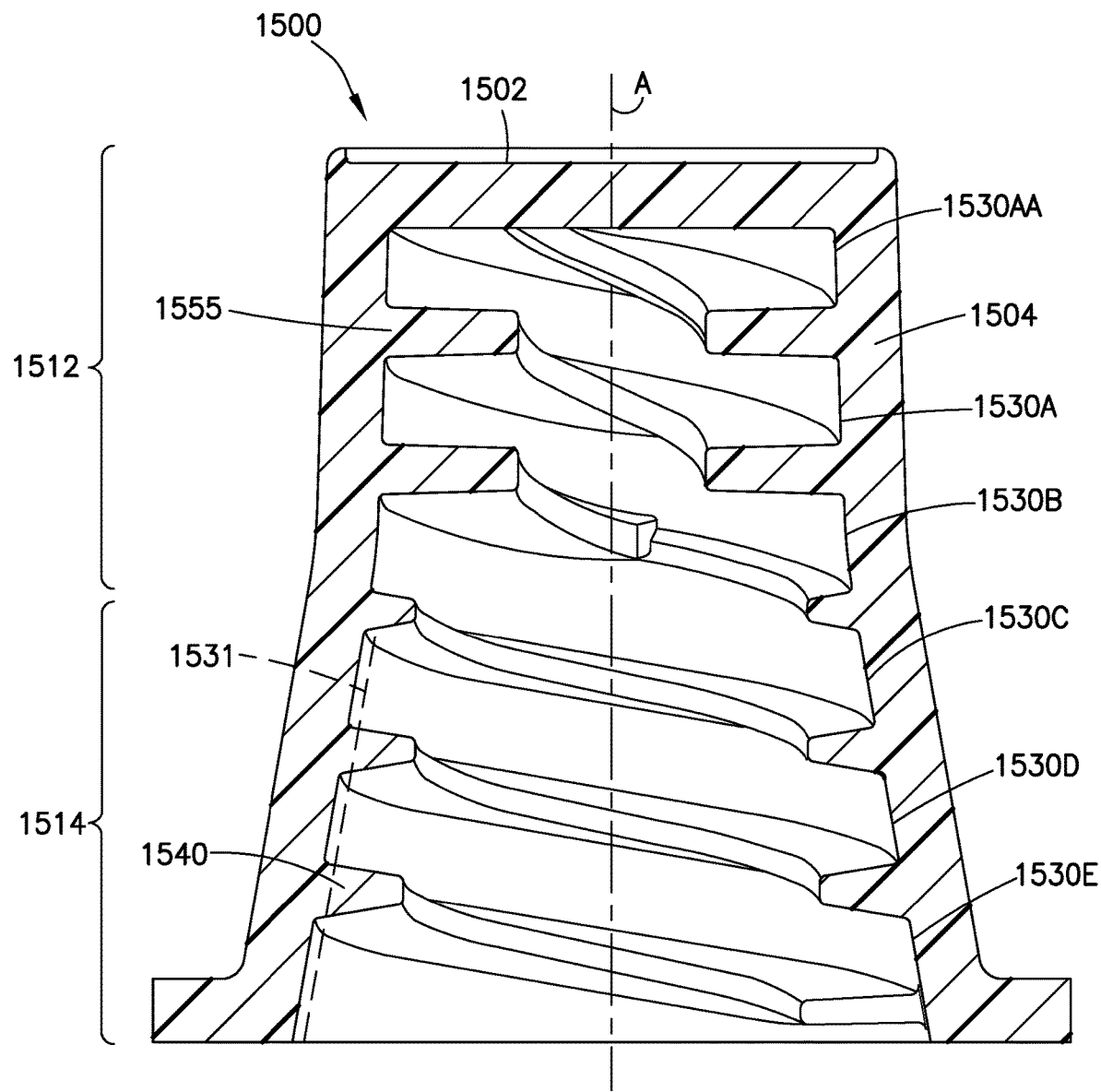
FIG. 19 is a cross-sectional view of a cap according to an exemplary implementation of yet further exemplary embodiment of the present invention.

In yet further exemplary implementation of an embodiment of the invention as illustrated in FIG. 19, inner sidewall surface 1530 in lower region 1514 of cap 1500 can include essentially collinear 1531 sections 1530C, 1530D and 1530E essentially between threads 1540 all sections having essentially the same slope or angle with respect to the longitudinal axis A. However, unlike an exemplary implementation illustrated in FIG. 18, section 1530F can be configured as an integral bottom most portion of section 1530E.

In yet another exemplary implementation, cap 1500 comprises ridges 1598 formed on outer sidewall surface 1520 of housing 1502, for example to facilitated better gripping of cap 1500 such as when handling cap 1500 to remove cover 1599, engage needleless connector 9, and/or disengage needleless connector 9.

Figure 20A:
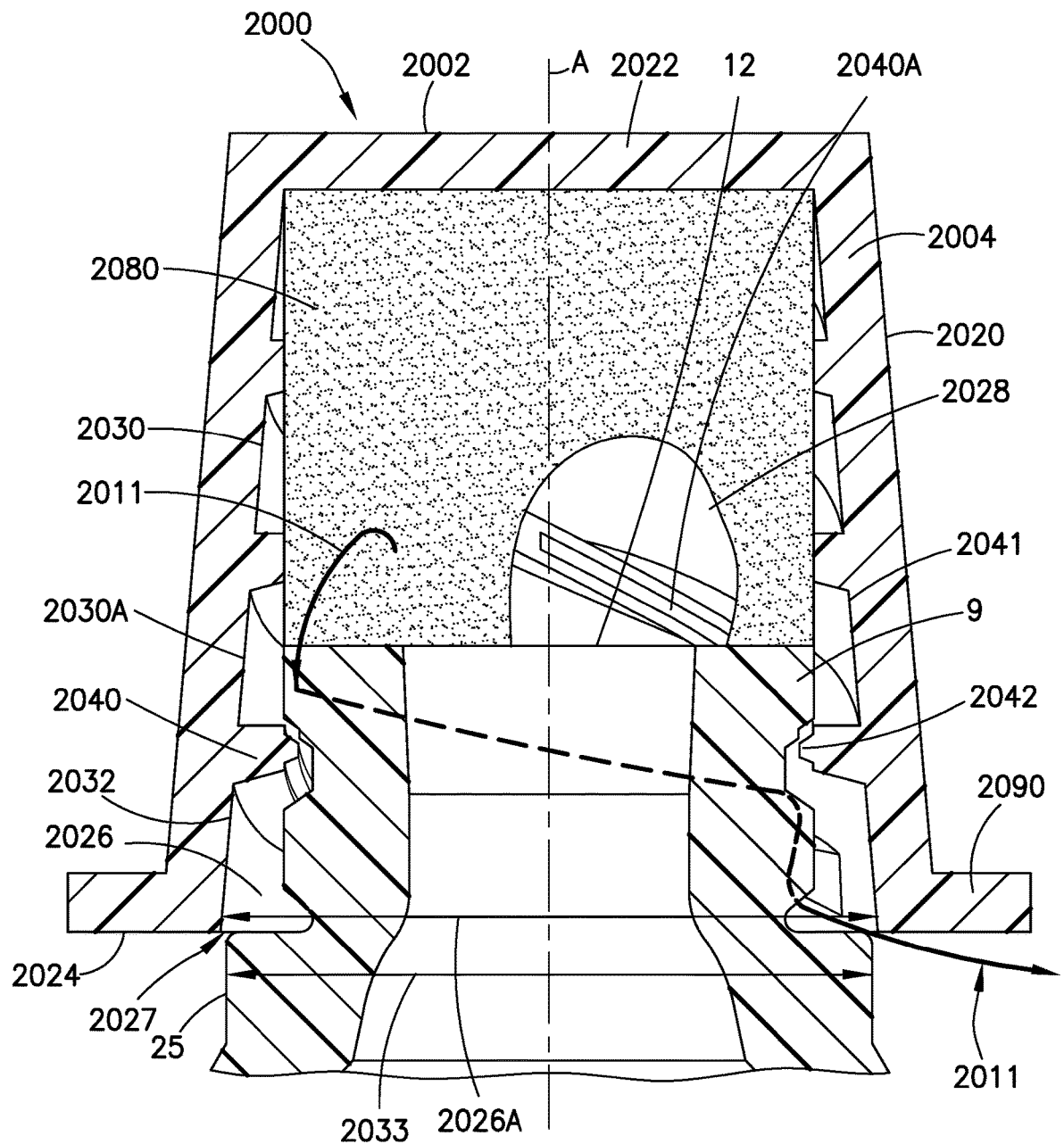
FIG. 20A is an illustration showing a cross-sectional view of a cap according to still another exemplary embodiment of the present invention disposed on a medical implement such as a needleless connector.
Figure 20C:
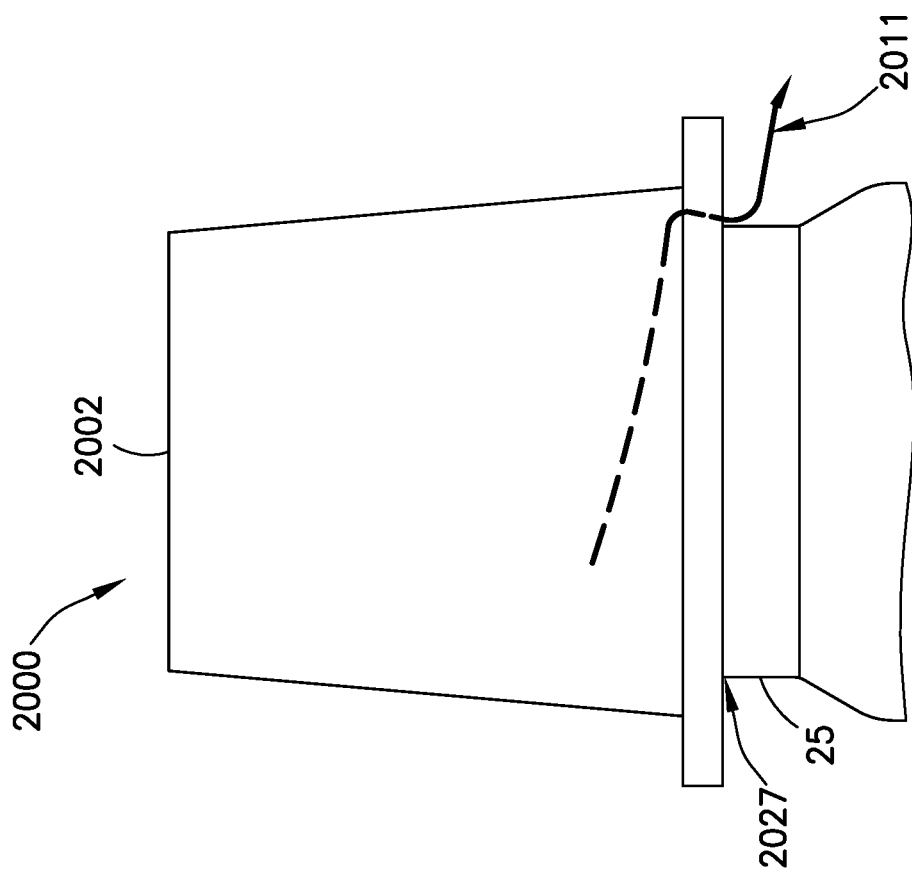
FIG. 20C is an illustration of venting in a cap according to still another exemplary embodiment of the present invention disposed on a medical implement such as a needleless connector.
Figure 20B:
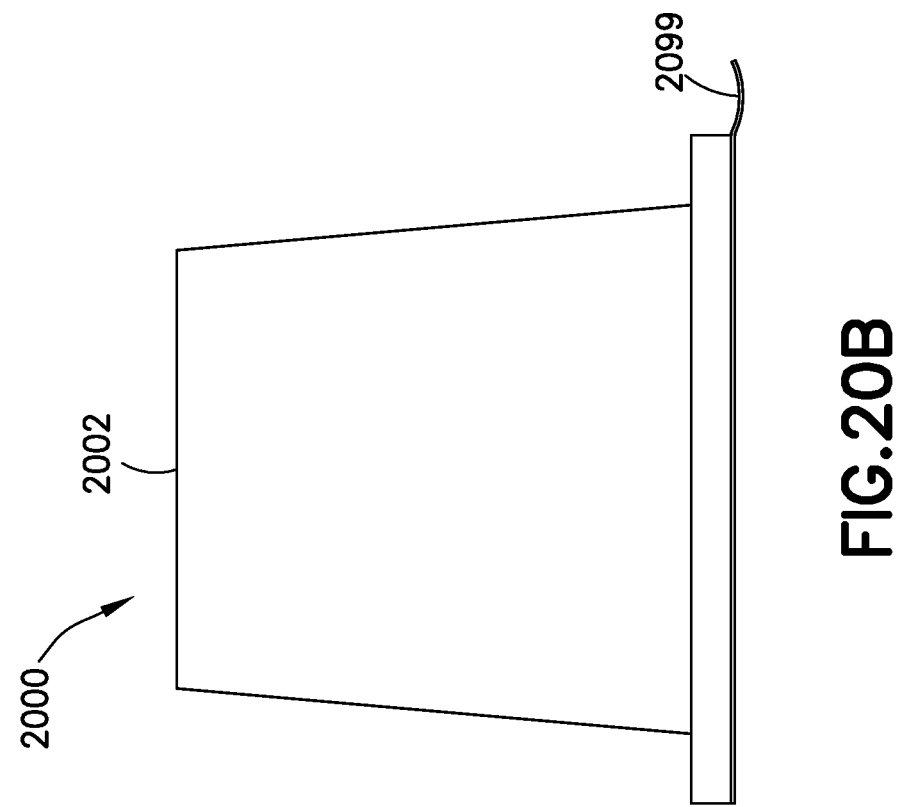
FIG. 20B illustrates another view of a cap according to a still another exemplary embodiment of the present invention.

According to yet further exemplary implementation of the embodiments of the present invention as illustrated in FIGS. 20A, 20B, and 20C, a disinfection cap 2000 can fit onto a tip 12 of needleless connector 9 and comprises housing 2002 comprising: a closed top 2022; sidewall 2004 with an outer sidewall surface 2020; and an open bottom 2024 with an opening 2026 to an inner cavity 2028 within housing 2002 for receiving tip of a needleless connector 9. The inner cavity 2028 accommodates an alcohol soaked disinfection sponge 2080. The bottom 2024 formed by sidewall 2004 of housing 2002 includes a bottom portion 2090 having an inner sidewall surface 2032 such that the opening 2026 does not form an airtight seal with outer surface 25 of needleless connector 9 when tip of connector 9 is securely engaged within cavity 2028. As in the example of FIG. 15, a removable cover such as 1599 can be attached to bottom 2024 of cap 2000 to seal inner cavity 2028 including disinfection sponge 2080.

In an exemplary implementation, opening 2026 to inner cavity 2028 formed by inner sidewall surface 2032 is essentially circular and has an opening diameter 2026A, which is larger than a flange diameter 2033 of outer surface 25 of needleless connector 9, such that opening diameter 2026A causes a venting gap 2027 between inner sidewall surface 2032 and outer surface 25 of needleless connector 9.

Inner cavity 2028 comprises threads 2040 on inner sidewall surface 2030 of sidewall 2004 for engaging thread 13 of needleless connector 9. In an exemplary implementation, at least a portion of threads 2040 can include a protrusion 2040A to facilitate a more secure engagement with thread 13 of needleless connector 9.

The pitch of threads 2040 corresponds to the pitch of thread 13 of needleless connector 9. However, the profile (major profile 2041 and/or minor profile 2042) of threads 2040 of the cap 2000 does not correspond to the thread 13 of the needleless connector 9. Since engaging threads 2040 of cap 2000 do not correspond to the thread 13 of the needleless connector 9, venting 2011 of the alcohol soaked disinfection sponge 2080 occurs essentially around the outside of threads 13 of the needleless connector 9 and through opening 2026 to the inner cavity 2028 to the outside (atmosphere) of the cap housing 2002. In an exemplary implementation, venting 2011 occurs through opening 2026 via venting gap 2027. A removable cover 2099 can be attached to bottom 2024 of cap 2000 to seal inner cavity 2028 including disinfection sponge 2080.

According to an exemplary implementation of an embodiment of the invention as illustrated in FIG. 20A, inner sidewall surface 2030 of cap 2000 can include sections such as 2030A essentially between threads 2040, each section having an essentially the same slope with respect to the longitudinal axis A.

Figure 21A:
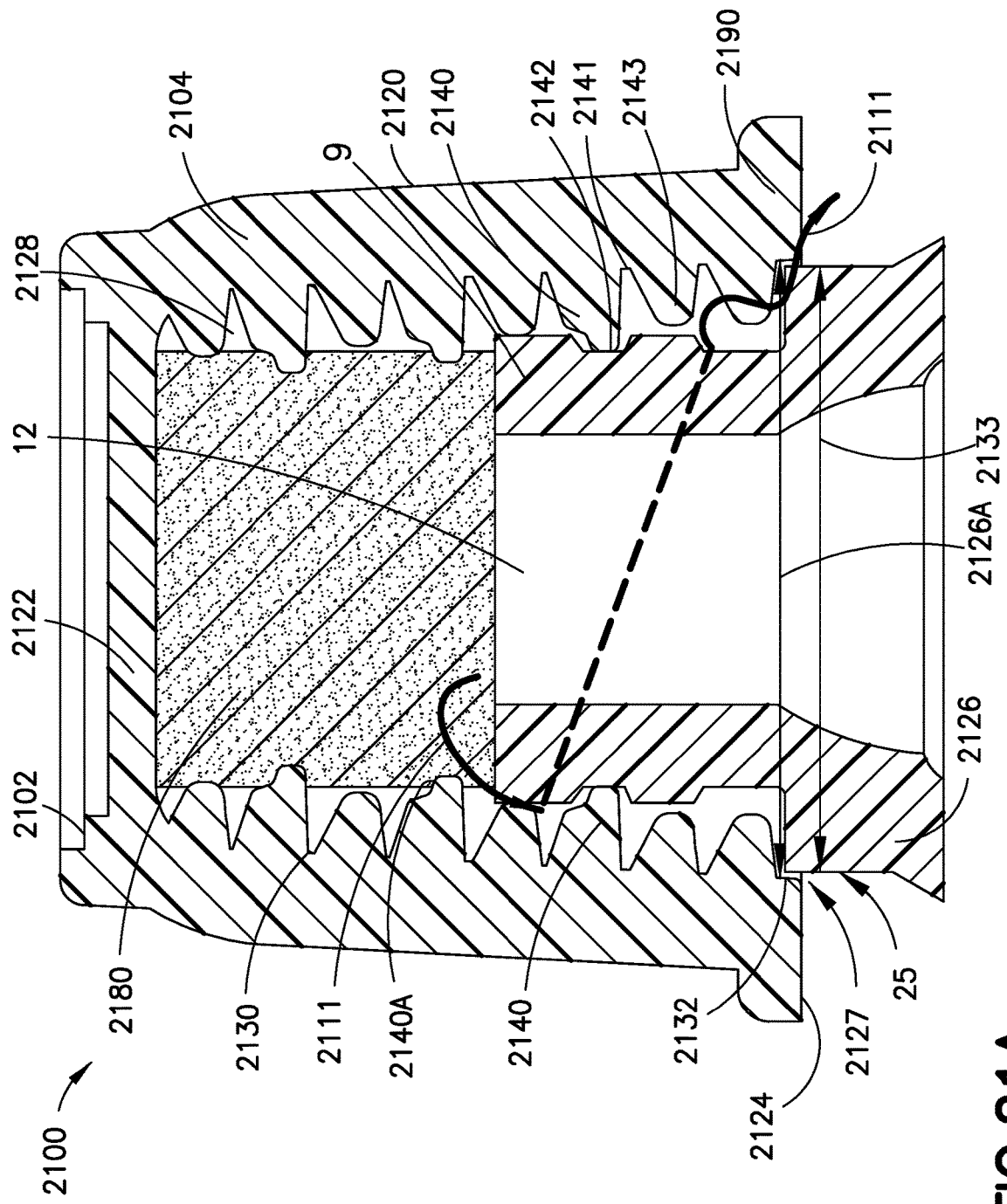
FIG. 21A is an illustration showing a cross-sectional view of a cap according to yet still another exemplary embodiment of the present invention disposed on a medical implement such as a needleless connector.
Figure 21B:
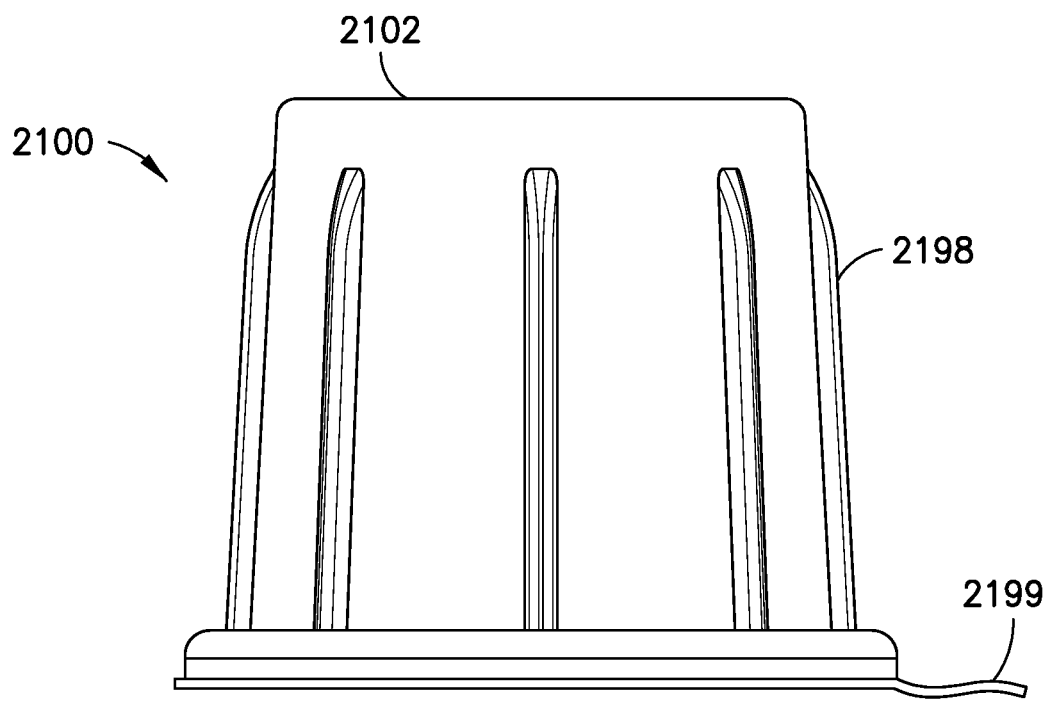
FIG. 21B illustrates another view of a cap according to yet still another exemplary embodiment of the present invention.
Figure 21C:
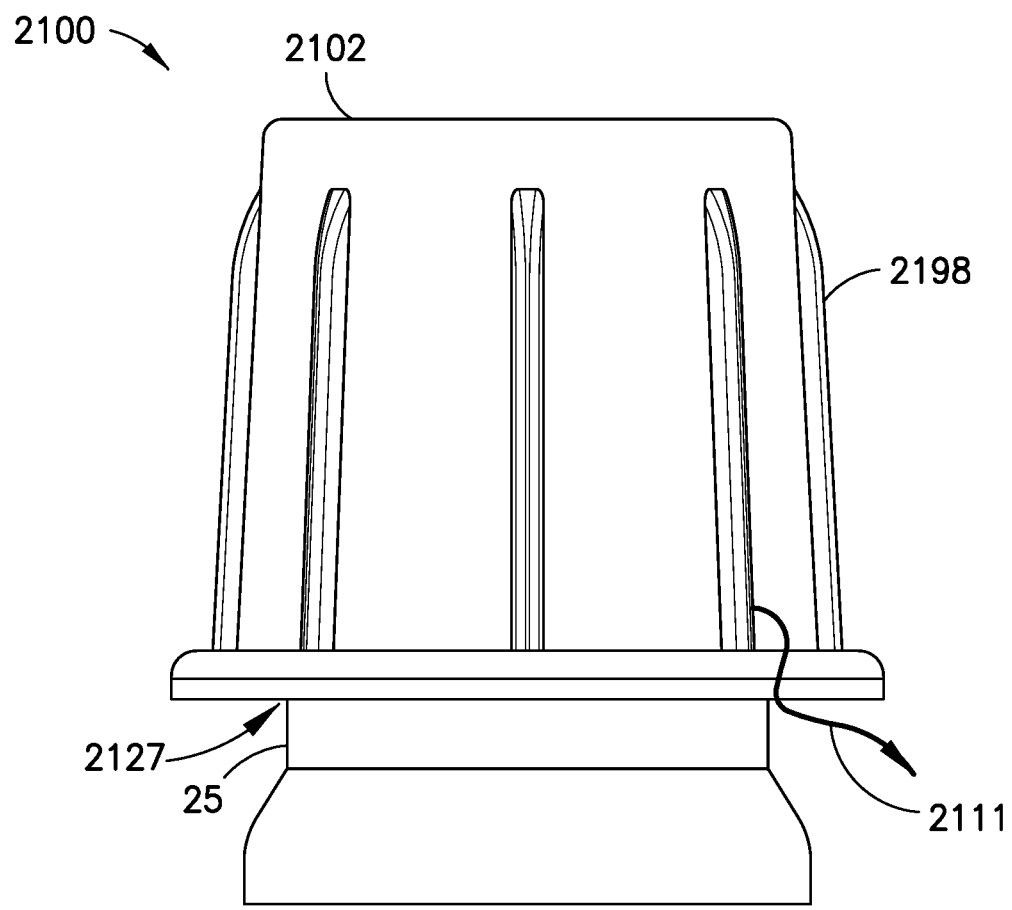
FIG. 21C is an illustration of venting in a cap according to yet still another exemplary embodiment of the present invention disposed on a medical implement such as a needleless connector.

According to yet further exemplary implementation of the embodiments of the present invention as illustrated in FIGS. 21A, 21B, and 21C, a disinfection cap 2100 can fit onto a tip 12 of needleless connector 9 and comprises housing 2102 comprising: a closed top 2122; sidewall 2104 with an outer sidewall surface 2120; and an open bottom 2124 with an opening 2126 to an inner cavity 2128 within housing 2102 for receiving tip of a needleless connector 9. The inner cavity 2128 accommodates an alcohol soaked disinfection sponge 2180. The bottom 2124 formed by sidewall 2104 of housing 2102 includes a bottom portion 2190 having an inner sidewall surface 2132 such that the opening 2126 does not form an airtight seal with outer surface 25 of needleless connector 9 when tip of connector 9 is securely engaged within cavity 2128. As in the example of FIG. 15, a removable cover such as 1599 can be attached to bottom 2124 of cap 2100 to seal inner cavity 2128 including disinfection sponge 2180.

In an exemplary implementation, opening 2126 to inner cavity 2128 formed by inner sidewall surface 2132 is essentially circular and has an opening diameter 2126A, which is larger than a flange diameter 2133 of outer surface 25 of needleless connector 9, such that opening diameter 2126A causes a venting gap 2127 between inner sidewall surface 2132 and outer surface 25 of needleless connector 9.

Inner cavity 2128 comprises threads 2140 on inner sidewall surface 2130 of sidewall 2104 for engaging thread 13 of needleless connector 9. In an exemplary implementation, at least a portion of threads 2140 can include a protrusion 2140A to facilitate a more secure engagement with thread 13 of needleless connector 9.

The pitch of threads 2140 corresponds to the pitch of thread 13 of needleless connector 9. However, the profile (major profile 2141 and/or minor profile 2142) of threads 2140 of the cap 2100 does not correspond to the thread 13 of the needleless connector 9. Since engaging threads 2140 of cap 2100 do not correspond to the thread 13 of the needleless connector 9, venting 2111 of the alcohol soaked disinfection sponge 2180 occurs essentially around the outside of threads 13 of the needleless connector 9 and through opening 2126 to the inner cavity 2128 to the outside (atmosphere) of the cap housing 2102. In an exemplary implementation, venting 2111 occurs through opening 2126 via venting gap 2027.

In an exemplary implementation, inner cavity 2128 comprises threads 2143 on inner sidewall surface 2130 of sidewall 2104 which have a smaller profile than threads 2140 and do not engage, for example in a friction fit manner, with thread 13 of needleless connector 9. A removable cover 2199 can be attached to bottom 2124 of cap 2100 to seal inner cavity 2128 including disinfection sponge 2180.

In yet another exemplary implementation as illustrated in FIG. 21C and similar to an exemplary embodiment of FIG. 17C, cap 2100 comprises ridges 2198 formed on outer sidewall surface 2120 of housing 2102, for example to facilitated better gripping of cap 2100 such as when handling cap 2100 to remove cover 1599, engage needleless connector 9, and/or disengage needleless connector 9.

Figure 23A:
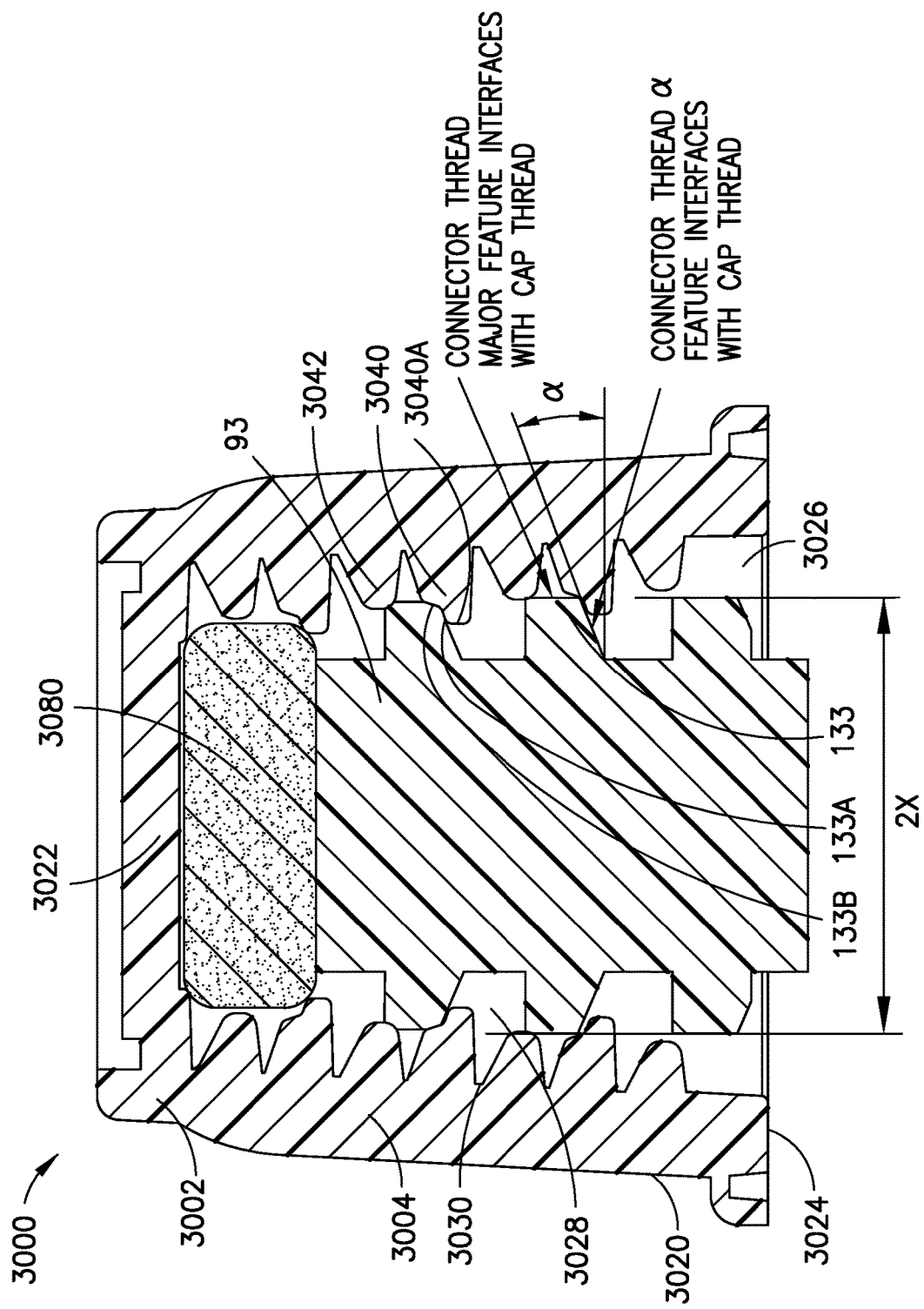
FIG. 23A is a cross-section view of a cap according to another exemplary embodiment of the present invention.
Figure 23B:
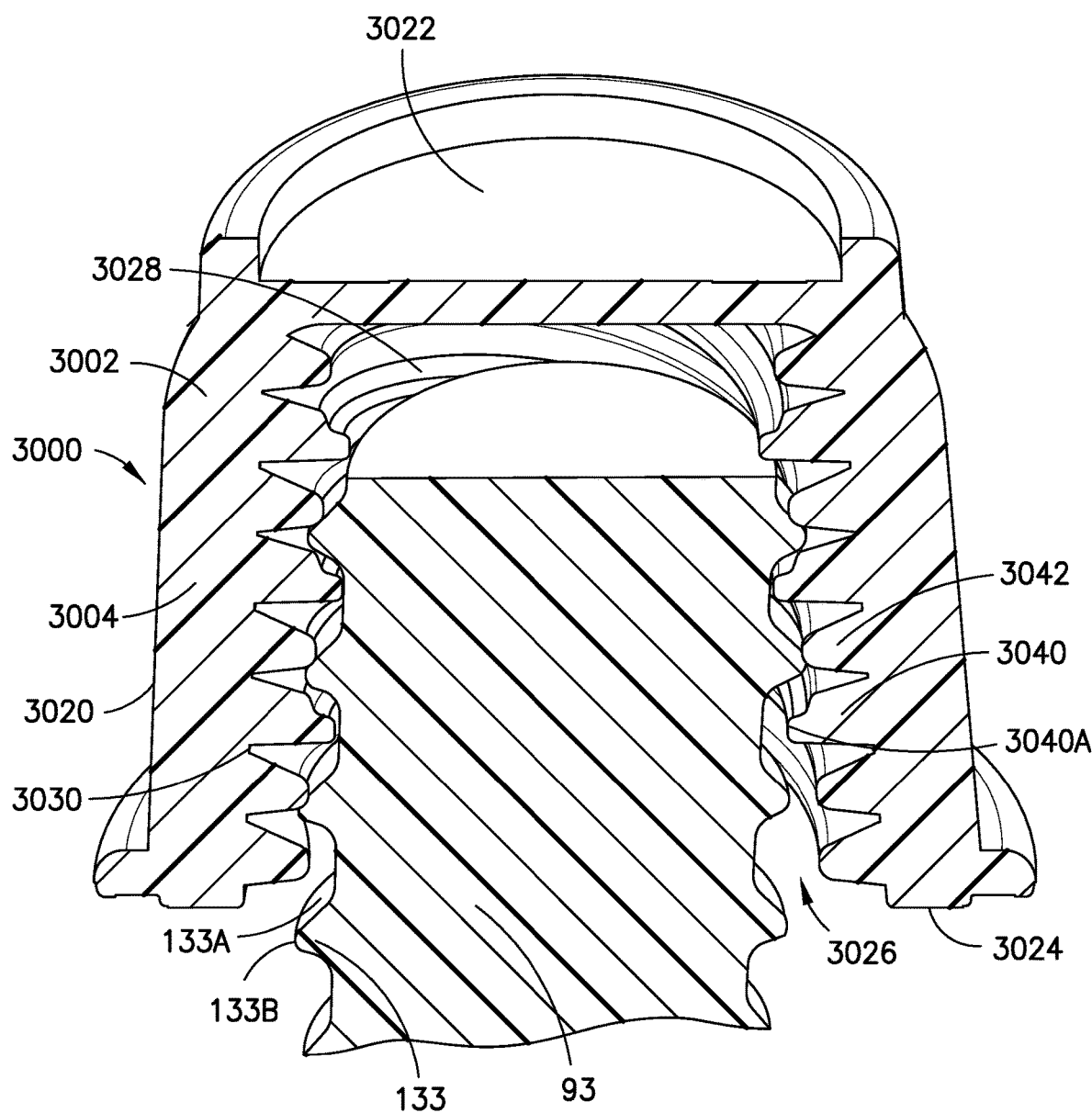
FIG. 23B is a three-dimensional drawing of a cap according to another exemplary embodiment of the present invention.

FIGS. 23A and 23B illustrate a disinfection cap 3000 according an exemplary implementation of the embodiments of the present invention receiving a tip of needleless connector 93, which is a female 6% (Luer) lock conical fitting with external thread 113 configured according to International Standard, ISO594-2:1998(E), as shown in annotated FIG. 22 where: α is angle of thread or lug bearing surface against separation with the plane perpendicular to the axis of lock fitting, which can be called in a non-limiting exemplary manner a connector thread α feature 133A; γ is minimum angle of external thread or lug non-bearing surface against separation with the plane perpendicular to the axis of the lock fitting; 2X is outside diameter across the lugs or external thread, which can be called in a non-limiting exemplary manner connector thread major feature 133B; E is minimum length of male lock fitting; G is maximum outside diameter of female lock fitting at base of lugs or maximum inside diameter of external thread; S is lug crest width or thread crest width of female lock fitting with lugs or external thread; Y is maximum width of base of lug (axial) or thread at base, of female lock fitting to be measured at a point corresponding to an outside diameter equal to G.

Referring to cross-sectional view of FIG. 23A and three-dimensional view of FIG. 23B, disinfection cap 3000 comprises housing 3002 comprising: a closed top 3022; sidewall 3004 with an outer sidewall surface 3020; and an open bottom 3024 with an opening 3026 to an inner cavity 3028 within housing 3002 for receiving needleless connector 93. The inner cavity 3028 can, but does not have to, accommodate an alcohol soaked disinfecting sponge 3080. As in the example of FIG. 15, a removable cover such as 1599 can be attached to bottom 3024 of cap 3000 to seal inner cavity 3028 with, or without (as shown in FIG. 23B), a disinfection sponge 3080 disposed therein.

Inner cavity 3028 of cap 3000 comprises one or more threads (protrusions, lugs, or ribs) 3040, 3042 on inner sidewall surface 3030 of its sidewall 3004. In an exemplary implementation, at least a portion of at least one thread, or entire thread, such as thread 3040 can include a further protrusion (bump, lug, or rib) 3040A extending into cavity 3028 from thread 3040. Protrusion 3040A engageably interfaces with at least a portion of thread 133 of connector 93, for example a portion of connector thread α feature 133A and/or a portion of connector thread major feature 133B, to facilitate engagement of connector 93 within cavity 3028 of cap 3000.

In an exemplary implementation, threads 3042 on inner sidewall surface 3030 of sidewall 3004 have a smaller profile than threads 3040 and do not engage, for example in a friction fit manner, with thread 133 of connector 93. Threads 3040 and 3042 can be formed as a single continuous or partial thread with selectively formed features of thread 3040 and/or 3042 thereon, or as alternating continuous or partial threads for example at 180-degrees, or at 90 degrees (as illustrated for example in FIGS. 24A-24I).

In another or additional exemplary implementation, thread or threads, such as threads 3042, which do not have further protrusions, can facilitate axial alignment of cap 3000 with connector 93 when placing cap 3000 onto connector 93, or inserting connector 93 into cavity 3028 of cap 3000, as illustrated for example in FIGS. 23A and 23B. In an exemplary implementation, major profile of thread 3040 within cavity 3028 can correspond to, or match, essentially exactly or within a given tolerance thread major feature 133B of connector 93. In other words, threads 3042 interface with threads 133 essentially tangentially at the surface contact portions thereof. For example, in a cylindrical embodiment of cap 3000, threads 3042 would meet threads 133 essentially at a contact diameter.

In an exemplary implementation where cap 3000 and cavity 3028 are essentially frustoconical with a larger cross section being at top 3022, as shown in the example of FIG. 23A, engaging threads 3040 can provide a more secure engagement of connector 93 as it advances into cavity 3028. Non-engaging threads 3042 can provide interference fit, for example to facilitate further alignment or retention of connector 93 within cavity 3028.

In yet another or additional exemplary implementation, pitch and/or profile of threads 3040 and/or 3042 of the cap 3000 do not correspond to pitch and/or profile of thread 133 of connector 93. Accordingly, venting in cavity 3028 of cap 3000 occurs essentially around the outside of threads 133 when connector 93 is inside cavity 3028.

In still another or additional exemplary implementation, pitch of threads 3040 corresponds to the pitch of thread 133 of connector 93. However, the profile of threads 3040 does not correspond to thread 133. Since engaging threads 3040 do not correspond to thread 133 venting in inner cavity 3028 occurs essentially around the outside of threads 133 when connector 93 is inside the inner cavity 3028.

Figure 24A:
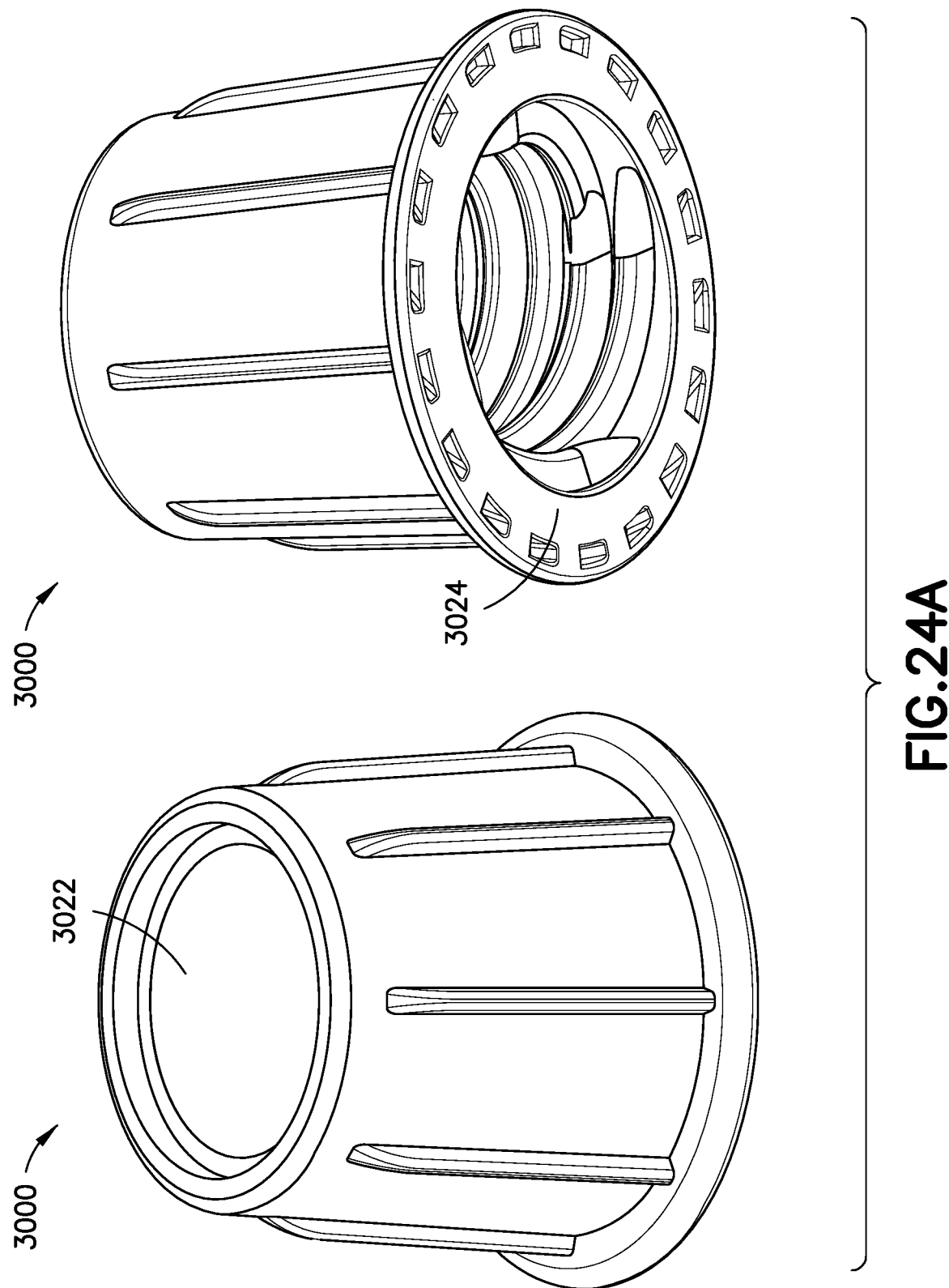
FIGS. 24A, 24B, 24C, 24D, 24E, 24F, 24G, 24H, and 24I are engineering drawings at different perspective views, cross sections and magnification illustrative of a cap according to exemplary implementations of exemplary embodiments of the present invention.

In yet another exemplary implementation as illustrated in FIG. 24A and similar to an exemplary embodiment of FIGS. 17C and 21B, cap 3000 comprises ridges 3098 formed on outer sidewall surface 3020 of housing 3002, for example to facilitated better gripping of cap 3000 such as when handling cap 3000, engaging connector 93 (into cavity 3028), and/or disengaging connector 93 (out of cavity 3028).

Referring to FIGS. 24A-24I, an exemplary implementation of embodiments of the present invention is described in terms of certain dimensional characteristics of various component of a disinfection cap 3000. Both relative and specific numerical characteristics presented in FIGS. 24A-24I are intended to facilitate a more complete understanding of exemplary implementations of embodiments of the present invention without limiting the scope of the invention as set forth in the claims. As in the example of FIG. 15, a removable cover such as 1599 can be attached to bottom 3024 of cap 3000 to seal inner cavity 3028 with, or without (as shown in FIGS. 24A-24I), a disinfection sponge 3080 disposed therein.

Figure 24B:
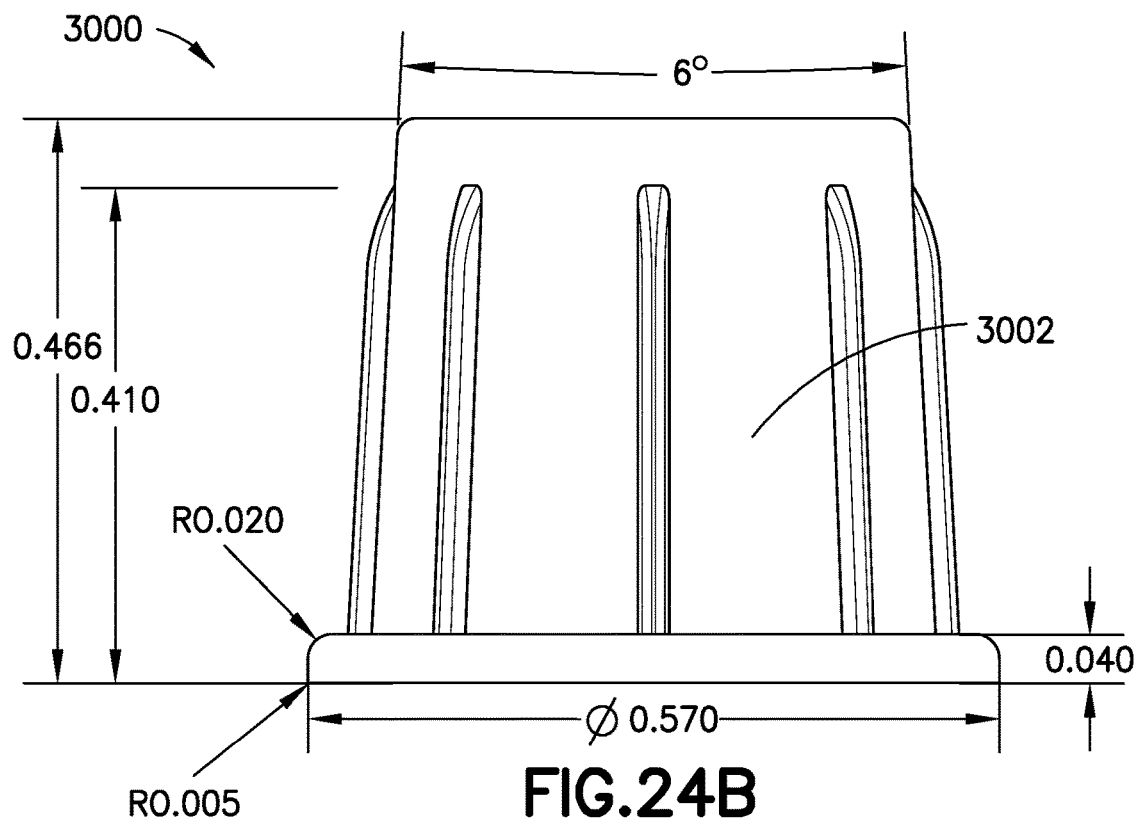
Figure 24C:
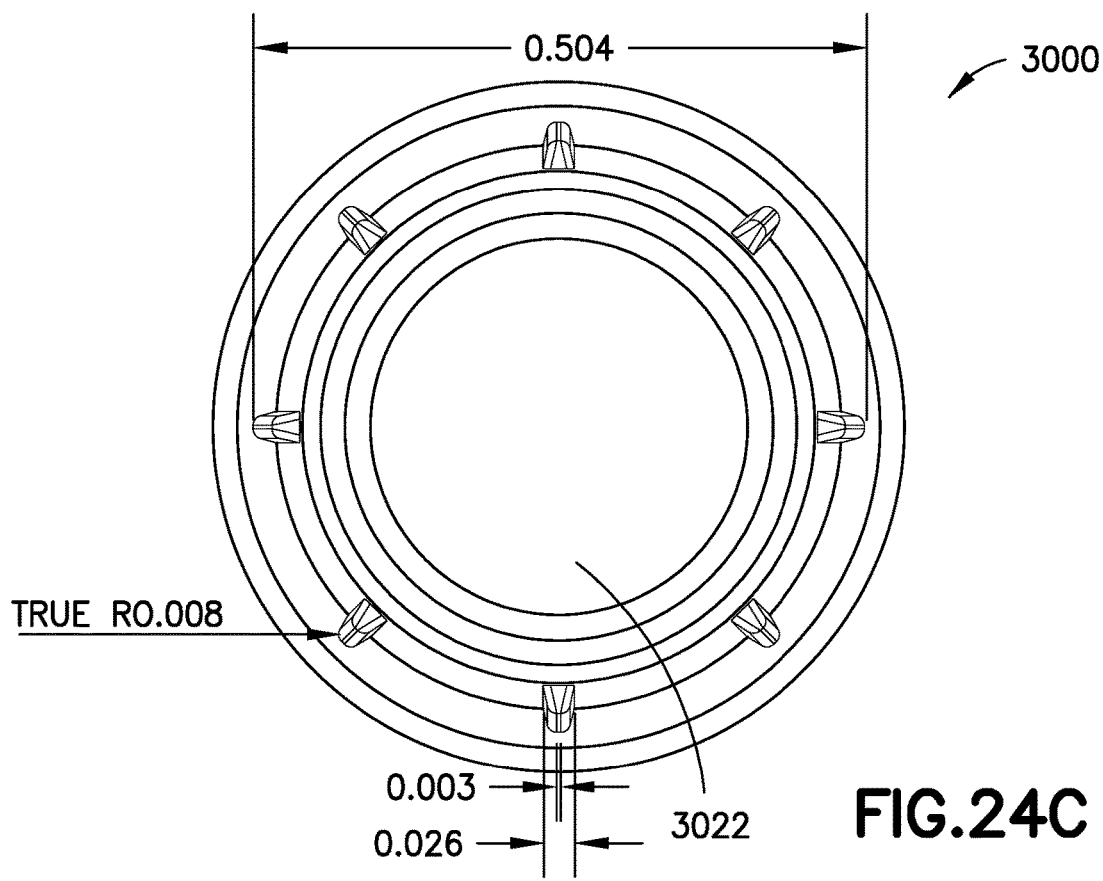
Figure 24D:
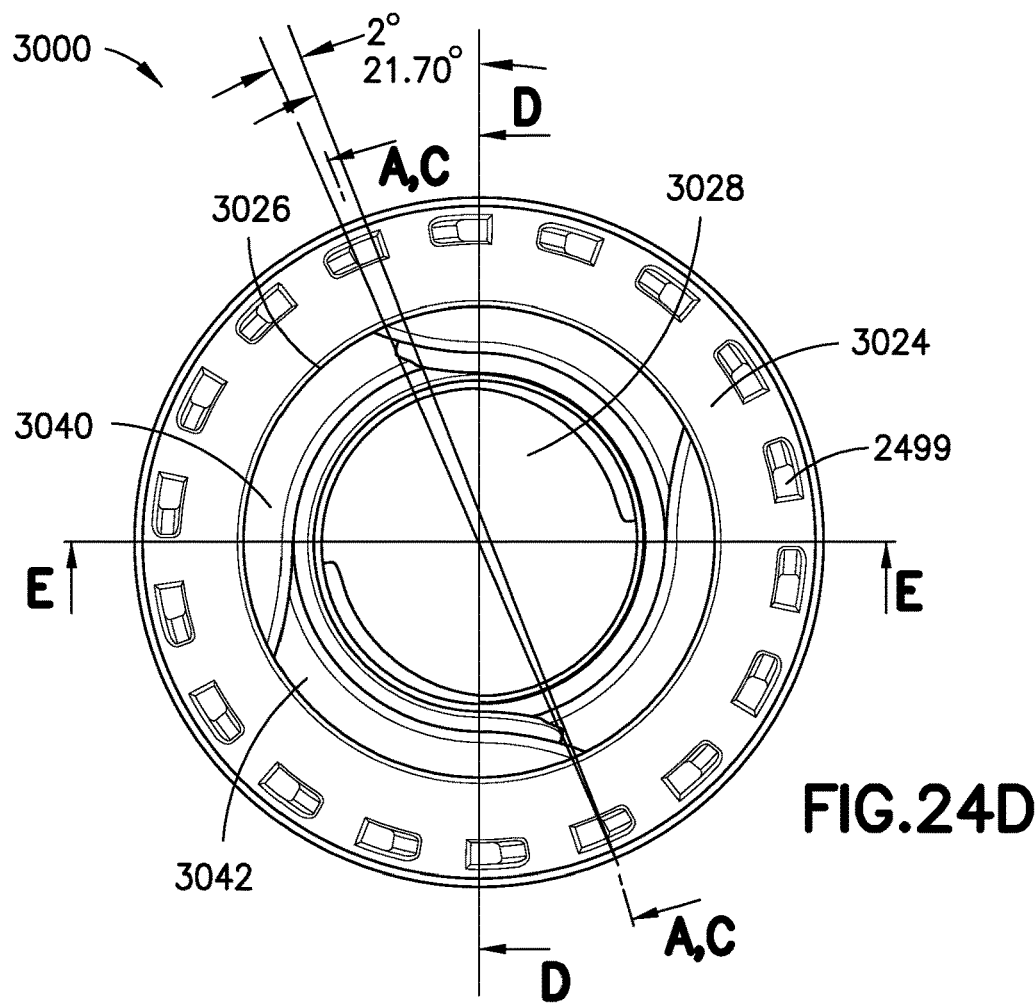

FIG. 24A shows three dimensional views of cap 3000 from different perspectives: from an angle showing the top 3022 of cap 3000 (in the drawing on the left), and from an angle showing the bottom 3024 of cap 3000 (in the drawing on the right). FIG. 24B shows a side view of cap 3000 illustrating a 6-degree frustoconical configuration of body 3002 of cap 3000 according to an exemplary implementation of embodiments of the present invention. FIG. 24C is a view of cap 3000 from top 3022. FIG. 24D is a view of cap 3000 from bottom 3024, which also shows opening 3026 to inner cavity 3028, threads 3040/3042, and includes indications AC-AC, D-D, and E-E of cross sectional views of cap 3000 illustrated in FIGS. 24E, 24F, and 24H respectively. In an exemplary implementation, cap 3000 can include divots 2499 formed at bottom 3024, which are anti-rotational lugs used for injection molding when manufacturing cap 3000.

Figure 24E:
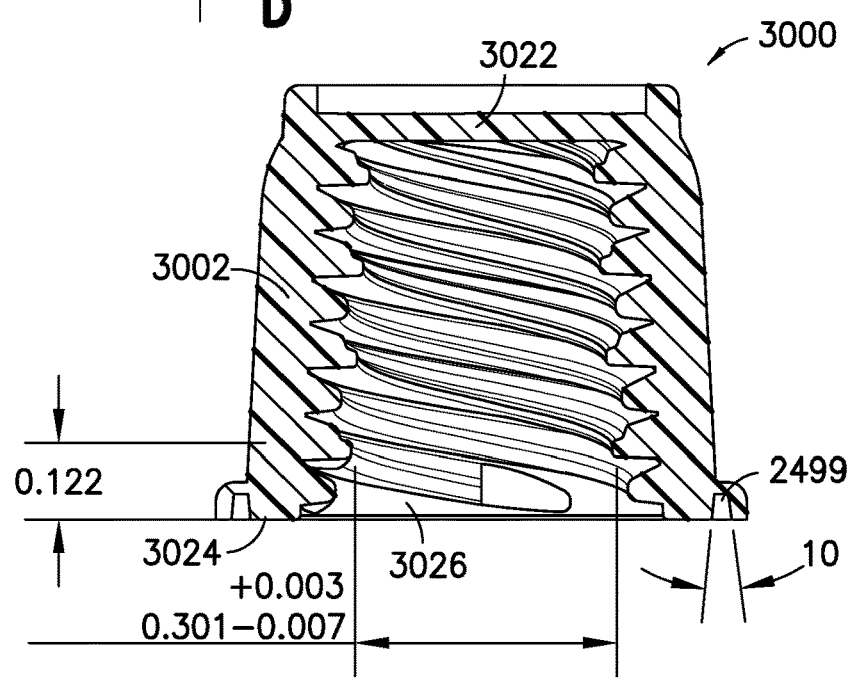
Figure 24F:
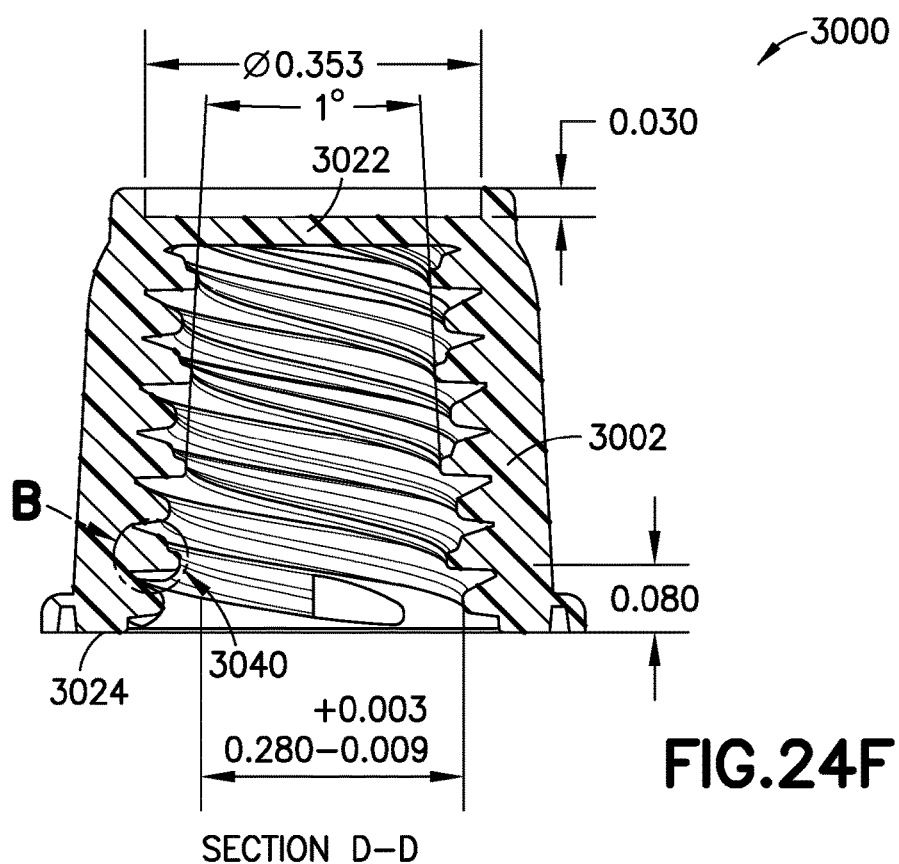

FIG. 24E is a cross sectional view AC-AC (see FIG. 24D) of cap 3000 showing relative dimensional characteristics of cap body 3002 including opening 3026 and a thread pitch, as well as divots 2499 (if formed at bottom 3024 of cap 3000). FIG. 24F is a cross sectional view D-D (see FIG. 24D) of cap 3000 also showing relative dimensional characteristics of cap body 3002 including opening 3026 and a thread pitch, as well as features of top 3022 and detail B of thread 3040. FIG. 24H is a cross sectional view E-E (see FIG. 24D) of cap 3000 further showing relative dimensional characteristics of cap body 3002 including opening 3026 and a thread pitch, as well as a frustoconical configuration of inner cavity 3028, a lip feature of bottom 3024, and detail A of thread 3042.

Figure 24G:
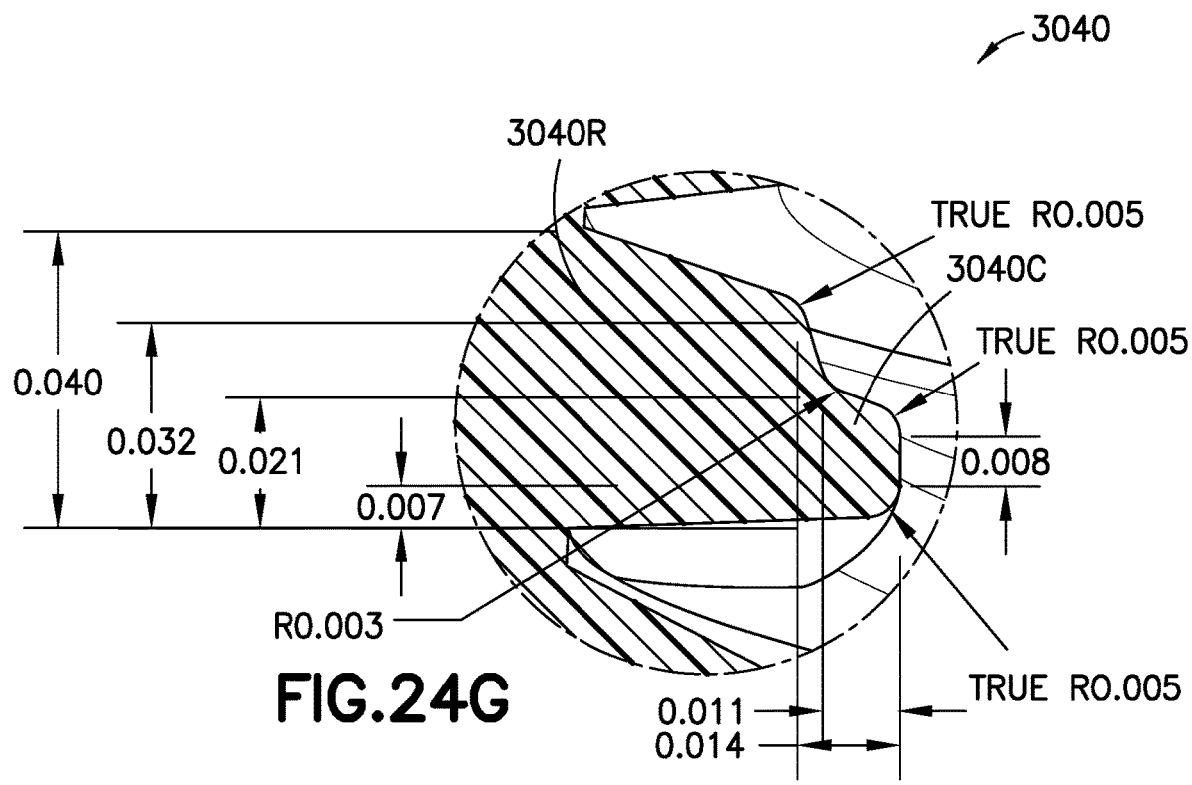
Figure 24H:
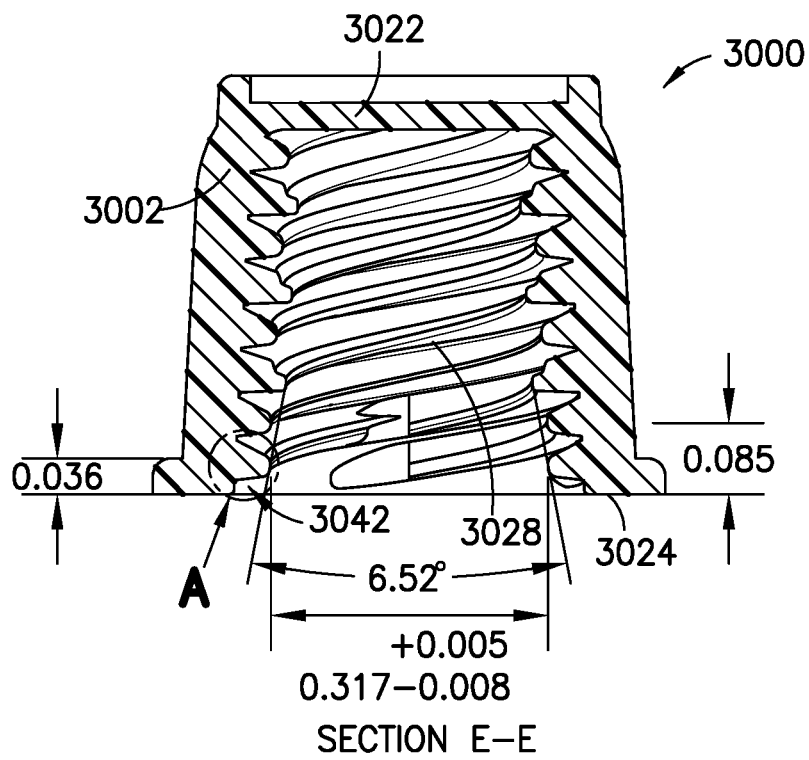
Figure 24I:
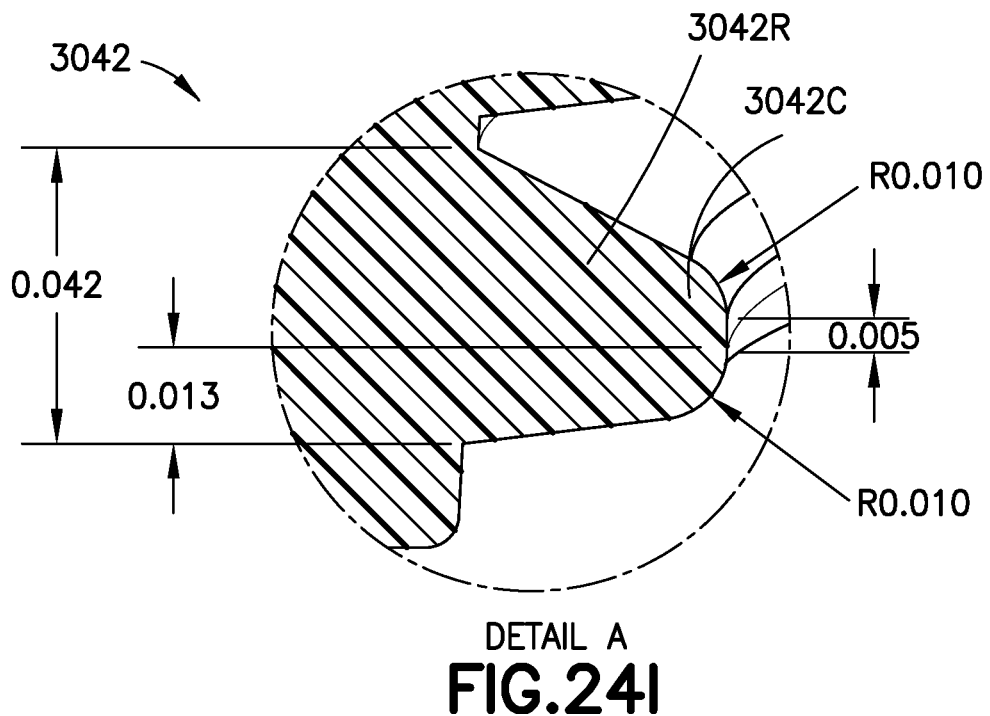

FIG. 24G is an enlarged cross sectional view B (see FIG. 24F) of specific relative dimensional characteristics of thread 3040 according to an exemplary implementation of the embodiments of the present invention. FIG. 24I is an enlarged cross sectional view A (see FIG. 24H) of specific relative dimensional characteristics of thread 3042 according to an exemplary implementation of the embodiments of the present invention. As shown in the examples of FIGS. 24G and 24I, thread 3040 and thread 3042 can have substantially similar respective root section profiles 3040R and 3042R, and substantially different crest section profiles 3040C and 3042C.

Figure 25B:
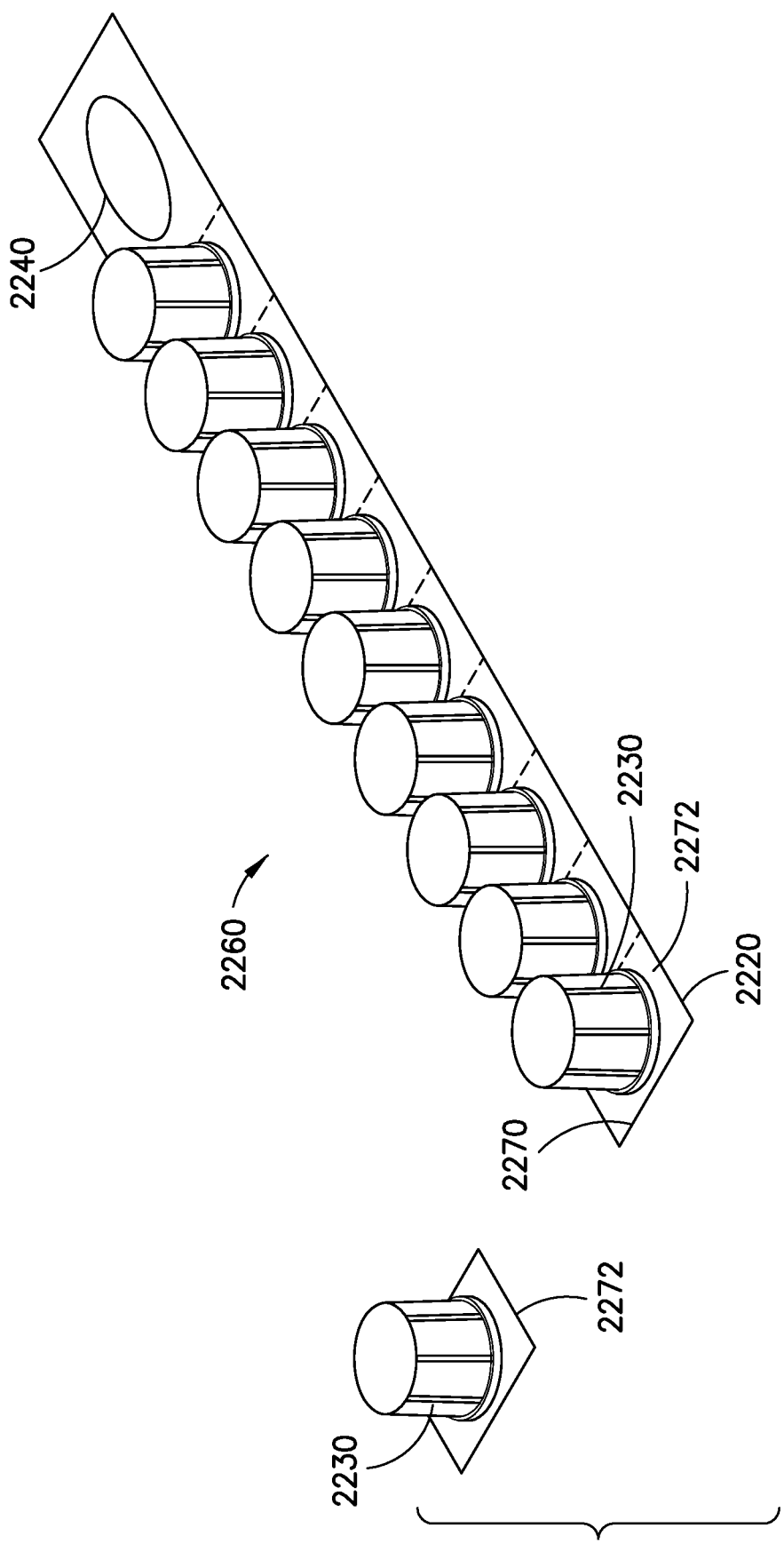

Referring to FIGS. 25A and 25B, a dispensing device 2260 according to an exemplary embodiment of the present invention, includes a plurality of caps 2230 disposed on a perforated strip 2220. In an exemplary implementation, perforations 2270 are formed between caps 2230 disposed on strip 2220 to define portions 2272 of strip 2220 having at least one cap 2230 disposed thereon. Caps 2230 can be configured structurally and functionally like any of the caps illustrated in the examples of FIGS. 1A, 1B, and 3A through 21C and described above with reference thereto. In an exemplary implementation, strip 2220 can be a peel strip configured as a cap cover attached to bottom of each cap 2230 to seal inner cavity of each cap 2230, for example as described above with reference to FIGS. 1A, 1B, 4B, 8B, 11B, 14B, 15, 20B, 21B, 25A.

As illustrated in the example of FIG. 25A, each cap 2230 can be peeled off or separated from strip 2220 for immediate use, for example, to cap a needleless connector. On the other hand, as illustrated in the example of FIG. 25B, portion 2272 including a cap 2230 disposed thereon can be selectively separated from strip such that inner cavity of cap 2230 remains sealed by the portion 2272 similar to individual caps illustrated in the examples of FIGS. 1A, 1B, 4B, 8B, 11B, 14B, 15, 20B, and 21B.

Figure 25D:
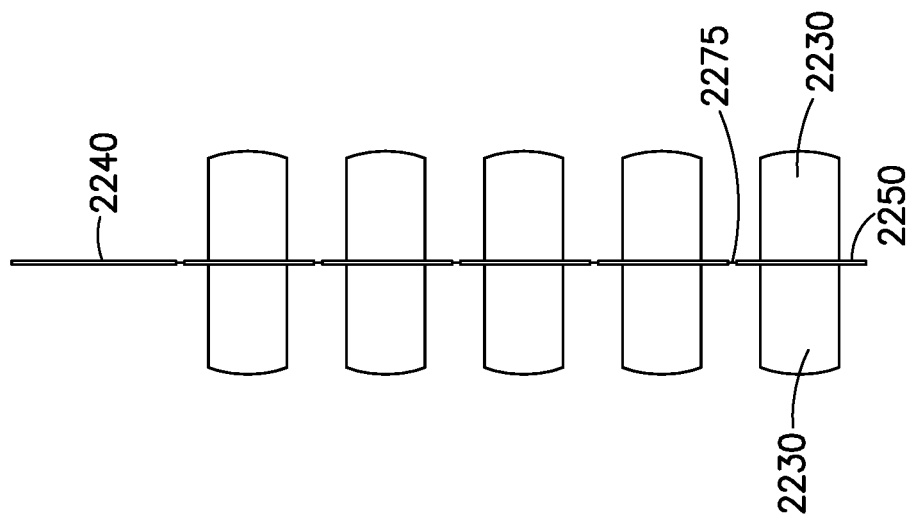
FIG. 25D illustrates a device according to yet another exemplary embodiment of the present invention for hanging a plurality of caps on an IV pole.
Figure 25C:
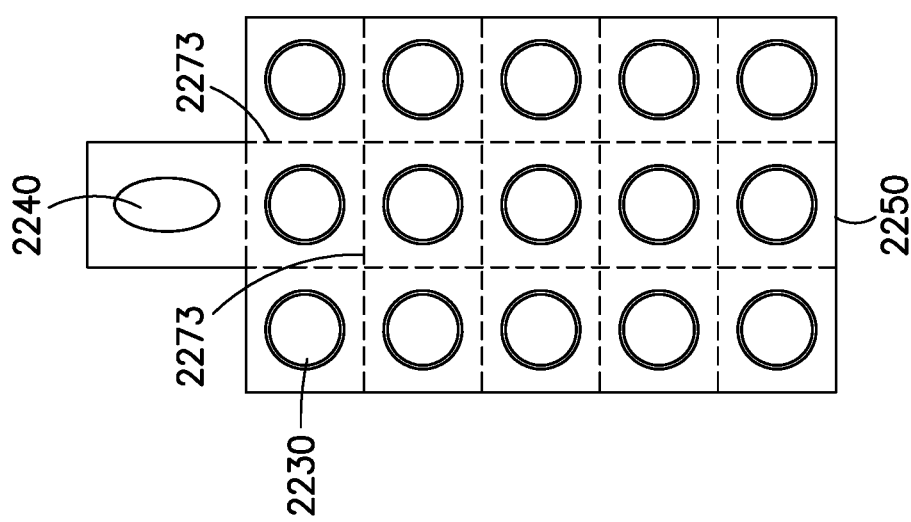
FIG. 25C illustrates a device according to another exemplary embodiment of the present invention for hanging a plurality of caps on an IV pole.

According to exemplary embodiments of the present invention, dispensing device 2260 can be configured to have a perforated strip 2220 having a single row of caps 2230, as shown in FIGS. 25A and 25B, or a perforated strip 2250 having multiple rows of caps 2230 separated by perforations 2273, as illustrated in the example of FIG. 25C showing a top view of such an implementation. According to yet another exemplary implementation as illustrated in a side view of FIG. 25D, dispensing device 2260 can be configured to have a double-sided perforated peel strip 2255 having two opposing sides 2265 and 2267, and caps 2230 attached at both sides thereof, such that two sealed caps 2230 can be selectively detached from strip 2255 at perforation 2275 for later use (see FIG. 25D) and/or individually removed from either side of strip 2255 for immediate use (see FIG. 25D).

As illustrated in FIGS. 25A, 25B, 25C, and 25D, strip 2220/2250/2255 is essentially flat and has perforations in-between each cap 2230. Hence each perforated cap strip section can be torn off, or detached from, the main strip such that the cap 2230 can be peeled opened for later use (see FIG. 25B). Or, alternatively each cap can be peeled open from the cap strip for immediate use (see FIG. 25A).

In exemplary implementations, strip 2220/2250/2255 includes an attachment portion, such as an opening 2240 at least at one end thereof, for example to accommodate a hanger of an IV pole such that device 2260 can be hung on the IV pole for convenience. Other variations of an attachment portion, or means for selectively placing or hanging strip 2220/2250/2255 on an IV pole, such as a hook or the like, can be integral with, or attached to, strip 2220/2250/2255 as would be readily appreciated by one of ordinary skill in the art.

Referring to FIGS. 26A and 26B, a dispensing device 2360 according to an exemplary embodiment of the present invention, includes a plurality of caps 2330 disposed on a hanging strip 2320 which can be any shape, such as for example an injection molded runner bar including an attachment portion, such as top hook 2340, or other means for selectively placing or hanging the strip on an IV pole. Caps 2330 can be configured structurally and functionally like any of the caps illustrated in the examples of FIGS. 1A, 1B, and 3A through 21C and described above with reference thereto. According to an exemplary implementation, each cap 2330 is sealed, for example, with a peel strip 2372 similar to individual caps illustrated in the examples of FIGS. 1A, 1B, 4B, 8B, 11B, 14B, 15, 20B, and 21B.

In a further exemplary implementation, each cap 2330 is attached to strip 2372, for example by prongs 2380 attached to and extending away from the surface of the strip 2372. In an exemplary implementation, prongs 2380 are configured as runner gate prongs that connect each cap 2330 (for example, at exterior surface of a cap's top) with the strip 2372 configured as main injection molded runner bar. As illustrated in the example of FIG. 26A, cap 2330 torn away, or removed, from prong 2380 has peel film 2372 still adhered to the cap, so that it can be used at a later time.

In yet another exemplary implementation, as illustrated in the example of FIG. 26B dispensing device 2360 can have multiple prongs 2380 attached to strip 2372 at diametrically opposite sides thereof such that, for example two caps 2380 can be attached to strip 2372 at essentially the same longitudinal location on strip 2372. Such a configuration can allow, for example, for twice as many caps attached to the same length strip.

While the present invention has been shown and described with reference to certain exemplary embodiments thereof, it will be understood by those skilled in the art that various changes in form and details may be made therein without departing from the spirit and scope of the embodiments of the present invention. For example, a disinfection sponge can comprise any suitable disinfecting or other application-specific substance, and can be made of any suitable material. Also, the cap can be single shot molded, or made by other suitable process.

In addition, the included drawing figures further describe non-limiting examples of implementations of certain exemplary embodiments of the present invention and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Other objects, advantages and salient features of the invention will become apparent to those skilled in the art from the details provided, which, taken in conjunction with the annexed drawing figures, disclose exemplary embodiments of the invention.

We claim:

1. A method of connecting a first medical device connector and a second medical device connector, wherein
the first medical devices connector comprises
a first start thread path having a first major profile, a first minor profile, a first pitch, and a first thread section profile, and
at least a second start thread path having a second major profile, a second minor profile, a second pitch, and a second thread section profile,
the first thread section profile and the second thread section profile being different, and the first start thread path and the second start thread path forming a female thread pattern,
the second medical device connector comprises a complimentary male thread having a third major profile with a uniform outer diameter, a third minor profile, and a third pitch substantially equivalent to the first pitch, and
the first and second start thread paths are configured to interface with the complimentary male thread,
the method comprising:
engaging the complimentary male thread of the second medical device connector by at least the first start thread path contacting the third major profile,
thereby forming a first helical void by the space enclosed by the first start thread path of the first medical device connector and at least one of the third major profile and the third minor profile of the complimentary male thread of the second medical device connector.

2. The method of claim 1 further comprising:
engaging the complimentary male thread of the second medical device connector by at least the second start thread path contacting the third major profile,
thereby forming a second helical void by the space enclosed by the second start thread path of the first medical device connector and at least one of the third major profile and the third minor profile of the complimentary male thread of the second medical device connector, the second helical void being larger than the first helical void.

3. The method of claim 1, wherein
the first pitch and the second pitch are substantially equivalent.

4. The method of claim 1 wherein
said first start thread path and said second start thread path further comprise respective root section profiles and respective crest section profiles, wherein the respective root section profiles are substantially similar and the respective crest section profiles are substantially different.

5. The method of claim 1 wherein
the second start thread path interfaces with the complimentary male thread substantially tangentially.

6. The method of claim 1, wherein
the first start thread path interfaces with the complimentary male thread to substantially engage the complimentary male thread.

7. The method of claim 1, wherein
the first start thread path interfaces with the complimentary male thread to substantially engage at least a portion of the complimentary male thread tangentially and non-tangentially.

8. A method of capping a medical device connector, wherein
a cap comprises
a first start thread path having a first major profile, a first minor profile, a first pitch, and a first thread section profile,
at least a second start thread path having a second major profile, a second minor profile, a second pitch, and a second thread section profile, and
an inner cavity comprising an inner surface having the first and second start thread paths, a closed end, and an open end opposite the closed end comprising an opening,
the first thread section profile and the second thread section profile being different,
a medical device connector comprises a complimentary male thread having a third major profile with a uniform outer diameter, a third minor profile, and a third pitch substantially equivalent to the first pitch, and
the first and second start thread paths are configured to interface with the complimentary male thread,
the method comprising:
engaging the complimentary male thread of the medical device connector by at least the first start thread path contacting the third major profile,
thereby forming a first airflow path from a proximal end of the cap to the inner cavity via a first helical void formed by the space enclosed by the first start thread path of the cap and at least one of the third major profile and the third minor profile of the complimentary male thread of the medical device connector.

9. The method of claim 8 further comprising:
engaging the complimentary male thread of the medical device connector by at least the second start thread path contacting the third major profile,
thereby forming a second airflow path from a proximal end of the cap to the inner cavity via a second helical void by the space enclosed by the second start thread path of the cap and at least one of the third major profile and the third minor profile of the complimentary male thread of the medical device connector, the second helical void being larger than the first helical void.

10. The method of claim 8 further comprising
retaining a disinfection agent retention sponge in the inner cavity essentially at a distal end of the cap.

11. The method of claim 8 wherein
the inner surface forms an essentially frustoconical inner cavity having a larger cross section at the proximal end of the cap.

12. The method of claim 8 wherein
the inner surface forms an essentially cylindrical inner cavity having a cross section greater than the third major profile of the complimentary male thread of the secondary medical device connector.

13. The method of claim 8, wherein
the first start thread path interfaces with the complimentary male thread to substantially engage at least a portion of the complimentary male thread tangentially and non-tangentially.

14. The method of claim 8, wherein the first pitch and the second pitch are substantially equivalent.

* * * * *